(12) United States Patent
Palo

(10) Patent No.: US 6,927,401 B1
(45) Date of Patent: Aug. 9, 2005

(54) METHOD OF CHARACTERIZING FLUORESCENT MOLECULES OR OTHER PARTICLES USING GENERATING FUNCTIONS

(75) Inventor: Kaupo Palo, Haabneeme (EE)

(73) Assignee: Evotec OAI AG, Hamburg (DE)

( * ) Notice: Subject to any disclaimer, the term of this patent is extended or adjusted under 35 U.S.C. 154(b) by 0 days.

(21) Appl. No.: 09/869,581

(22) PCT Filed: Apr. 29, 2000

(86) PCT No.: PCT/EP00/03890

§ 371 (c)(1),
(2), (4) Date: Oct. 22, 2001

(87) PCT Pub. No.: WO00/66985

PCT Pub. Date: Nov. 9, 2000

Related U.S. Application Data

(63) Continuation of application No. 09/338,439, filed on Jun. 23, 1999, now Pat. No. 6,376,843.
(60) Provisional application No. 60/181,564, filed on Feb. 10, 2000, and provisional application No. 60/131,657, filed on Apr. 29, 1999.

(30) Foreign Application Priority Data

| Jun. 23, 1999 | (EP) | 99112104 |
| Dec. 23, 1999 | (EP) | 99125745 |

(51) Int. Cl.[7] .............................................. G01N 21/64
(52) U.S. Cl. .................................. 250/458.1; 250/459.1
(58) Field of Search ........................ 250/458.1, 459.1, 250/461.1, 461.2, 372, 201.3; 356/318, 417

(56) References Cited

U.S. PATENT DOCUMENTS

| 4,198,571 A | 4/1980 | Sheppard | |
| 5,149,972 A | * 9/1992 | Fay et al. | 250/461.1 |
| 5,528,046 A | * 6/1996 | Ishikawa | 250/461.2 |

(Continued)

FOREIGN PATENT DOCUMENTS

| EP | 0 836 090 A1 | 4/1998 |
| WO | WO 98/16814 | 4/1998 |
| WO | WO 98/23941 | 6/1998 |

OTHER PUBLICATIONS

Hong Qian et al., "Distribution of Molecular Aggregation by Analysis of Fluctuation Moments", vol. 87, pp. 5479–5483, Jul. 1990.

(Continued)

*Primary Examiner*—Constantine Hannaher
*Assistant Examiner*—Otilia Gabor
(74) *Attorney, Agent, or Firm*—Jacobson Holman PLLC

(57) ABSTRACT

A method for characterizing fluorescent molecules or other particles in samples comprising the steps of:
a) monitoring fluctuating intensity of fluorescence emitted by the molecules or other particles in at least one measurement volume of a non-uniform spatial brightness profile by measuring numbers of photon counts in primary time intervals by a single or more photon detectors,
b) determining at least one distribution of numbers of photon counts, $\hat{P}(n)$, from the measured numbers of photon counts,
c) determining physical quantities characteristic to said particles by fitting the distribution of numbers of photon counts $\hat{P}(n)$,
wherein the fitting procedure involves calculation of a theoretical distribution function of the number of photon counts $P(n)$ through its generating function, defined as $$G(\vec{\xi}) = \sum_n \vec{\xi}^{\,n} P(n).$$

2 Claims, 35 Drawing Sheets

U.S. PATENT DOCUMENTS

| | | | | |
|---|---|---|---|---|
| 5,739,040 | A | * | 4/1998 | Ishikawa ..................... 436/172 |
| 5,866,911 | A | | 2/1999 | Baer |
| 6,049,380 | A | * | 4/2000 | Goodwin et al. ........... 356/317 |
| 6,141,096 | A | * | 10/2000 | Stern et al. ................. 356/318 |
| 6,361,956 | B1 | * | 3/2002 | Hanninen et al. ............ 435/7.1 |
| 6,376,843 | B1 | * | 4/2002 | Palo ........................ 250/458.1 |
| 6,515,289 | B1 | * | 2/2003 | Kask ........................ 250/459.1 |
| 6,556,296 | B1 | * | 4/2003 | Palo ........................... 356/317 |
| 2002/0063863 | A1 | * | 5/2002 | Kask ........................... 356/317 |
| 2003/0013086 | A1 | * | 1/2003 | Kask .............................. 435/6 |

OTHER PUBLICATIONS

Hong Qian et al., "On the Analysis of High Order Moments of Fluorescence Fluctuations", vol. 57, pp. 375–380, Feb. 1990.

* cited by examiner

METHOD OF CHARACTERIZING FLUORESCENT MOLECULES OR OTHER PARTICLES USING GENERATING FUNCTIONS

This application is a 371 of PCT/EP00/03890 filed Apr. 29, 2000, which claims benefit of Ser. No. 60/181,564 filed Feb. 10, 2000, and is a continuation of Ser. No. 09/338,439 filed Jun. 23, 1999 now U.S. Pat. No. 6,376,843, which claims benefit of No. 60/131,657 filed Apr. 29, 1999.

This invention relates to the field of fluorescence spectroscopy, and more particularly to a method for determining characteristic physical quantities of fluorescent molecules or other particles present in a sample.

U.S. Pat. No. 4,198,571 discloses a scanning microscope including first and second focussing means arranged confocally, at least one focussing means being of annular form, a coherent radiation detection means arranged to receive radiation from one focussing means, and scanning means to scan an object in the focal plane.

U.S. Pat. No. 5,866,911 discloses that in scanned optical systems such as confocal laser microscopes wherein a beam of light is focused to a spot in a specimen to excite a fluorescent species or other excitable species in the spot, the effective size of the excitation is made smaller than the size of the spot by providing a beam of light of wavelength adapted to quench the excitation of the excitable species, shaping this second beam into a pattern with a central intensity minimum, and overlapping this central minimum with the central intensity maximum of the focused spot, so that within the spot the intensity of quenching light increases with distance from the center of the spot, thereby preferentially quenching excitation in the peripheral parts of the spot, and thereby reducing the effective size of the excitation and thus improving the resolution of the system.

The primary data of an experiment in fluorescence correlation spectroscopy (FCS, a prior art technique) is a sequence of photon counts detected from a microscopic measurement volume. An essential attribute of the fluorescence correlation analysis is the calculation of the second order autocorrelation function of photon detection. This is a way how a stochastic function (of photon counts) is transformed into a statistical function having an expected shape, serving as a means to estimate some parameters of the sample. However, the calculation of the autocorrelation function is not the only way for extracting information about the sample from the sequence of photon counts. Further approaches are based on moment analysis and direct analysis of the distribution of the number of photon counts per given time interval (Qian and Elson, Proc. Natl. Acad. Sci. USA, 87: 5479–483, 1990; Qian and Elson, Biophys. J. 57: 375–380, 1990).

The intensity of fluorescence detected from a particle within a sample is not uniform but depends on the coordinates of the particle with respect to the focus of the optical system. Therefore, a reliable interpretation of measurements should account for the geometry of the illuminated measurement volume. Even though the calculation of a theoretical distribution of the number of photon counts is more complex for a bell-shaped profile than for a rectangular one, the distribution of the number of photon counts sensitively depends on values of the concentration and the specific brightness of fluorescent species, and therefore, the measured distributions of the number of photon counts can be used for sample analysis. The term specific brightness, denotes the mean count rate of the detector from light emitted by a particle of given species situated in a certain point in the sample, conventionally in the point where the value of the spatial brightness profile function is unity.

The first realization of this kind of analysis was demonstrated on the basis of moments of the photon count number distribution (Qian and Elson, Proc. Natl. Acad. Sci. USA, 87: 5479–483, 1990). The k-th factorial moment of the photon count number distribution P(n) is defined as $$F_k = \sum_n \frac{n!}{(n-k)!} P(n). \quad (1)$$

In turn, factorial moments are closely related to factorial cumulants, $$F_k = \sum_{l=0}^{k-1} C_l^{k-1} K_{k-l} F_l, \text{ or} \quad (2)$$

$$K_k = F_k - \sum_{l=1}^{k-1} C_l^{k-1} K_{k-l} F_l. \quad (3)$$

($C_l^k$s are binomial coefficients, and $K_k$s are cumulants.) The basic expression used in moment analysis, derived for ideal solutions, relate k-th order cumulant to concentrations ($c_i$) and specific brightness values ($q_i$)

$$K_k = \chi_k \sum_i c_i (q_i T)^k. \quad (4)$$

Here, $\chi_k$ is the k-th moment of the relative spatial brightness profile B(r):

$$\chi_k = \int_{(V)} B^k(r) dV. \quad (5)$$

Usually in FCS, the unit of volume and the unit of B are selected which yield $\chi_1 = \chi_2 = 1$. After selecting this convention, concentrations in the equations are dimensionless, expressing the mean number of particles per measurement volume, and the specific brightness of any species equals the mean count rate from a particle if situated in the focus divided by the numeric value of B(O). The value of the constant B(O) a characteristic of optical equipment. It can be calculated from estimated parameters of the spatial intensity profile (see below).

Qian and Elson used experimental values of the first three cumulants to determine unknown parameters of the sample. The number of cumulants which can be reliably determined from experiments is usually three to four. This sets a limit to the applicability of the moment analysis.

The idea behind the so-called fluorescence intensity distribution analysis, which has in detail been described in the international patent application PCT/EP 97/05619 (international publication number WO 98/16814), can be well understood by imagining an ideal case when a measurement volume is uniformly illuminated and when there is almost never more than a single particle illuminated at a time; similar to the ideal situation in cell sorters. Under these circumstances, each time when a particle enters the measurement volume, fluorescence intensity jumps to a value corresponding to the brightness of a given type of particles. Naturally, the probability that this intensity occurs at an arbitrary time moment equals the product of the concentration of a given species and the size of the measurement volume. Another fluorescent species which may be present in the sample solution produces intensity jumps to another value characteristic of this other species. In summary, the distribution of light intensity is in a straightforward way determined by the values of concentration and specific brightness of each fluorescent species in the sample solution.

Only in the above-described ideal case can it be assumed that the light intensity reaching the detector from a particle as a function of coordinates of the particle is constant over the whole measurement volume, and zero outside it. In the first approximation, it is also assumed that the diffusion of a fluorescent particle is negligible during the counting Interval T. Under these two assumptions, the distribution of the number of photon counts emitted by a single fluorescent species can be analytically expressed as double Poissonian: the distribution of the number of particles of given species within this volume is Poissonian, while the conditional probability distribution of the number of photons assuming a given number of particles is also Poissonian. The double Polssonian distribution has two parameters: the mean number of particles in the measurement volume, c and the mean number of photons emitted by a single particle per dwell time, qT. The distribution of the number of photon counts n corresponding to a single species is expressed as $$P(n; c, q) = \sum_{m=0}^{\infty} \frac{c^m}{m!} e^{-c} \frac{(mqT)^n}{n!} e^{-mqT}, \quad (6)$$

where m runs over the number of molecules in the measurement volume. If $P_i(n)$ denotes the distribution of the number of photon counts from species i, then the resultant distribution $P(n)$ is expressed as $$P(n) = \sum_{\{n_i\}} \prod_i P_i(n_i) \delta\left(n, \sum_i n_i\right) \quad (7)$$

This means that $P(n)$ can be calculated as a convolution of the series of distributions $P_i(n)$.

Like in FCS, the rectangular sample profile is a theoretical model which can hardly be applied in experiments. However, one may divide the measurement volume into a great number of volume elements and assume that within each of them, the intensity of a molecule is constant. Contribution to photon count number distribution from a volume element is therefore double Poissonian with parameters cdV and qTB(r). (Here q denotes count rate from a molecule in a selected standard position where B=1, and B(r) is the spatial brightness profile function of coordinates.) The overall distribution of the number of photon counts can be expressed as a convolution integral over double Poissonian distributions. Integration is a one-dimensional rather than a three-dimensional problem here, because the result of integration does not depend on actual positions of volume elements in respect to each other. Figuratively, one may rearrange the three-dimensional array of volume elements into a one-dimensional array, for example in the decreasing order of the value of B.

In a number of first experiments described in the international patent application PCT/EP 97/05619 (published as WO 98/16814), the photon count number distribution was indeed fitted, using the convolution technique. The sample model consisted of twenty spatial sections, each characterized by its volume $V_j$ and brightness $B_j$. However, the technique described in this patent application is slow and inconvenient in cases involving a high number of samples to be analyzed, like in diagnostics or drug discovery, or in analyzing distribution functions involving more than a single argument.

Therefore, it is an object of the present invention to present a convenient and much faster technique for analyzing fluorescence intensity fluctuations.

According to the present invention there is provided a method for characterizing fluorescent molecules or other particles in samples, the method comprising the steps of:

a) monitoring fluctuating intensity of fluorescence emitted by the molecules or other particles in at least one measurement volume of a non-uniform spatial brightness profile by measuring numbers of photon counts in primary time intervals by a single or more photon detectors, b) determining at least one distribution of numbers of photon counts, $\hat{P}(n)$, from the measured numbers of photon counts, c) determining physical quantities characteristic to said particles by fitting the distribution of numbers of photon counts $\hat{P}(n)$, wherein the fitting procedure involves calculation of a theoretical distribution function of the number of photon counts $P(n)$ through its generating function, defined as $$G(\vec{\xi}) = \sum_n \vec{\xi}^n P(n).$$

In the following, sometimes the wording "histogram" will be used instead of "experimentally determined distribution function" or "experimentally determined distribution".

The formal definition of the generating function of a distribution $P(n)$ is as follows:

$$G(\xi) = \sum_{n=0}^{\infty} \xi^n P(n). \quad (8)$$

What makes the generating function attractive in count number distribution analysis is the additivity of its logarithm: logarithms of generating functions of photon count number distributions of independent sources, like different volume elements as well as different species, are simply added for the calculation of the generating function of the combined distribution because the transformation (8) maps distribution convolutions into the products of the corresponding generating functions.

Four particular examples of the present invention have been developed in detail and will be described below:

1. one-dimensional fluorescence intensity distribution analysis (denoted by FIDA or 1D-FIDA) in which a single distribution function of numbers of photon counts is fitted yielding the specific brightness of a fluorescent molecule or other particle as a characteristic physical quantity;

2. two-dimensional fluorescence intensity distribution analysis (2D-FIDA) in which a joint distribution function of numbers of photon counts is fitted yielding two specific brightness values of a fluorescent molecule or other particle as characteristic physical quantities. 2D-FIDA can be applied in a polarization mode or in a spectral mode as explained in detail below;

3. fluorescence intensity multiple distribution analysis (FIMDA) in which a series of distribution functions of photon count numbers at different width of counting time intervals is fitted yielding the specific brightness and the translational diffusion time as characteristic physical quantities; and 4. fluorescence autoconvoluted intensity distribution analysis (FACID) in which a series of distribution function of photon count numbers each corresponding to the same counting time interval is fitted. However, different delay times between two parts of a counting time interval are used. FACID yields also the specific brightness and the translational diffusion time as characteristic physical-quantities.

In a particular preferred embodiment, one might monitor the fluctuating fluorescence intensity in consecutive primary time intervals of equal width. The above mentioned examples, 1D-FIDA, 2D-FIDA, FIMDA and FACID, make use of this convenient embodiment in which the available information is optimally used. However, it is also possible to use non-consecutive primary time intervals and/or primary time intervals of different width. Typical primary time intervals have a width in the order of a microsecond or tens of microseconds. The total data collection time is usually several tenth of seconds up to tens of seconds.

In a further preferred embodiment, numbers of photon counts $\{n_i\}$ subject to determination of a histogram $\hat{P}(n)$ in step b) are derived from numbers of photon counts in primary time intervals $\{N_j\}$ by addition of numbers of photon counts from primary time intervals according to a predetermined rule. 1D-FIDA, 2D-FIDA, FIMDA and FACID make also use of this embodiment.

One might e.g. be interested in choosing numbers of photon counts $\{n_i\}$ subject to determination of a histogram $\hat{P}(n)$ which are calculated from the numbers of photon counts in primary time intervals $\{N_j\}$ according to the rule $$n_i = \sum_{k=1}^{M} N_{Mi+k},$$

where M is an integer number expressing how many times the time interval in which $\{n_i\}$ is determined is longer than the primary time interval. 1D-FIDA, 2D-FIDA and FIMDA preferably make use of this embodiment.

In a further embodiment, numbers of photon counts $\{n_i\}$ are derived from predetermined primary time intervals according to a rule in which primary time intervals are separated by a time delay. In particular, the following rule can be applied:

$$n_i = \sum_{k=1}^{M} (N_{Mi+k} + N_{M(i+L)+k}),$$

where M and L are positive integer numbers, $\{n_i\}$ are numbers of photon counts subject to determination of a histogram $\hat{P}(n)$, and $\{N_j\}$ are the numbers of photon counts in primary time intervals. In this formula, 2M is the number of primary time intervals per a counting time interval (in which $n_i$ is determined) while L is the number of missed primary time intervals constituting a delay between two parts of the counting time interval. FACID preferably makes use of this embodiment.

In some cases, it might be preferred to determine not only a single histogram $\hat{P}(n)$ in step b), but rather a set of histograms, $\hat{P}(n)$. These can be determined according to a set of different rules, said set of histograms being fitted jointly in step c). As an example a set of histograms with different values of M and/or L might be fitted jointly. FIMDA and FACID make use of this embodiment.

Typical physical quantities which might be determined in step c) according to the present invention are concentration, specific brightness and/or diffusion coefficient of molecules or other particles.

In a further preferred embodiment, the generating function is calculated using the expression $G(\xi)=\exp[\int dqc(q) \int d^3r(e^{(\xi-1)qTB(r)}-1)]$, where $c(q)$ is the density of particles with specific brightness q, T is the length of the counting interval, and $B(r)$ is the spatial brightness profile as a function of coordinates.

Applying the definition (8) to formula (6) with c→cdV and q→qB(r), the contribution from a particular species and a selected volume element dV can be written as $$G_i(\xi;dV)=\exp[c_i dV(e^{(\xi-1)q_i TB(r)}-1)]. \qquad (9)$$

Therefore, the generating function of the total photon count number distribution can be expressed in a closed form $$G(\xi) = \exp\left[\sum_i c_i \int (e^{(\xi-1)q_i TB(r)} - 1)dV\right]. \qquad (10)$$

Numeric integration according to Eq. (9) followed by a fast Fourier transform is the most effective means of calculating the theoretical distribution P(n) corresponding to a given sample (i.e., given concentrations and specific brightness values of fluorescent species). If one selects $\xi=e^{i\phi}$, then the distribution P(n) and its generating function G($\phi$) are interrelated by the Fourier transform. Therefore, it is particularly preferred to select the argument of the generating function in the form $\xi=e^{-i\phi}$ and to use a fast Fourier transform algorithm in calculation of the theoretical distribution of the number of photon counts out of its generating function. 1D-FIDA, 2D-FIDA, FIMDA and FACID preferably make use of this embodiment.

When calculating the theoretical distribution P(n) in step c) according to the present invention, the spatial brightness profile might be modeled by a mathematical relationship between volume and spatial brightness. In particular, one might model the spatial brightness profile by the following expression:

$$\frac{dV}{dx} = A_0 x(1 + a_1 x + a_2 x^2),$$

where dV denotes a volume element, x denotes logarithm of the relative spatial brightness, $A_0$ is a constant selecting the unit of volume, and $a_1$ and $a_2$ are empirically estimated parameters of the shape of the spatial brightness function. In a further preferred embodiment, one might model the spatial brightness profile by the following expression:

$$\frac{dV}{dx} = A_0 x^{a_3}(1 + a_1 x + a_2 x^2).$$

Some fluorescent species may have a significantly wide distribution of specific brightness. For example vesicles, which are likely to have a significantly broad size distribution and a random number of receptors, may have trapped a random number of labeled ligand molecules. In order to fit count number histograms for samples containing such kind of species, it is useful to modify Eq. (10) in the following manner. The assumption is made that the distribution of brightness of particles q within a species is mathematically expressed as follows:

$$\rho(q) \propto q^{a-1} e^{-bq} \qquad (11)$$

This expression has been selected for the sake of convenience: all moments of this distribution can be analytically calculated, using the following formula:

$$\int_0^\infty x^a e^{-bx} dx = \frac{\Gamma(a+1)}{b^{a+1}}. \quad (12)$$

It is straightforward to derive the modified generating function of a photon count number distribution. One can rewrite Eq. (9) as follows:

$$G(\xi) = \exp\left[\sum_i c_i \int dV \int_0^\infty dq \rho(q; a_i, b_i)(e^{(\xi-1)qTB(r)} - 1)\right], \quad (13)$$

where $$\rho(q; a, b) = \frac{b^a}{\Gamma(a)} q^{a-1} e^{-bq}. \quad (14)$$

The integral over q can be performed analytically:

$$G(\xi) = \exp\left\{\sum_i c_i \int dV \left[\left(\frac{b_i}{b_i - (\xi-1)TB(x)}\right)^{a_i} - 1\right]\right\}, \quad (15)$$

The parameters $a_i$ and $b_i$ are related to the mean brightness $\bar{q}_i$ and the width of the brightness distribution $\sigma_i^2$ by $$a_i = \frac{\bar{q}_i^2}{\sigma_i^2}, \quad b_i = \frac{\bar{q}_i}{\sigma_i^2}. \quad (16)$$

In the range of obtained count numbers, the probability to obtain a particular count number usually varies by many orders of magnitude, see for example the distribution of FIG. 1. Consequently, the variance of the number of events with a given count number has a strong dependence on the count number. To determine weights for least squares fitting, one may assume that light intensities in all counting intervals are independent. Under this assumption, one has a problem of distributing M events over choices of different count numbers n, each particular outcome having a given probability of realization, P(n). Covariance matrix elements of the distribution can be expressed as follows:

$$\langle \Delta P(n) \Delta P(m) \rangle = \frac{P(n)\delta(n,m) - P(n)P(m)}{M}, \quad (17)$$

where M is the number of counting intervals per experiment.

The covariance matrix of Eq. 17 is singular. As the weight matrix, we are justified to use its "weak inverse" diagonal matrix expressed as follows:

$$W_n = \frac{M}{P(n)}. \quad (18)$$

Dispersion matrix (17) corresponds to the multinomial distribution of statistical realizations of histograms. The Poissonian distribution, with the constraint that the total number of counting intervals M is fixed, will lead to the multinomial distribution. This is the rationale behind using Poissonian weights as given in Eq. (18).

Let $n_k$ be the expectation value of the number of events of counting k photons and let $$N = \sum_k n_k$$

be their sum. Let $m_k$ be a statistical realization with $$M = \sum_k m_k.$$

Assume that realizations $m_0, m_1, \ldots$ obey Poissonian statistics $$P(m_0, m_1, \ldots) = \frac{[n_0, n_1, \ldots]^{[m_0, m_1, \ldots]}}{[m_0, m_1, \ldots]!} e^{-N}, \quad (19)$$

where we have introduced the notation $n_0^{m_0} n_1^{m_1} \ldots \equiv [n_0, n_1, \ldots]^{[m_0, m_1, \ldots]}$ and $m_0! m_1! \ldots \equiv [m_0, m_1, \ldots]!$. The probability of having the total of M events is $$P(M) = \frac{N^M}{N!} e^{-N}. \quad (20)$$

The conditional probability of having $m_0, m_1, \ldots$ events if there is a total of M events is $$P(m_0, m_1, \ldots | M) \equiv \frac{P(m_0, m_1, \ldots)}{P(M)} = \quad (21)$$

$$\frac{M![n_0, n_1, \ldots]^{[m_0, m_1, \ldots]}}{N^M [m_0, m_1, \ldots]!}, \text{ or}$$

$$P(m_0, m_1, \ldots | M) \equiv C_{m_0, m_1, \ldots}^M [p_0, p_1, \ldots]^{[m_0, m_1, \ldots]}.$$

This is the multinomial distribution where we have introduced:

$$p_k \equiv \frac{n_k}{M}$$

and $C_{m_0, m_1, \ldots}^M$ are multinomial coefficients.

In general, a linear or linearized least squares fitting returns -not only the values of the estimated parameters, but also their covariance matrix, provided the weights have been meaningfully set. It may turn out to be possible to express the statistical errors of the estimated parameters analytically in some simple cases (e.g., for the rectangular sample profile and single species) but in applications at least two-component analysis is usually of interest. Therefore, one may be satisfied with the numerical calculations of statistical errors. In addition to the "theoretical" errors with the assumption of non-correlated measurements (Eq. (17)), in some cases statistical errors have been estimated empirically, making a series of about a hundred FIDA experiments on identical conditions. As a rule, empirical errors are higher than theoretical ones by a factor of three to four. Empirical errors appear to be closer to the theoretical ones in scanning experiments. Therefore we are convinced that the main reason of the underestimation of theoretical errors is the assumption of non-correlated measurements. Table 1 compares statistical errors of parameters estimated by fitting a photon count number histogram (FIDA) according to the present invention and by the moment analysis. Error values are determined through processing a series of simulated histograms. The present invention is overwhelmingly better than the moment analysis if the number of estimated parameters is higher than three.

TABLE 1

| Data collection time, s | Counting time interval, μs | Number of species | Number of estimated parameters | Parameter specification | Value (qs in kHz) | Percent error of FIDA (invention) | Percent error of moment analysis |
|---|---|---|---|---|---|---|---|
| 10.0 | 40.0 | 1 | 2 | c | 0.5 | 0.59 | 0.54 |
|  |  |  |  | q | 60.0 | 0.56 | 0.51 |
| 10.0 | 40.0 | 2 | 3 | $c_1$ | 0.05 | 2.00 | 2.71 |
|  |  |  |  | $q_1$ | 150.0 | 1.54 | 1.89 |
|  |  |  |  | $c_2$ | 3.0 | 0.53 | 0.62 |
|  |  |  |  | $q_2$ | 5.0 (fixed) |  |  |
| 10.0 | 40.0 | 2 | 4 | $c_1$ | 0.05 | 2.26 | 4.99 |
|  |  |  |  | $q_1$ | 150.0 | 1.63 | 2.53 |
|  |  |  |  | $c_2$ | 3.0 | 3.18 | 17.8 |
|  |  |  |  | $q_2$ | 5.0 | 3.35 | 14.9 |

In a further preferred embodiment, the method according to the present invention is applied to fit a joint distribution of photon count numbers. 2D-FIDA is an example of this embodiment. In experiments, fluorescence from a microscopic volume with a fluctuating number of molecules is monitored using an optical set-up (e.g. a confocal microscope) with two detectors. The two detectors may have different polarizational or spectral response. In one embodiment, concentrations of fluorescent species together with two specific brightness values per each species are determined. The two-dimensional fluorescence intensity distribution analysis (2D-FIDA) if used with a polarization cube is a tool which can distinguish fluorescent species with different specific polarization ratios. This is a typical example of a joint analysis of two physical characteristics of single molecules or other particles, granting a significantly improved reliability compared to methods focussed on a single physical characteristic.

In the following, 2D-FIDA is explained in more detail.

In order to express the expected two-dimensional distribution of the number of photon counts, it is favorable to use the following assumptions: (A) Coordinates of particles are random and independent of each other. (B) Contribution to fluorescence intensity from a particle can be expressed as a product of a specific brightness of the particle and a spatial brightness profile function characteristic to the optical equipment. (C) A short counting time interval T is selected, during which brightness of fluorescent particles does not significantly change due to diffusion.

At first, a joint distribution of count numbers from a single fluorescent species and a single small open volume element dV is expressed. The volume element is characterized by coordinates r and spatial brightness B(r), and the fluorescent species is characterized by its specific brightness values $q_1$ and $q_2$. By $q_1$ and $q_2$, mean photon count rates by two detectors from a particle situated at a point where B(r)=1 are denoted. A convenient choice is to select a unit of B, as usual in FCS, by the equation $\chi_1 = \chi_2$, where $\chi_k = \int B^k(r) d^3r$. If the volume element happens to contain m particles, then the expected photon count numbers per time interval T from the volume element are $mq_1 TB(r)$ and $mq_2 TB(r)$, while the distribution of numbers of photon counts from m particles $P(n_1, n_2|m)$ is Poissonian for both detectors independently:

$$P(n_1, n_2|m) = \frac{(mq_1 TB(x))^{n_1}}{n_1!} e^{-mq_1 TB(x)} \frac{(mq_2 TB(x))^{n_2}}{n_2!} e^{-mq_2 TB(x)}. \quad (22)$$

From the other side, under assumption (A), the distribution of the number of particles of given species in the volume element is Poissonian with mean cdV, c denoting concentration:

$$P_{dV}(m) = \frac{(cdV)^m}{m!} e^{-cdV}. \quad (23)$$

The overall distribution of the number of photon counts from the volume element can be expressed using Eqs. 22 and 23:

$$P_{dV}(n_1, n_2) = \sum_m P_{dV}(m) P(n_1, n_2|m) \quad (24)$$

$$= \sum_m \frac{(cdV)^m}{m!} e^{-cdV} \frac{(mq_1 TB(r))^{n_1}}{n_1!} e^{-mq_1 TB(r)} \frac{(mq_2 TB(r))^{n_2}}{n_2!} e^{-mq_2 TB(r)}$$

As in the one-dimensional case described above, a useful representation of a distribution of numbers of photon counts $P(n_1, n_2)$ is its generating function, defined as $$G(\xi_1, \xi_2) = \sum_{n_1=0}^{\infty} \sum_{n_2=0}^{\infty} \xi_1^{n_1} \xi_2^{n_2} P(n_1, n_2). \quad (25)$$

The generating function of the distribution expressed by Eq 24 can be written, as $$G_{dV}(\xi_1, \xi_2) = e^{-cdV} \sum_m \frac{(cdV)^m}{m!} e^{-mq_1 BT} e^{-mq_1 BT} \sum_{n_1} \frac{(m\xi_1 qBT)^{n_1}}{n_1!} \sum_{n_2} \frac{(m\xi_2 qBT)^{n_2}}{n_2!} \quad (26)$$

-continued $$= e^{-cdV} \sum_m \frac{\{cdV\exp[(\xi_1 - 1)q_1 BT]\exp[(\xi_2 - 1)q_2 BT]\}^m}{m!}$$

$$= \exp[cdV(e^{(\xi_1-1)q_1 BT}e^{(\xi_2-1)q_2 BT} - 1)]$$

In particular, if one selects $\xi_k = \exp(i\phi_k)$, then the distribution $P(n_1,n_2)$ and its generating function $G(\phi_1,\phi_2)$ are interrelated by a 2-dimensional Fourier transform. Logarithms of generating functions of photon count number distributions of independent sources, like different volume elements as well as different species, are simply added for the calculation of the combined distribution. Therefore, the generating function of the overall distribution of the number of photon counts can be expressed in a closed form:

$$G(\xi_1, \xi_2) = \exp\left[(\xi_1 - 1)\lambda_1 T + (\xi_2 - 1)\lambda_2 T + \sum_i c_i \int (e^{(\xi_1-1)q_1,TB(r)}e^{(\xi_2-1)q_2,TB(r)} - 1)d^3r\right]. \quad (27)$$

In this formula, a contribution from background count rates, $\lambda_1$ by detector 1 and $\lambda_2$ by detector 2, as well as contributions from different fluorescent species, denoted by the subscript i, have been integrated. Numeric integration according to Eq. 27 followed by a fast Fourier transform is a very efficient means for calculation of the theoretical distribution $P(n_1,n_2)$ corresponding to a given sample (i.e. given concentrations and specific brightness values of fluorescent species).

The spatial brightness function is accounted through the spatial integration on the right side of Eq. 27. The three-dimensional integration can be reduced to a one-dimensional one by replacing three-dimensional coordinates r by a one-dimensional variable, a monotonic function of the spatial brightness B(r). A convenient choice of the variable is $x=\ln[B(0)/B(r)]$. A sufficiently flexible model of the spatial brightness profile is presented by the following expression:

$$\frac{dV}{dx} \propto x^{a_3}(1 + a_1 x + a_2 x^2). \quad (28)$$

In the interval of obtained count numbers, the probability to obtain a particular pair of count numbers usually varies by many orders of magnitude. Consequently, the variance of a data point of a histogram has also a strong dependence on the count numbers. To determine weights for least squares fitting, for simplification it is assumed that coordinates of particles in all counting intervals are randomly selected. (This means one ignores correlations of the coordinates in consecutive counting intervals.) Under this assumption, one has a problem of distributing M events over choices of different pairs of count numbers $n_1$, $n_2$, each particular outcome having a given probability of realization, $P(n_1,n_2)$. Covariance matrix elements of the histogram can be expressed as follows:

$$\langle \Delta P(n_1, n_2)\Delta P(n_1', n_2')\rangle = \frac{P(n_1, n_2)\delta(n_1, n_1')\delta(n_2, n_2') - P(n_1, n_2)P(n_1', n_2')}{M}, \quad (29)$$

where M is the number of counting intervals per experiment.

The covariance matrix of Eq. 29 is singular. As the weight matrix, we are justified to use its "weak inverse" diagonal matrix expressed as follows:

$$W(n_1, n_2) = \frac{M}{P(n_1, n_2)}. \quad (30)$$

In general, a linearized least squares fitting algorithm returns not only values of estimated parameters, but also their covariance matrix, provided weights have been meaningfully set. In addition to "theoretical" errors corresponding to the assumption of uncorrelated measurements (Eq. (30)), in some cases statistical errors have been determined empirically, making a series of about 100 2D-FIDA experiments at identical conditions. As a rule, empirical errors are higher than theoretical ones by a factor of three to four. The main reason of underestimation of theoretical errors is most likely the assumption of uncorrelated measurements.

Even though the assumption of uncorrelated measurements yields underestimated error values, it is a very useful theoretical approximation, allowing to compare accuracy of analysis under different experimental conditions as well as different methods of analysis. Also, this approximation provides an easy method of data simulation which is a useful tool in general. A simple and very fast method of data simulation is calculation of the expected event number as a function of photon count numbers and addition of random Poisson noise to each event number independently.

In Table 2 theoretical errors of one-dimensional and two-dimensional fluorescence intensity distribution analysis according to the present invention are presented in two selected cases of two fluorescent species. In both cases the ratio of specific brightness values of the two species is three. In the case of 2D-FIDA, it is assumed that spectral sensitivities of the two detectors are tuned to different species. In both cases data collection time of 10 s, time window of 40 µs and background count rate of 1 kHz are assumed. Note that the statistical errors of the estimated parameters are significantly lower in the 2D-FIDA example.

TABLE 2

| Method | Parameter specification | Parameter value (selected) | Percent error |
| --- | --- | --- | --- |
| ID-FIDA (according to the invention) | $c_1 V$ | 0.5 | 6.6 |
| | $c_2 V$ | 0.5 | 4.9 |
| | $q_1$ | 60 kHz | 2.2 |
| | $q_2$ | 20 kHz | 10.2 |
| 2D-FIDA (according to the invention) | $c_1 V$ | 0.5 | 1.1 |
| | $c_2 V$ | 0.5 | 1.1 |
| | $q_{A1}$ | 60 kHz | 0.77 |
| | $q_{A2}$ | 20 kHz | 1.2 |
| | $q_{B1}$ | 20 kHz | 1.2 |
| | $q_{B2}$ | 60 kHz | 0.77 |

The two-dimensional fluorescent intensity distribution analysis according to the present invention is in the following compared to a 2-dimensional generalization of the prior art moment analysis.

Factorial moments of the distribution $P(n_1,n_2)$ are defined as $$F_{kl} = \sum_{n_1,n_2} \frac{n_1! n_2!}{(n_1-k)!(n_2-l)!} P(n_1, n_2). \quad (31)$$

Factorial moments are related to factorial cumulants $K_{kl}$ $$K_{kl} = F_{kl} - \sum_{\substack{i,j \\ i+j>0}} C_i^{k-1} C_j^l K_{k-i,l-j} F_{ij}. \quad (32)$$

C denotes binomial coefficients. Cumulants can be expressed through concentrations and specific brightness values by a simple relation The principle of moment analysis is to determine values of a few cumulants from an experiment and solve a system of Eqs. 33 in respect to unknown concentrations and brightness values.

In Table 3 statistical errors of 2D-FIDA (present invention) and 2D-MAFID (a generalization of the prior art in which an one-dimensional moment analysis of fluorescence intensity distribution analysis has been described) are presented determined by generating a series of 30 random histograms of count numbers, simulated for identical "samples", thereafter applying 2D-FIDA and 2D-MAFID, and determining the variance of estimated parameters in both cases. Note a tendency that the advantages of 2D-FIDA compared to 2D-MAFID increase with the number of parameters to be estimated.

TABLE 3

| Data collection time, s | Number of species | Number of estimated parameters | Specification of cumulants used in MAFID | Specification of parameters | True values | Percent error of FIDA | Percent error of MAFID |
|---|---|---|---|---|---|---|---|
| 2 | 1 | 3 | $K_{01}$ | cV | 0.5 | 1.1 | 1.3 |
| | | | $K_{10}$ | $q_A$ | 60 kHz | 1.2 | 1.5 |
| | | | $K_{11}$ | $q_B$ | 40 kHz | 1.3 | 1.6 |
| 10 | 2 | 4 | $K_{01}$ | $c_1 V$ | 0.5 | 1.1 | 2.5 |
| | | | $K_{10}$ | $c_2 V$ | 0.5 | 1.0 | 4.2 |
| | | | $K_{02}$ | $q_{A1}$ | 60 kHz | 0.70 | 1.2 |
| | | | $K_{20}$ | $q_{A2}$ | 20 kHz | (fixed) | (fixed) |
| | | | | $q_{B1}$ | 40 kHz | 1.3 | 5.7 |
| | | | | $q_{B2}$ | 80 kHz | (fixed) | (fixed) |
| 10 | 3 | 5 | $K_{01}$ | $c_1 V$ | 0.2 | 2.0 | 2.4 |
| | | | $K_{10}$ | $c_2 V$ | 0.2 | 1.2 | 1.2 |
| | | | $K_{02}$ | $c_3 V$ | 0.2 | 1.6 | 1.9 |
| | | | $K_{11}$ | $q_{A1}$ | 40 kHz | 1.4 | 1.8 |
| | | | $K_{20}$ | $q_{A2}$ | 20 kHz | (fixed) | (fixed) |
| | | | | $q_{A3}$ | 60 kHz | (fixed) | (fixed) |
| | | | | $q_{B1}$ | 10 kHz | 3.6 | 9.0 |
| | | | | $q_{B2}$ | 60 kHz | (fixed) | (fixed) |
| | | | | $q_{B3}$ | 70 kHz | (fixed) | (fixed) |
| 10 | 2 | 6 | $K_{01}$ | $c_1 V$ | 0.5 | 1.1 | 4.3 |
| | | | $K_{10}$ | $c_2 V$ | 0.5 | 1.0 | 5.0 |
| | | | $K_{02}$ | $q_{A1}$ | 60 kHz | 0.70 | 1.4 |
| | | | $K_{11}$ | $q_{A2}$ | 20 kHz | 1.3 | 4.5 |
| | | | $K_{20}$ | $q_{B1}$ | 40 kHz | 0.90 | 2.9 |
| | | | $K_{21}$ | $q_{B2}$ | 80 kHz | 0.55 | 1.5 |

Error values are calculated from the scattered results of analysis applied to a series of simulated data.

$$K_{kl} = \chi_{k+l} T^{k+l} \sum_i c_i q_{1i}^k q_{2i}^l. \quad (33)$$

If the unit of B is selected by the equation $\chi_1 = \chi_2$, $\chi_1$ has the meaning of the sample volume, denoted by V, and Eq. 33 can be written as $$\gamma_{k+l} K_{kl} = \sum_i (c_i V)(q_{1i} T)^k (q_{2i} T)^l. \quad (34)$$

where γ denotes a series of constants characterizing the brightness profile:

$$\gamma_m = \frac{\chi_1}{\chi_m}. \quad (35)$$

In Table 4 the relative deviation of mean values (i.e, bias) of estimated parameters are presented for 2D-FIDA (present invention) and 2D-MAFID (a generalization of prior art). In each case bias is determined from analysis of a series of thirty simulated random histograms of count numbers. Three cases were analyzed. In the first case, models used in data simulations and data analysis were identical. In the second case, the histograms of count numbers were simulated assuming that particles of the second species are not equivalent but being distributed by their individual brightness with a relative half-width of 20 percent. This phenomenon was intentionally ignored in analysis, however. Of course, applying a slightly inadequate model for analysis produces bias of estimated parameters. The third case is similar to the second one except the relative half-width of the individual brightness distribution of the second species is 50 percent, which is a usual value for vesicular preparations. It is worth noting that methodological deviations are noticeable when mapping weighted residuals of 2D-FIDA in cases two and three, but 2D-FIDA still returns meaningful results. This is a general property: 2D-FIDA which directly fits the original data requires a less exact model than 2D-MAFID which is a method fitting a mathematical transform of the original data.

TABLE 4

| Parameter specification | True value (selected) | Bias of 2D-FIDA, percent | | | Bias of 2D-MAFID, percent | | |
|---|---|---|---|---|---|---|---|
| | | Case 1 | Case 2 | Case 3 | Case 1 | Case 2 | Case 3 |
| $c_1 V$ | 1.0 | +0.1 ± 0.2 | −0.35 | −2.0 | +0.1 ± 0.2 | −6.5 | −28 |
| $c_2 V$ | 0.05 | +0.6 ± 0.4 | −2.0 | −10.6 | +1.8 ± 0.6 | −15.6 | −69 |
| $q_{A1}$ | 20 kHz | −0.1 ± 0.2 | +0.8 | +5.0 | −0.3 ± 0.3 | +10.0 | +58 |
| $q_{A2}$ | 100 kHz | −0.3 ± 0.4 | −0.7 | −11.2 | −0.9 ± 0.3 | +5.5 | +41 |
| $q_{B1}$ | 1 kHz | −1.2 ± 0.5 | +2.6 | +20.6 | −6.7 ± 3.0 | +75 | +563 |
| $q_{B2}$ | 200 kHz | −0.3 ± 0.4 | +1.2 | +1.3 | −0.9 ± 0.3 | +11.6 | +99 |

According to the present invention, confocal techniques are particularly suited to monitor the fluctuating intensity of fluorescence. They may be applied to a wide field of applications, such as biomedicine, diagnostics, high through-put drug screening, sorting processes such as sorting of particles like beads, vesicles, cells, bacteria, viruses etc. The conjugate focal (confocal) technique is based on using a point source of light sharply focused to a diffraction-limited spot on the sample. The emitted light is viewed through a spatial filter (pinhole) that isolates the viewing area to that exactly coincident with the illuminating spot. Thus, the illumination and detection apertures are optically conjugated with each other. Light originating from focal planes other than that of the objective lens is rejected, which effectively provides a very small depth of field. Therefore, in a particular preferred embodiment of the present invention, in step a) a confocal microscope is used for monitoring the intensity of fluorescence. In order to achieve a high signal-to-noise ratio, it is useful to monitor the intensity of fluorescence using an apparatus that comprises: a radiation source (12) for providing excitation radiation (14), an objective (22) for focussing the excitation radiation (14) into a measurement volume (26), a detector (42) for detecting emission radiation (30) that stems from the measurement volume (26), and an opaque means (44) positioned in the pathway (32) of the emission radiation (30) or excitation radiation (14) for erasing the central part of the emission radiation (30) or excitation radiation (14). It might be particularly preferred to use an optical set-up described in detail in FIG. 9.

Figure 10A:
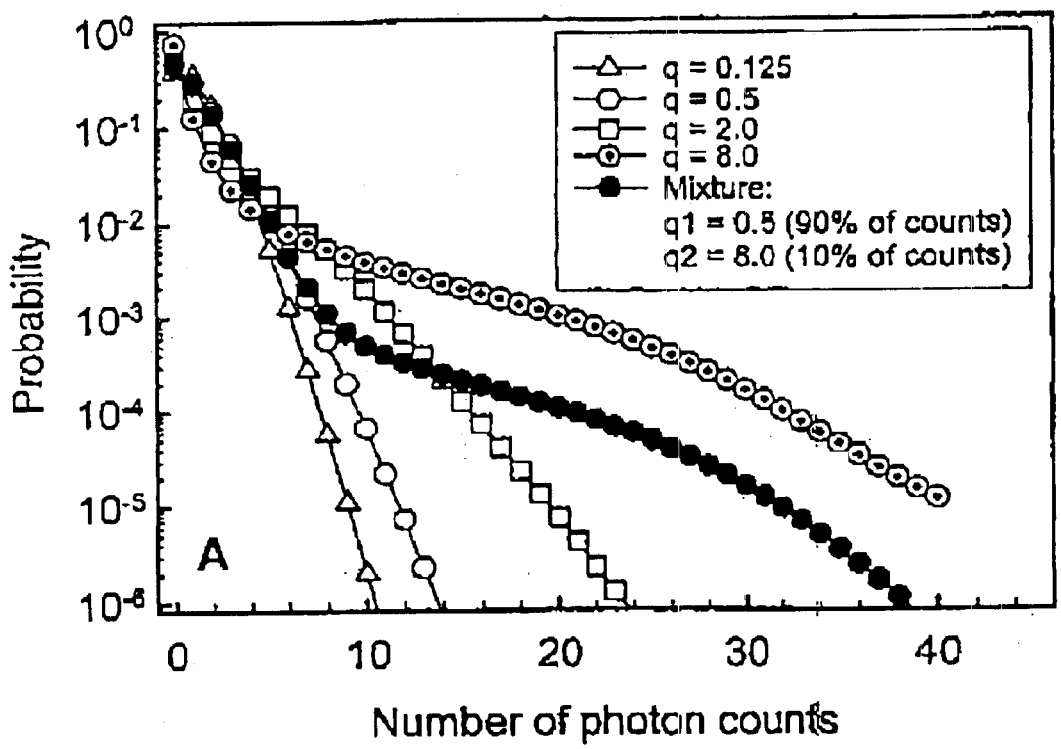
In FIG. 10A, the calculated photon count number distributions, P(n), for cases having identical mean count number $\bar{n}$ but differing by the composition of the sample are plotted.
Figure 10B:
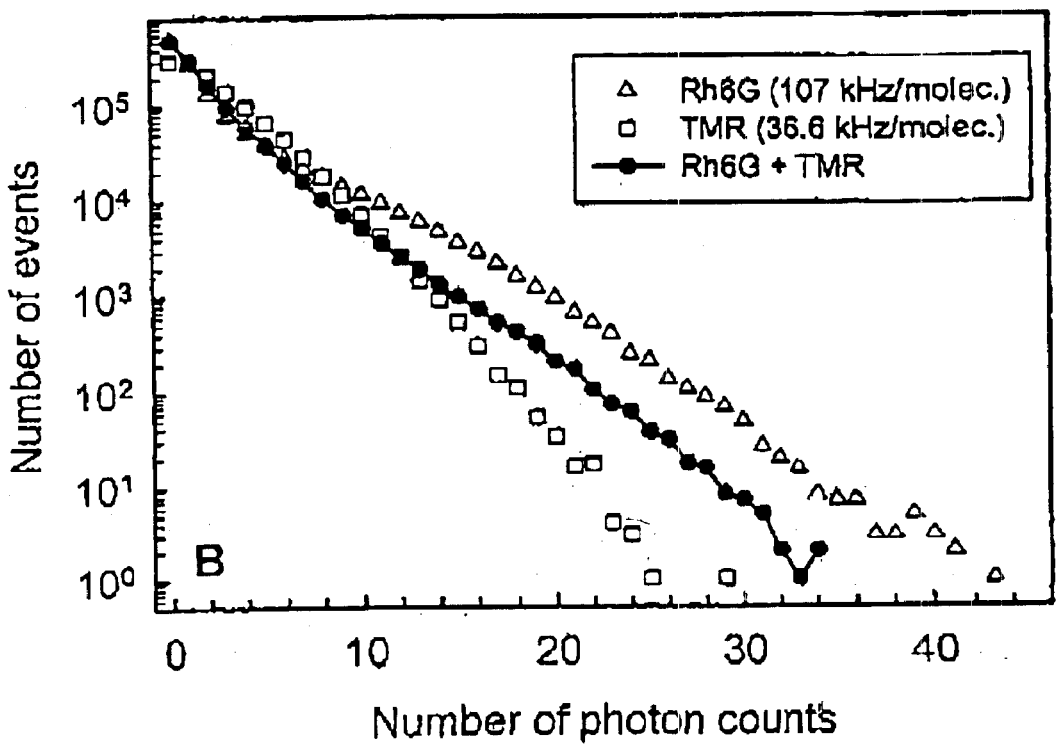
FIG. 10B is a graph of the histograms of the number of photon counts of pure solutions of rhodamine 6G (Rh6G) and tetramethylrhodamine (TMR), as well as a mixture of these two dyes.
Figure 10C:
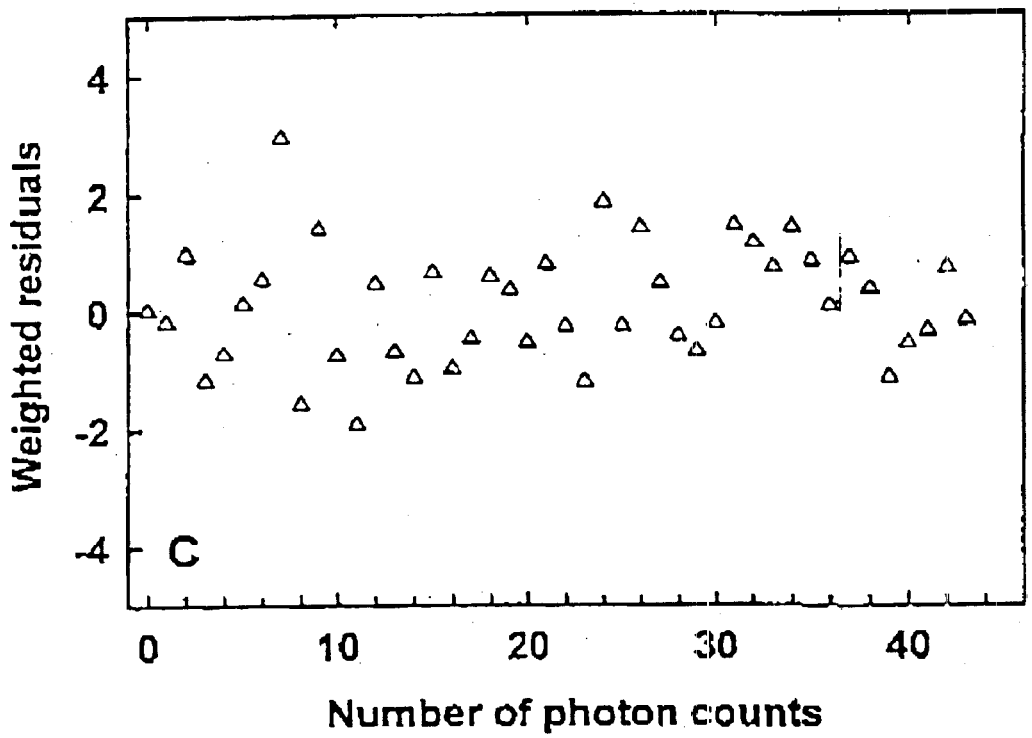

The exemplary residuals for Rh6G are shown in FIG. 10C.

Figure 10D:
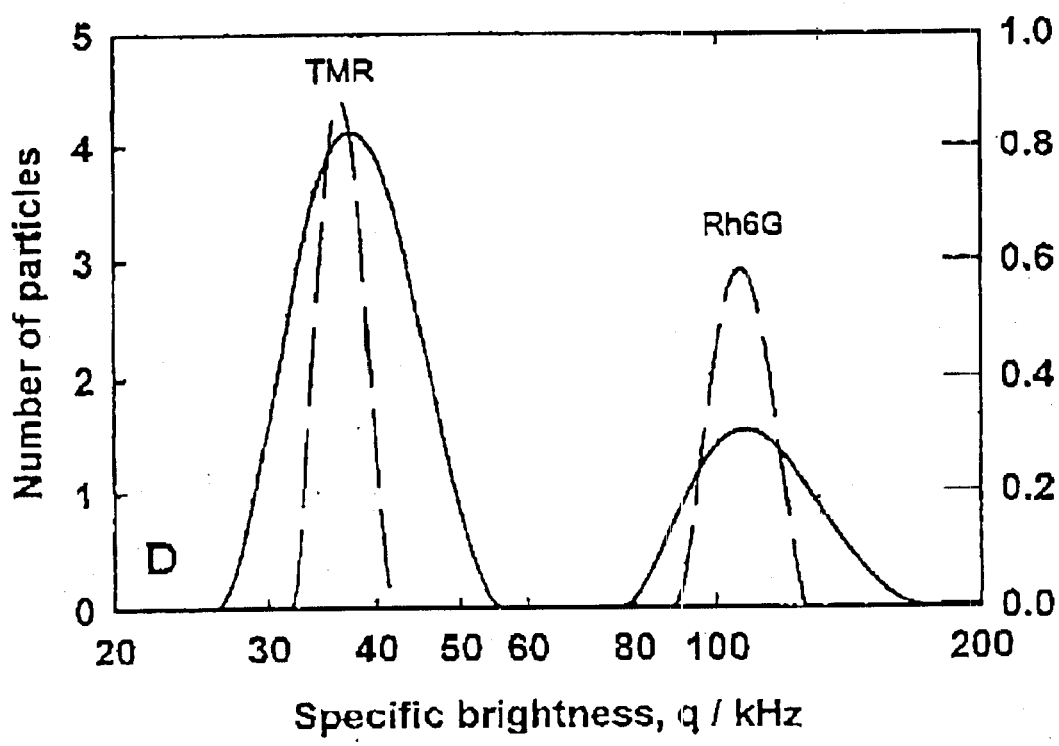

FIG. 10D shows the results of an ITR analysis (inverse transformation with the help of linear regularization and constraining concentrations to non-negative values) applied to the curves of FIG. 10B.

Figure 11:
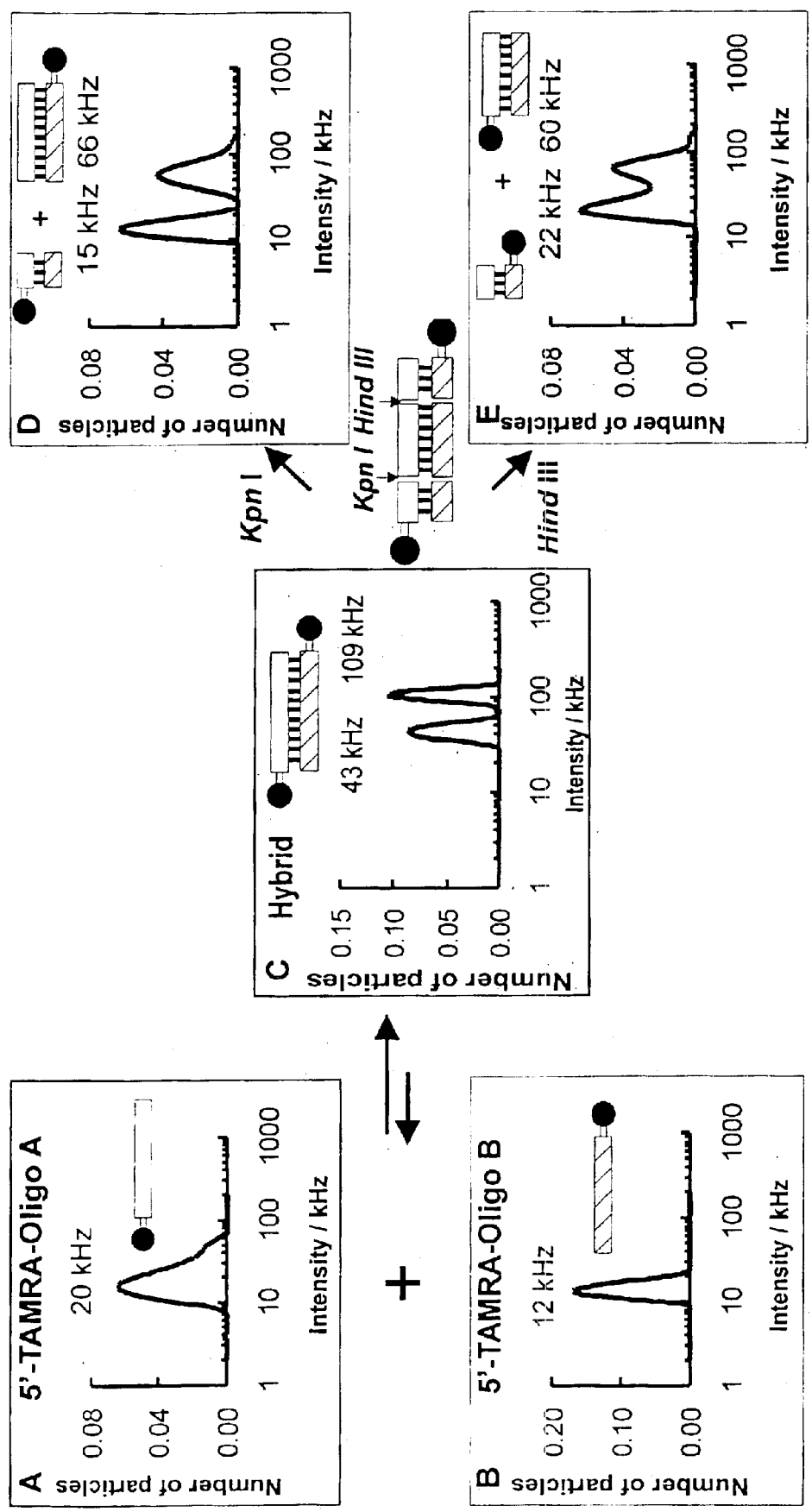

FIG. 11 shows an ITR analysis of hybridized (A–C) and restriction enzyme cleaved (D, E) labeled oligonucleotides. The curves result from a set of 20 individual 10 s measurements which show variations among each other of less than 10%.

Figure 12:
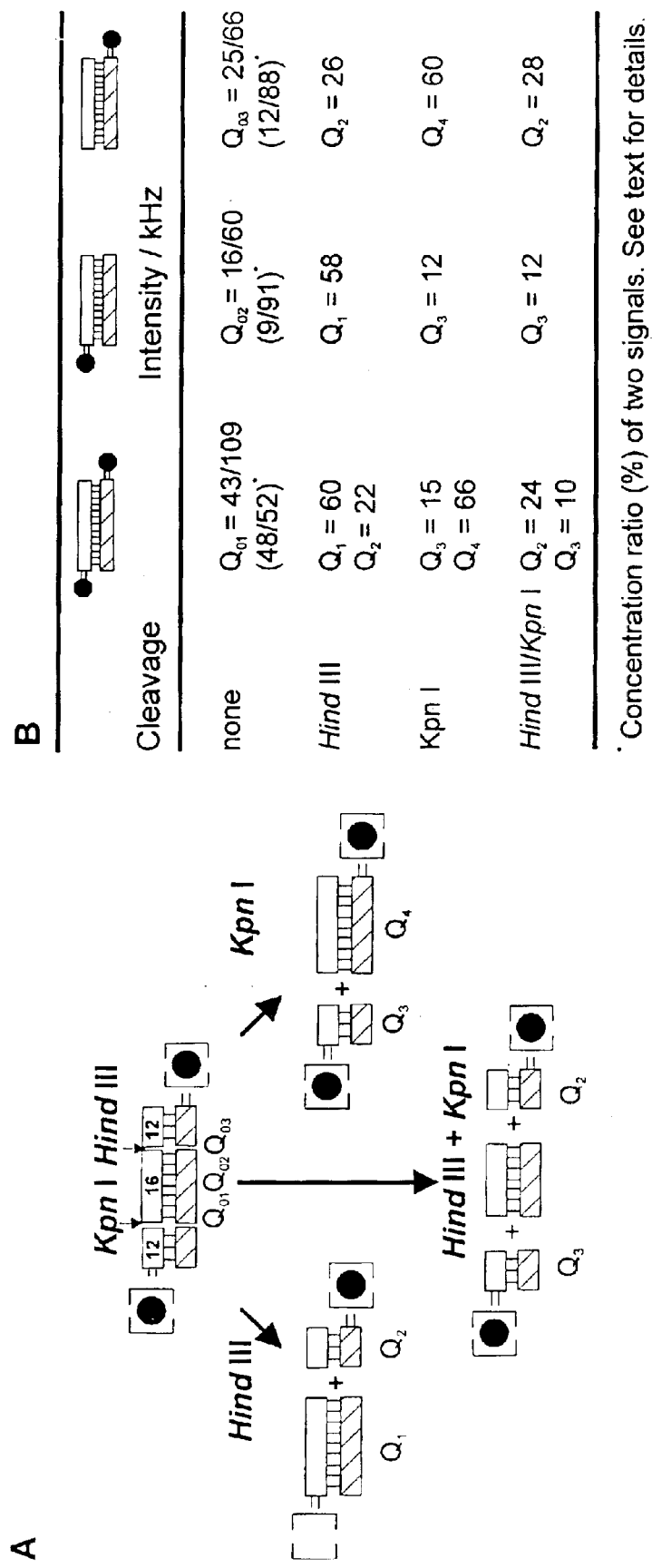

FIG. 12 illustrates hybridization and restriction enzyme cleavage of different combinations of labeled and unlabeled oligonucleotides.

Figure 13:
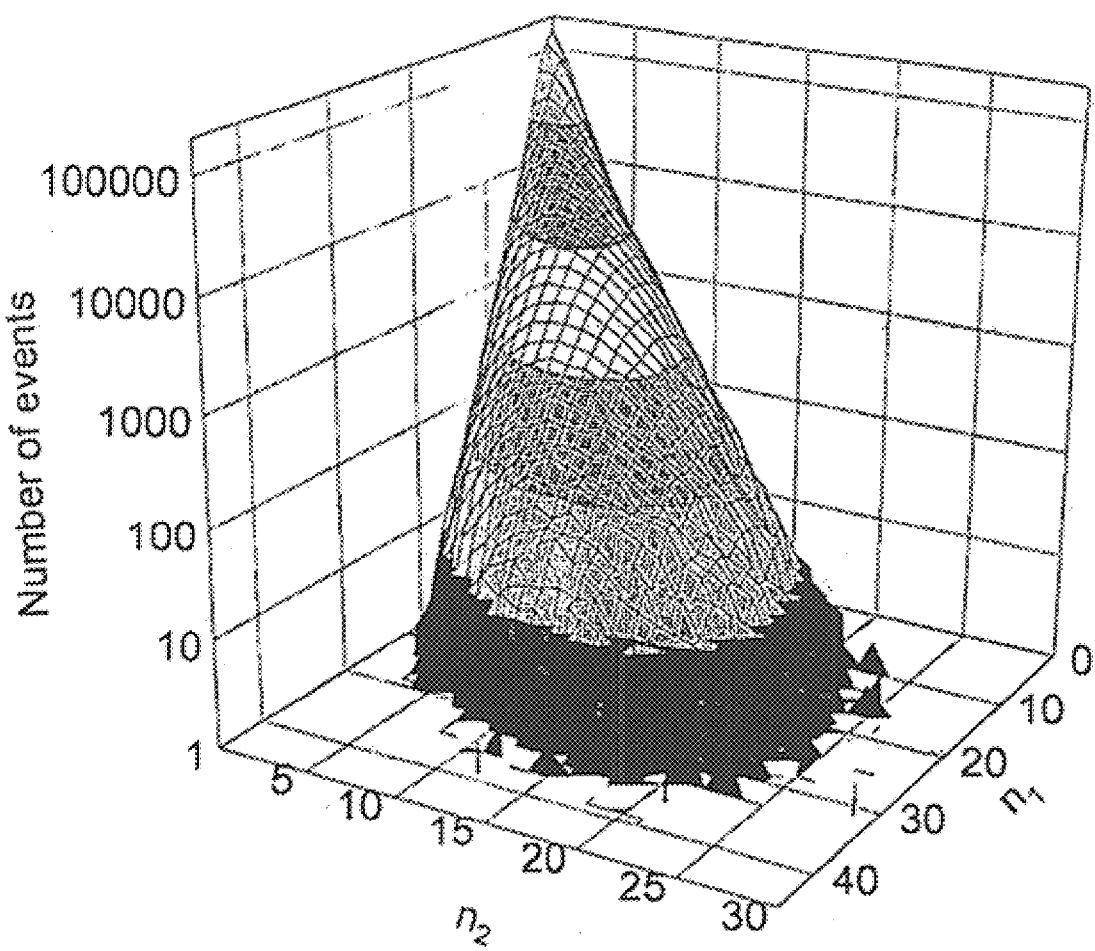

FIG. 13 is a graphical presentation of a joint histogram of the number of photon counts measured for a solution of TAMRA.

Figure 14A:
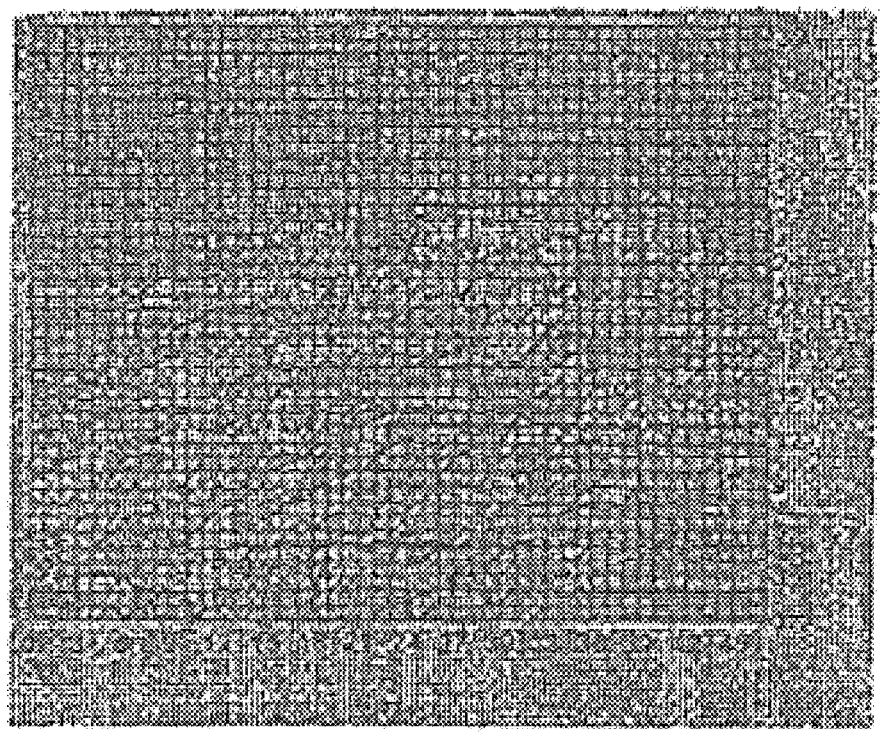
Figure 14B:
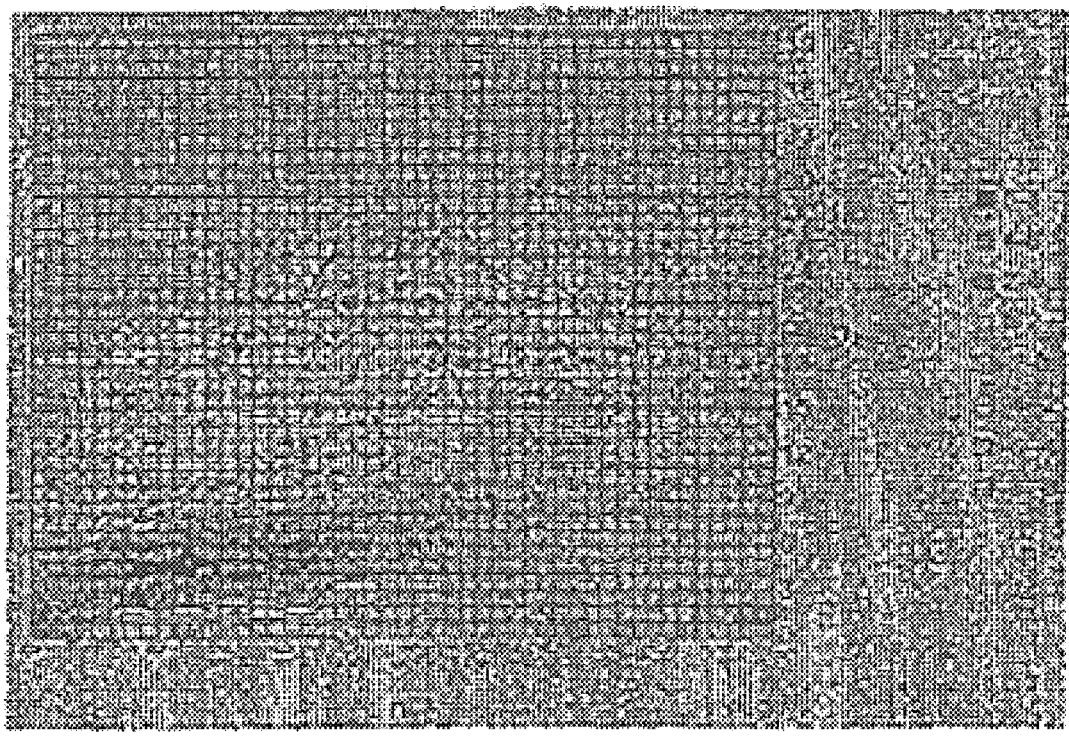

FIG. 14 is a graphical presentation of weighted residuals of a joint histogram of count numbers obtained from a mixture of TAMRA (5'-(6'-carboxytetramethylrhodamine) and RRX (rhodamine red X).

Figure 15A:
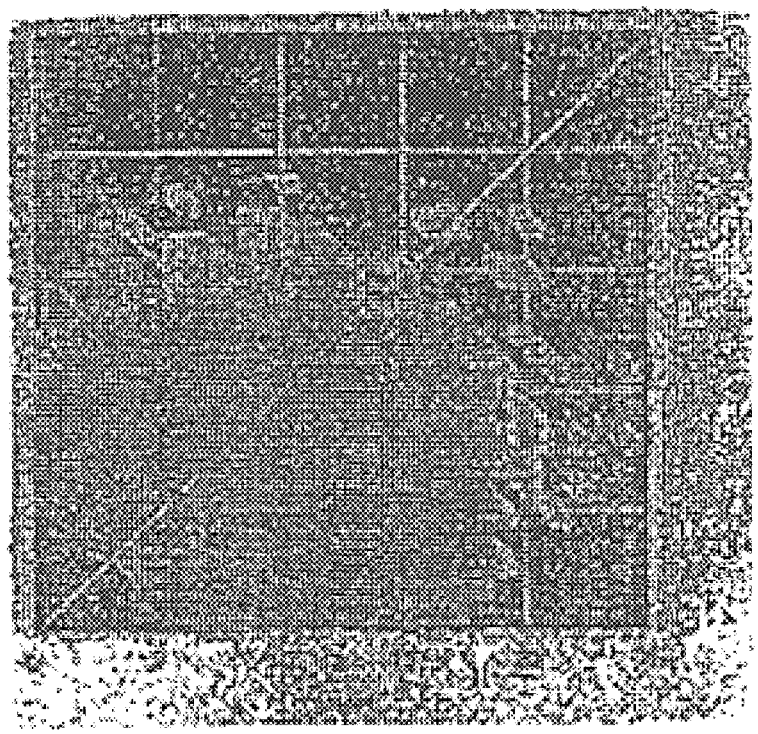
Figure 15B:
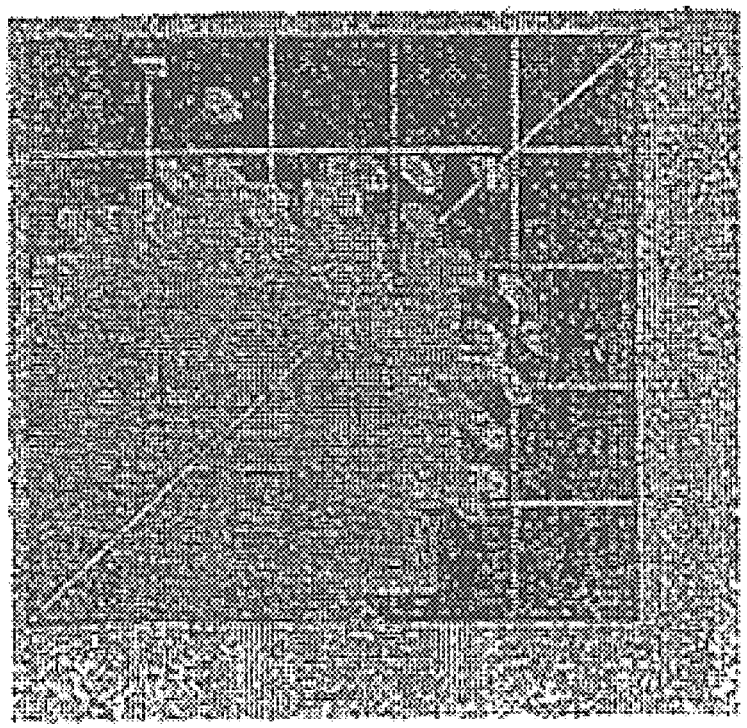

FIG. 15 illustrates joint histograms of the numbers of photon counts for the "parallel" and "perpendicular" polarization components of fluorescence measured for equal theophylline concentration of 2 nM, but different antibody concentrations.

Figure 16:
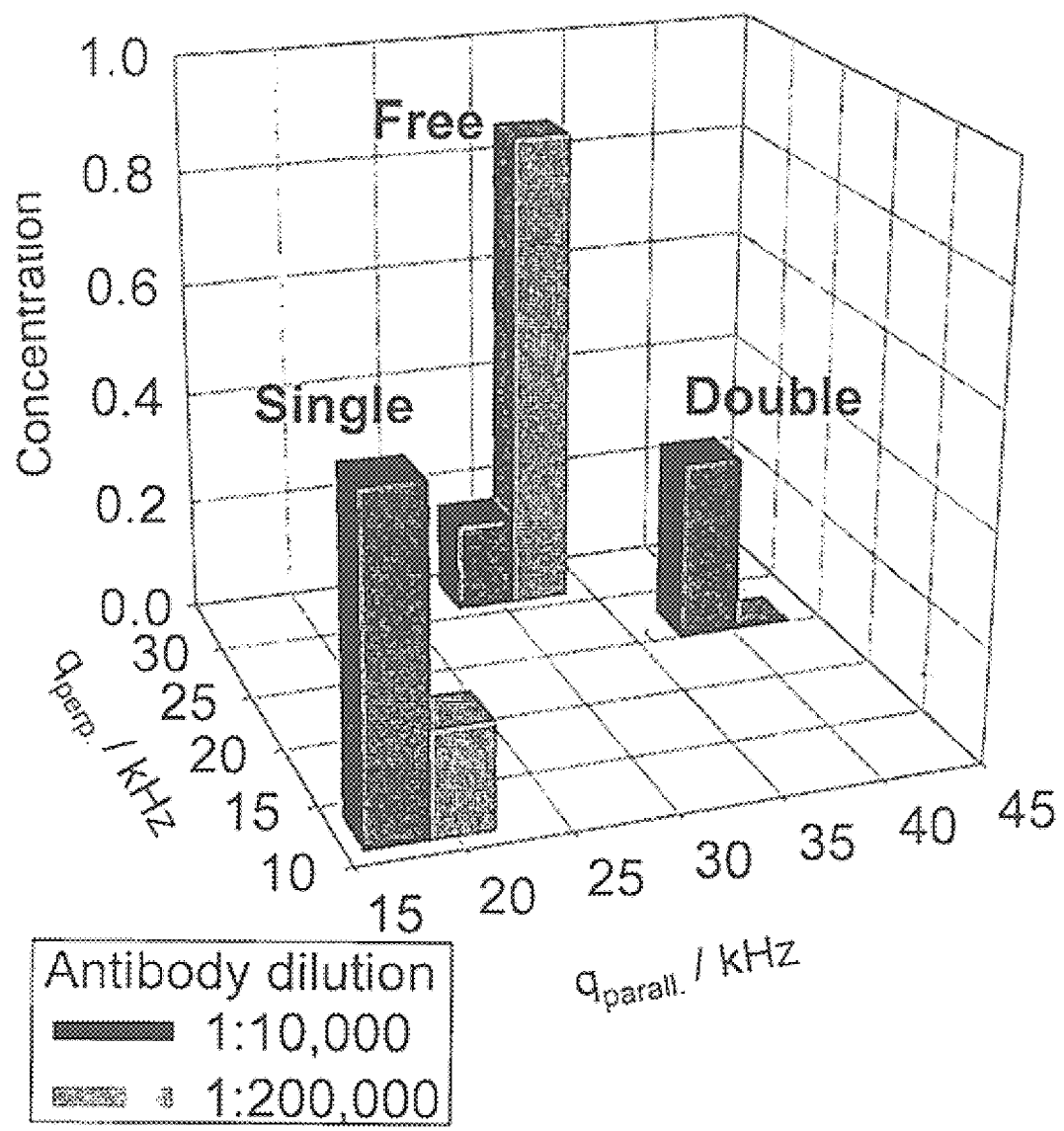

FIG. 16 illustrates the results of 2D-FIDA applied to data from samples of equal theophylline concentration, but different antibody concentration.

Figure 17:
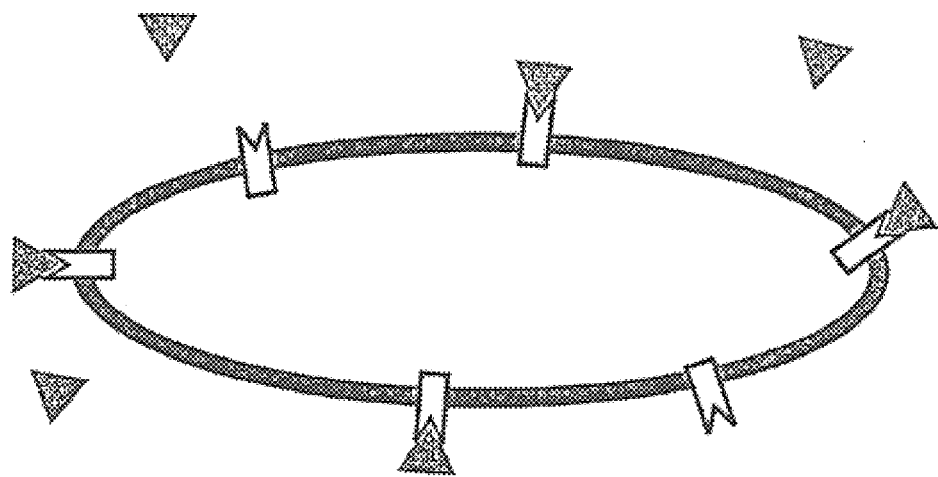

FIG. 17 illustrates the principle of a two-color 2D-FIDA experiment with multiple binding sites per vesicle.

FIG. 18 illustrates joint histograms of the numbers of photon counts in "green" and "red" measured in conditions of low (A) and high (B) degree of binding of SMS-14 (somatostatin-14) to SSTR-2 (human type-2 high-affinity somatostatin receptor).

Figure 19:
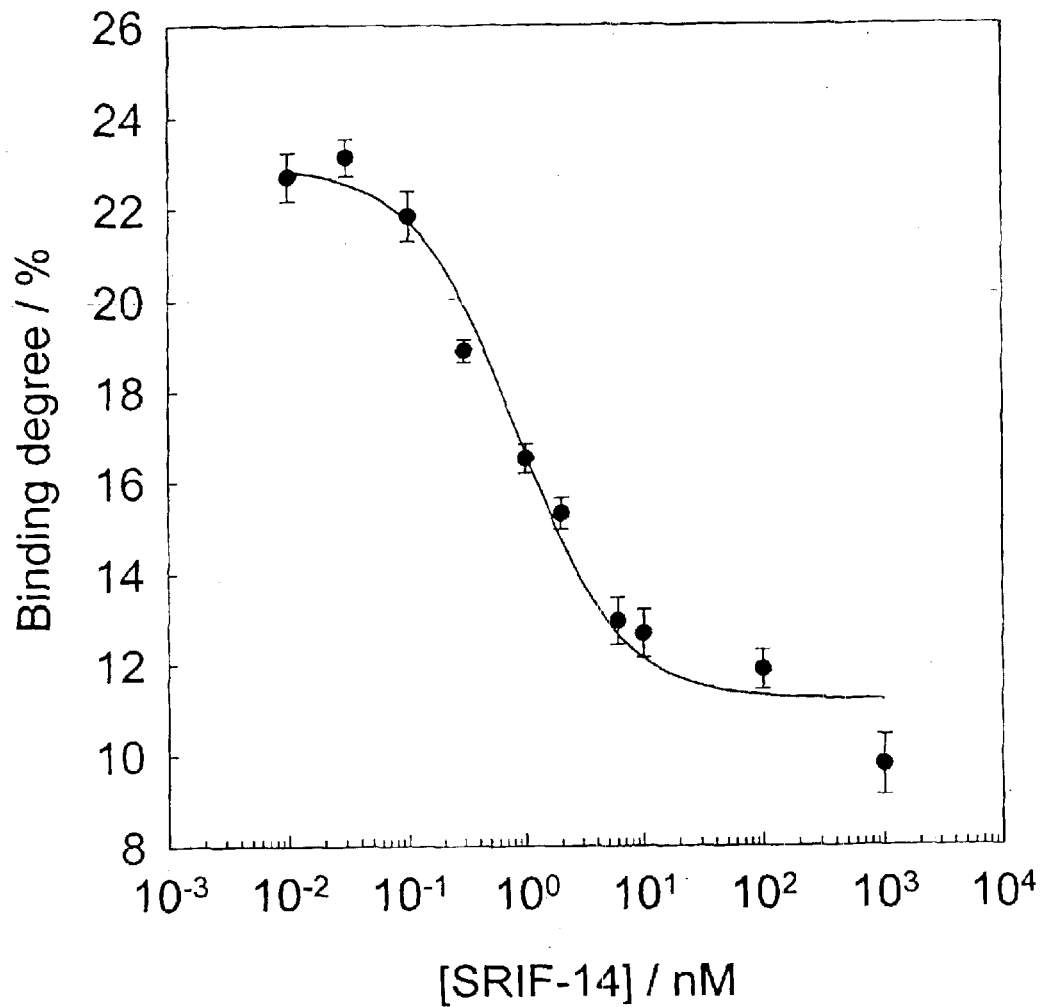

FIG. 19 shows the competition curve of the binding reaction of SMS-14 to SSTR-2.

Figure 20:
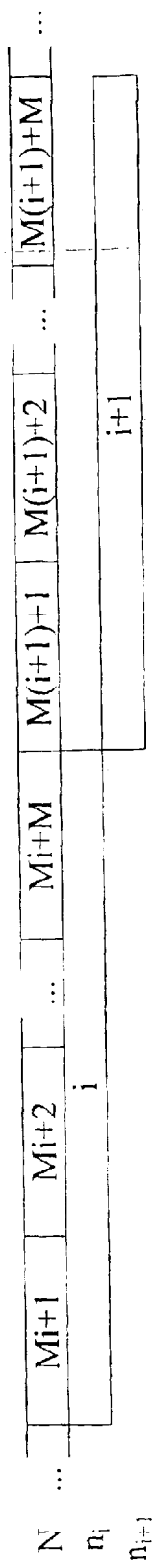

FIG. 20 illustrates an embodiment in which numbers of photon counts $\{n_i\}$ subject to determination of a histogram $\tilde{P}(n)$ in step b) are derived from numbers of photon counts in primary time intervals $\{N_j\}$ by summing up numbers of photon counts from primary time intervals according to a predetermined rule.

Figure 21:
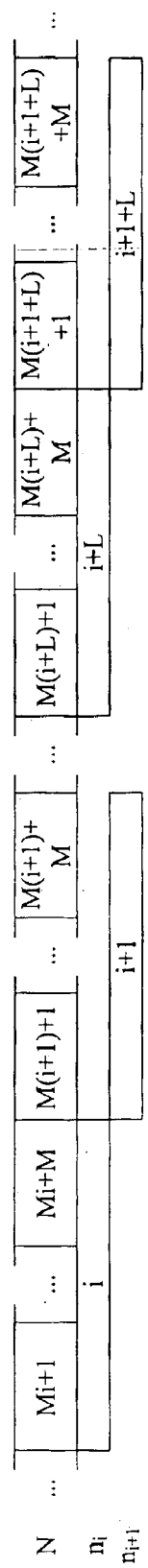

FIG. 21 illustrates a further embodiment in which numbers of photon counts $\{n_i\}$ are derived from predetermined primary time intervals according to a rule in which primary time intervals are separated by a time delay.

Figure 22:
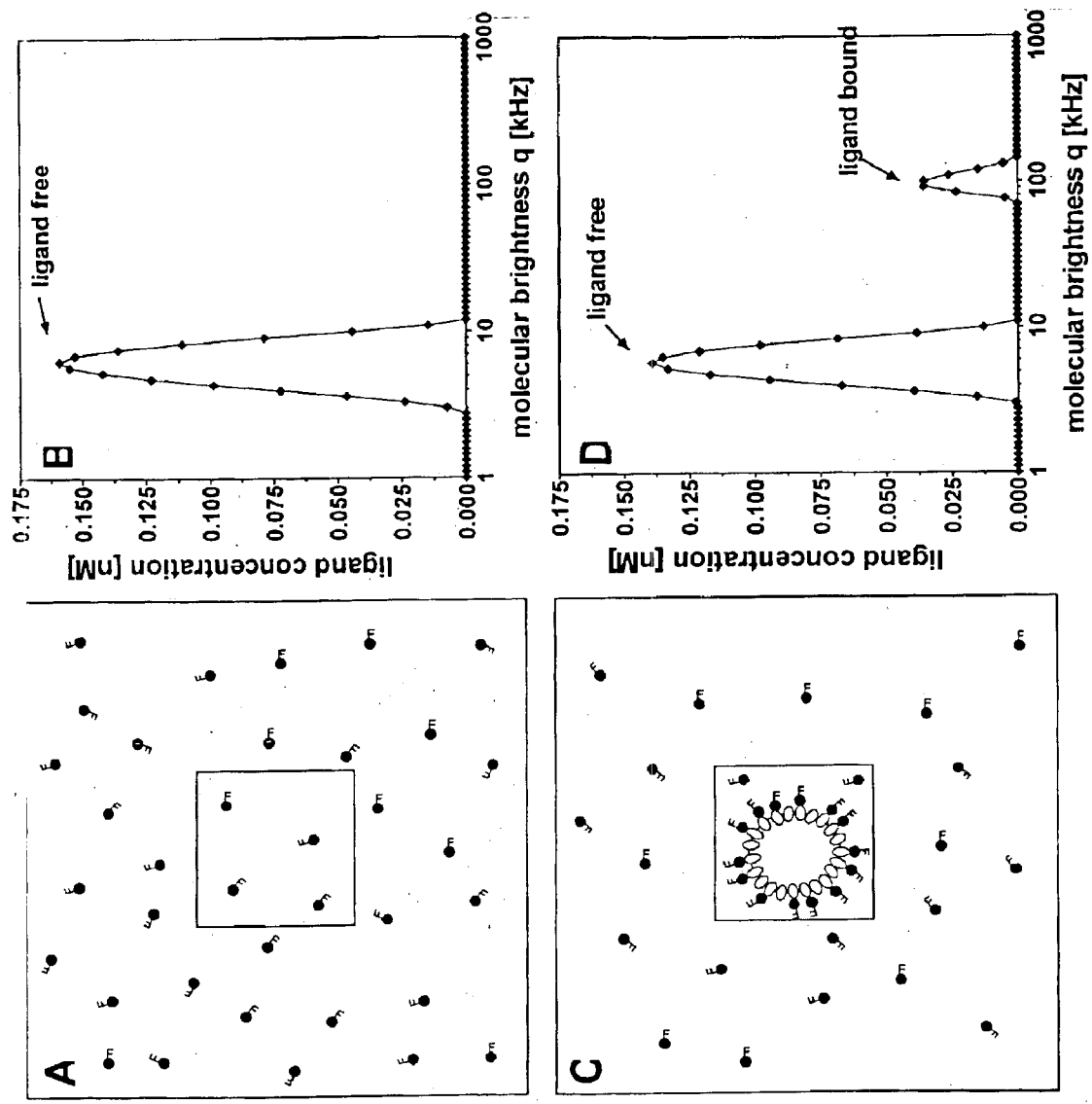

FIG. 22 shows a schematic diagram of binding of a fluorescently-labelled molecule to receptor-bearing vesicles as observed utilizing the present invention.

Figure 23:
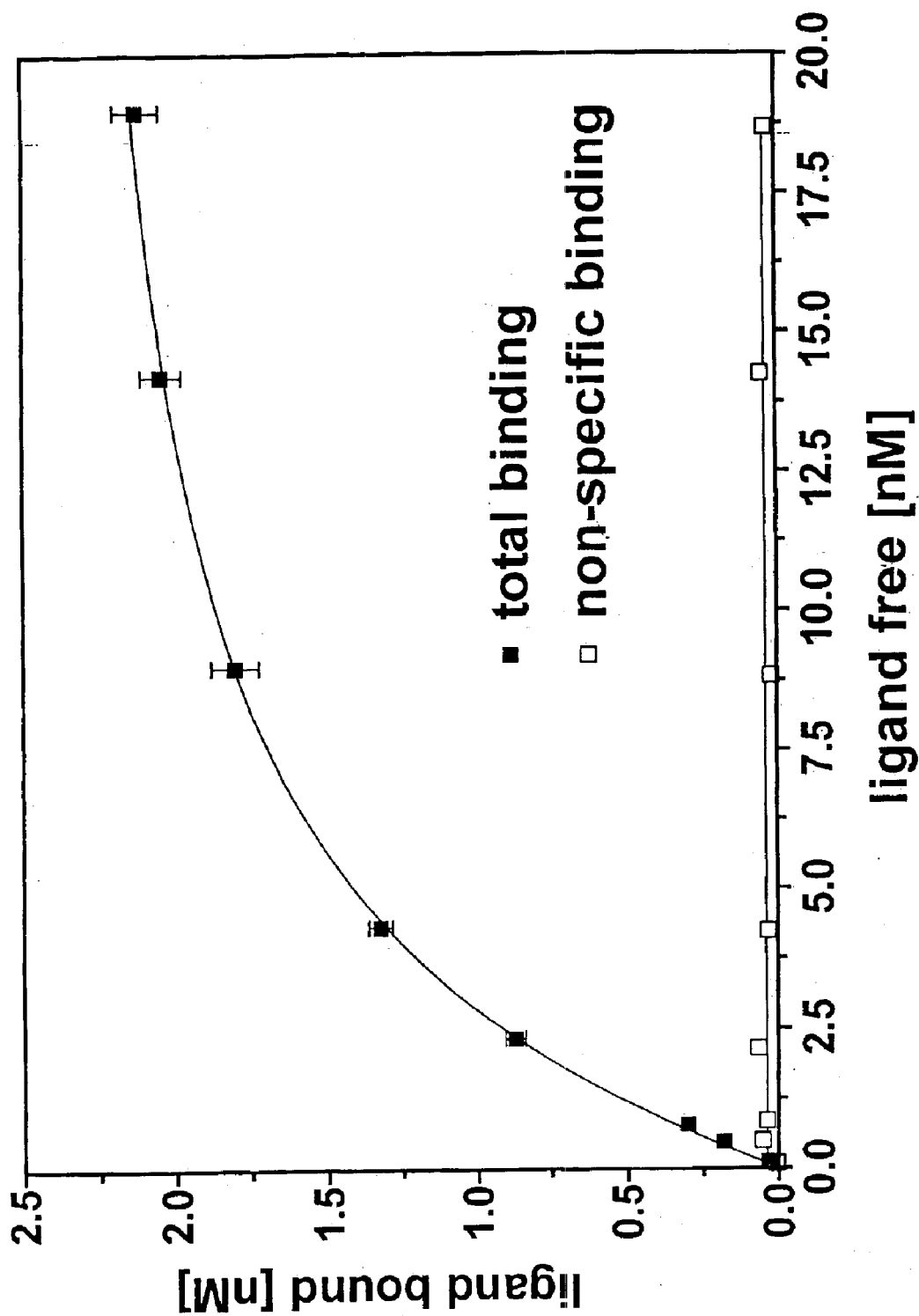

FIG. 23 illustrates the ligand binding characteristics of TMR-EGF to membranes prepared from A431 cells.

Figure 24:
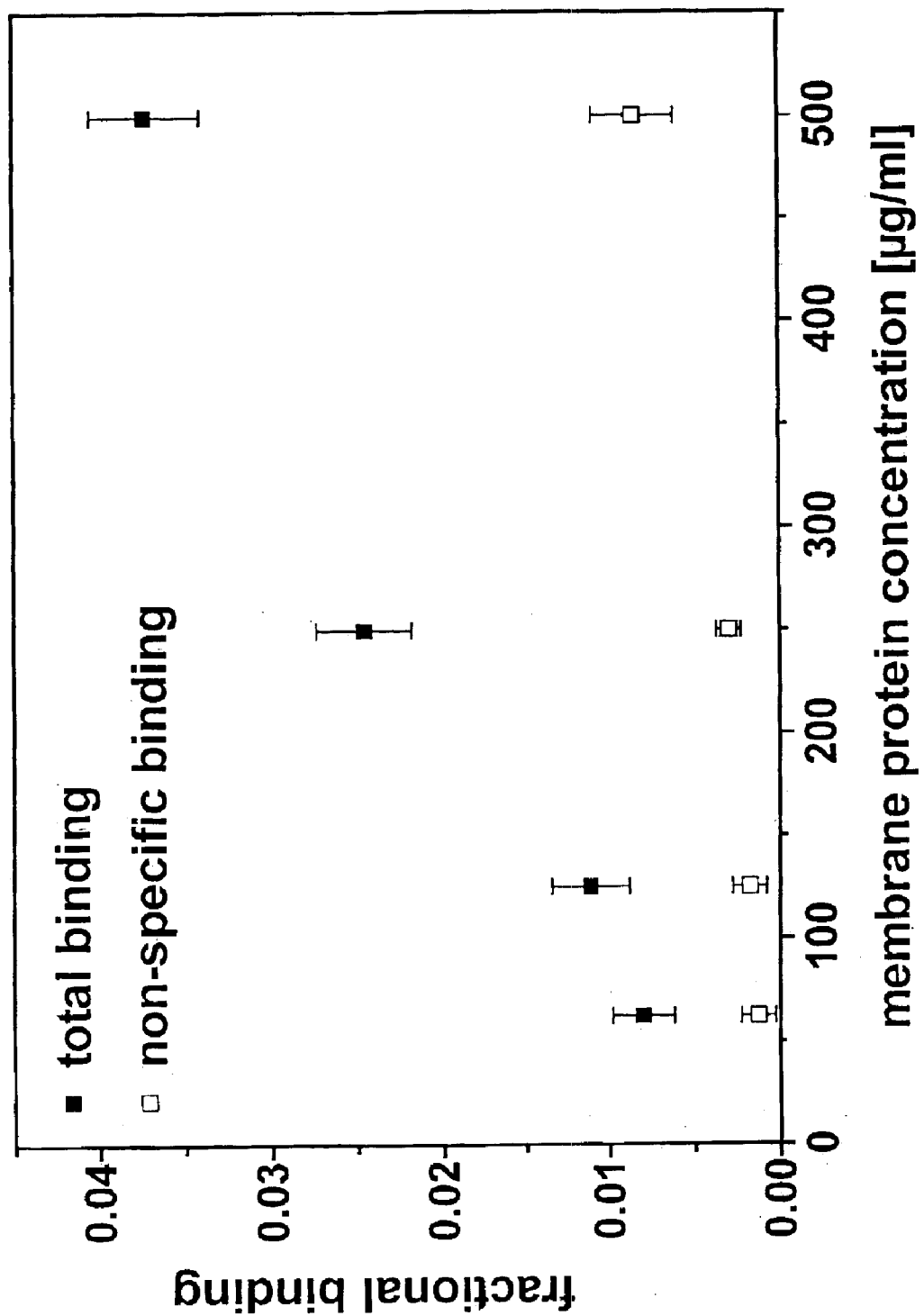

FIG. 24 shows the binding of TMR-EGF to membranes prepared from HCT cells.

Figure 25:
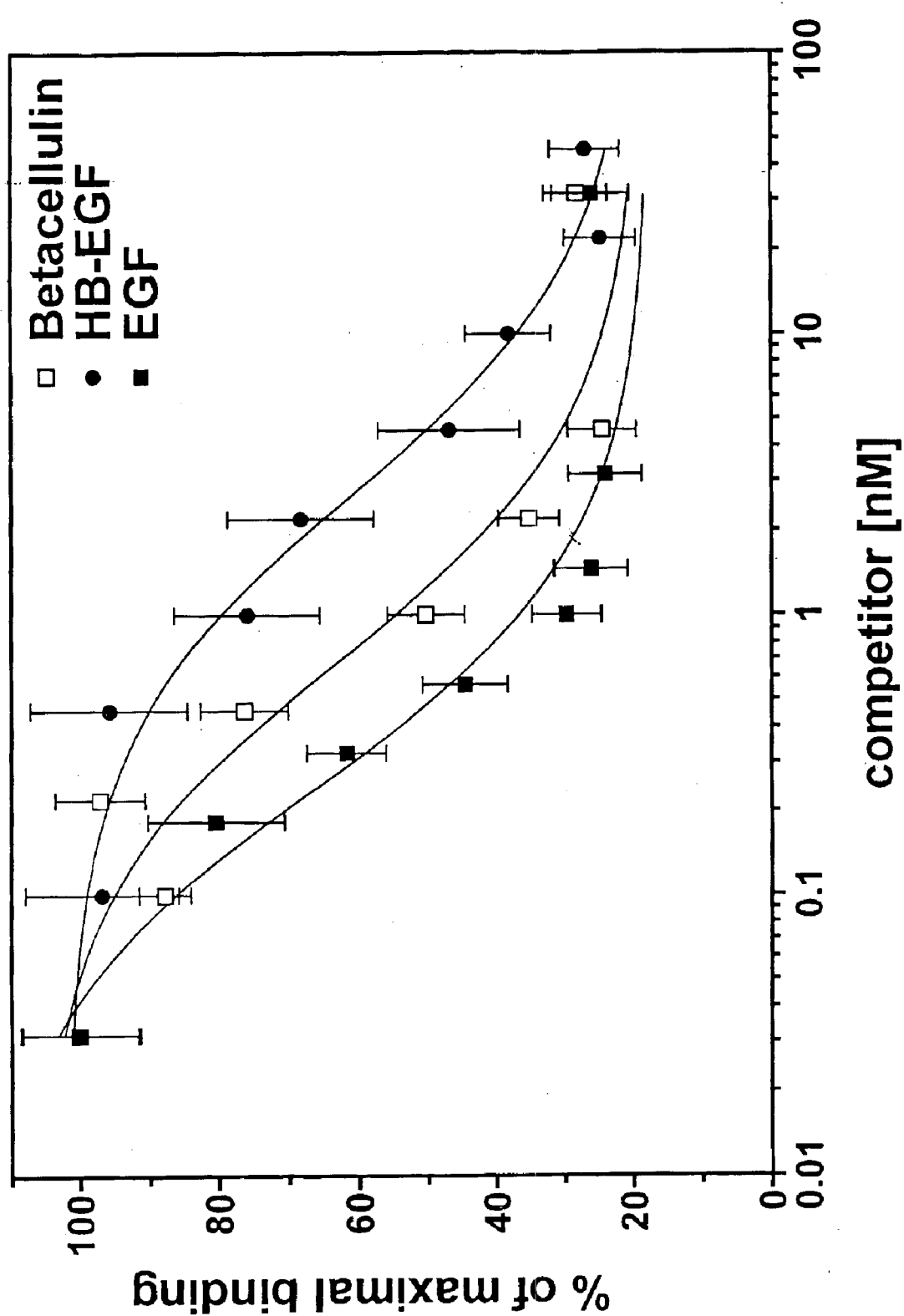

FIG. 25 illustrates the pharmacological profile of the EGF receptor.

Figure 26:
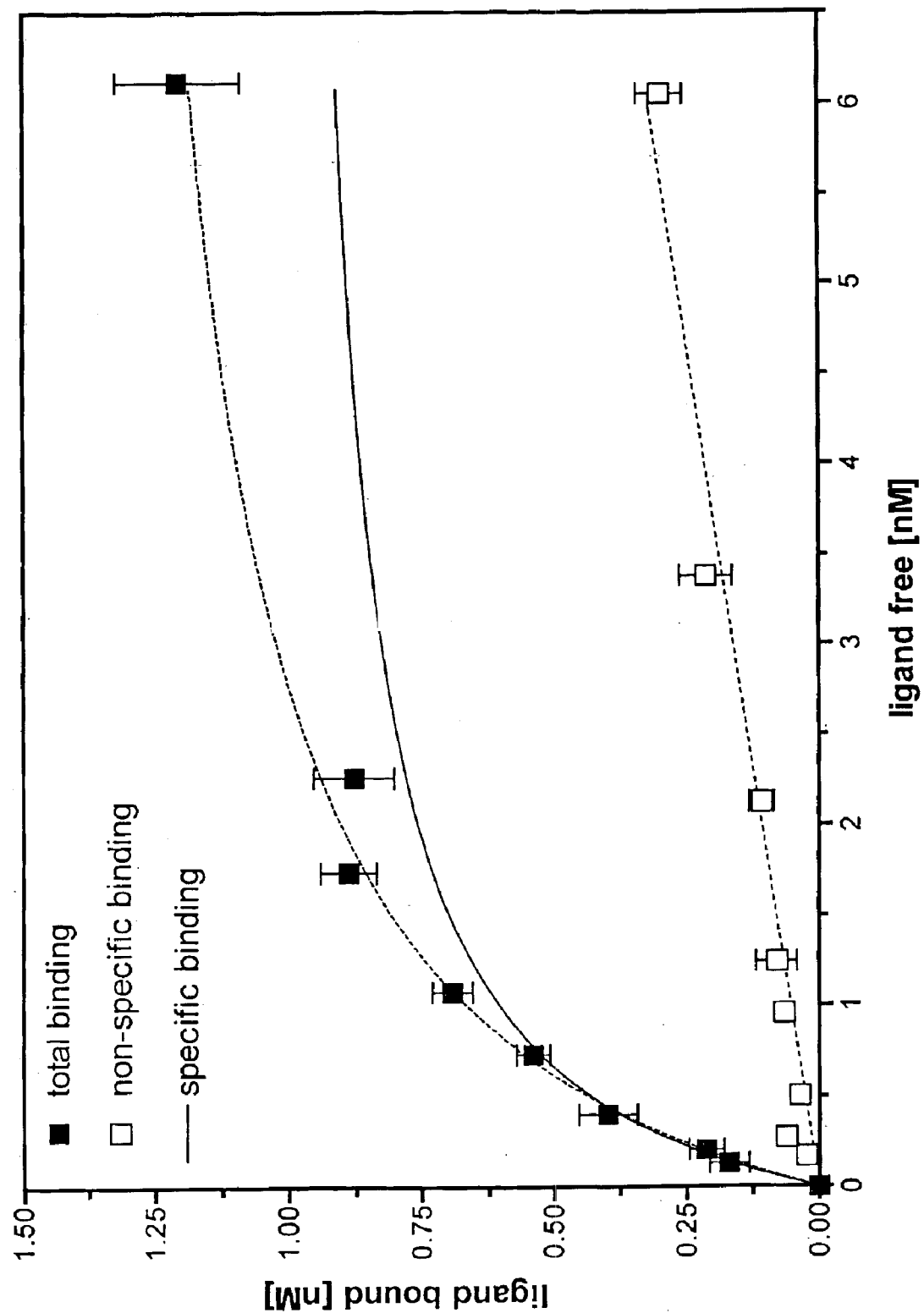

FIG. 26 illustrates the ligand binding characteristics of Bodipy FL-CGP 12177.

Figure 27:
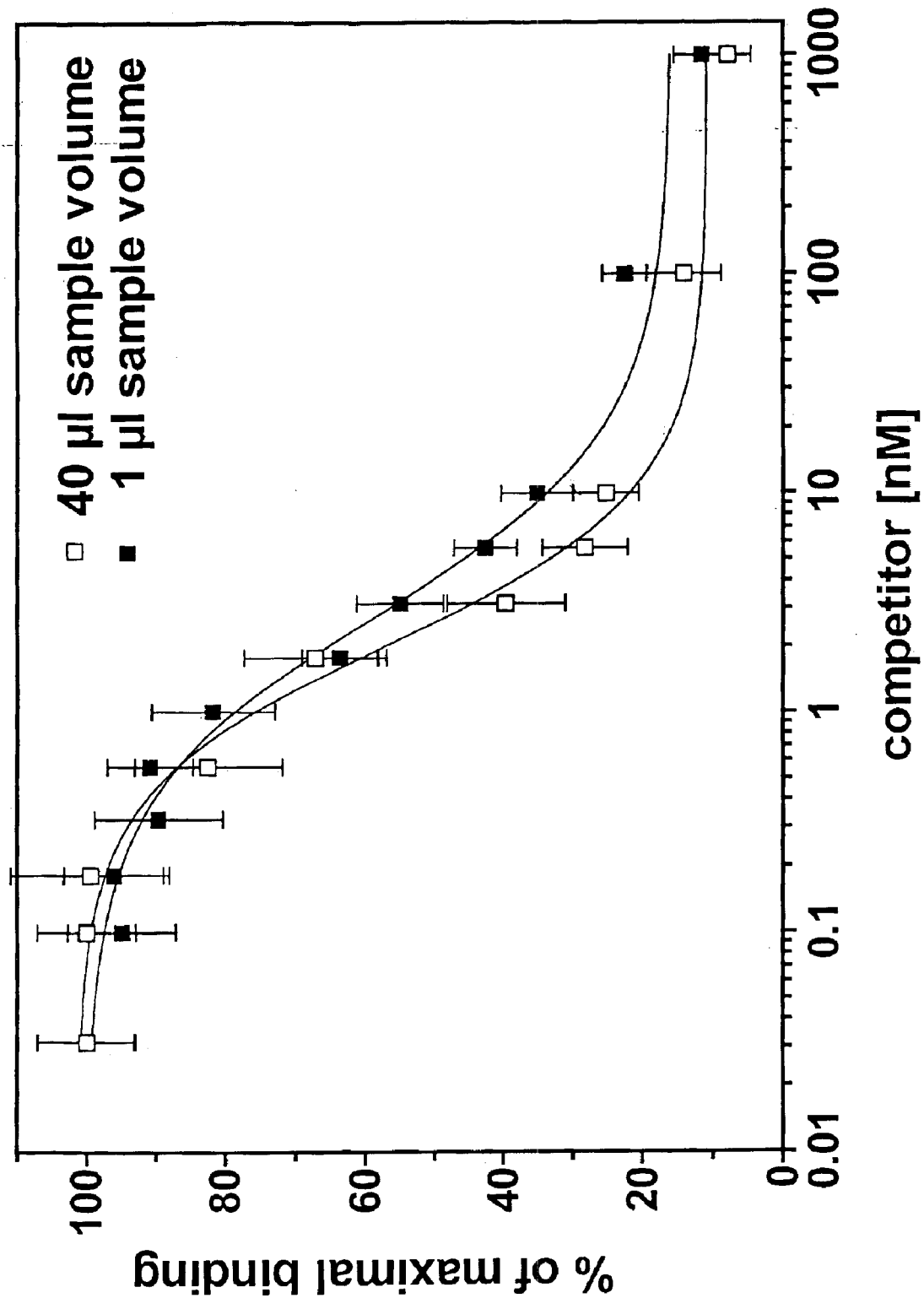

FIG. 27 shows the inhibition of Bodipy FL-CGP 12177 binding in 40 $\mu$l and 1 $\mu$l assay volumes.

Figure 28:
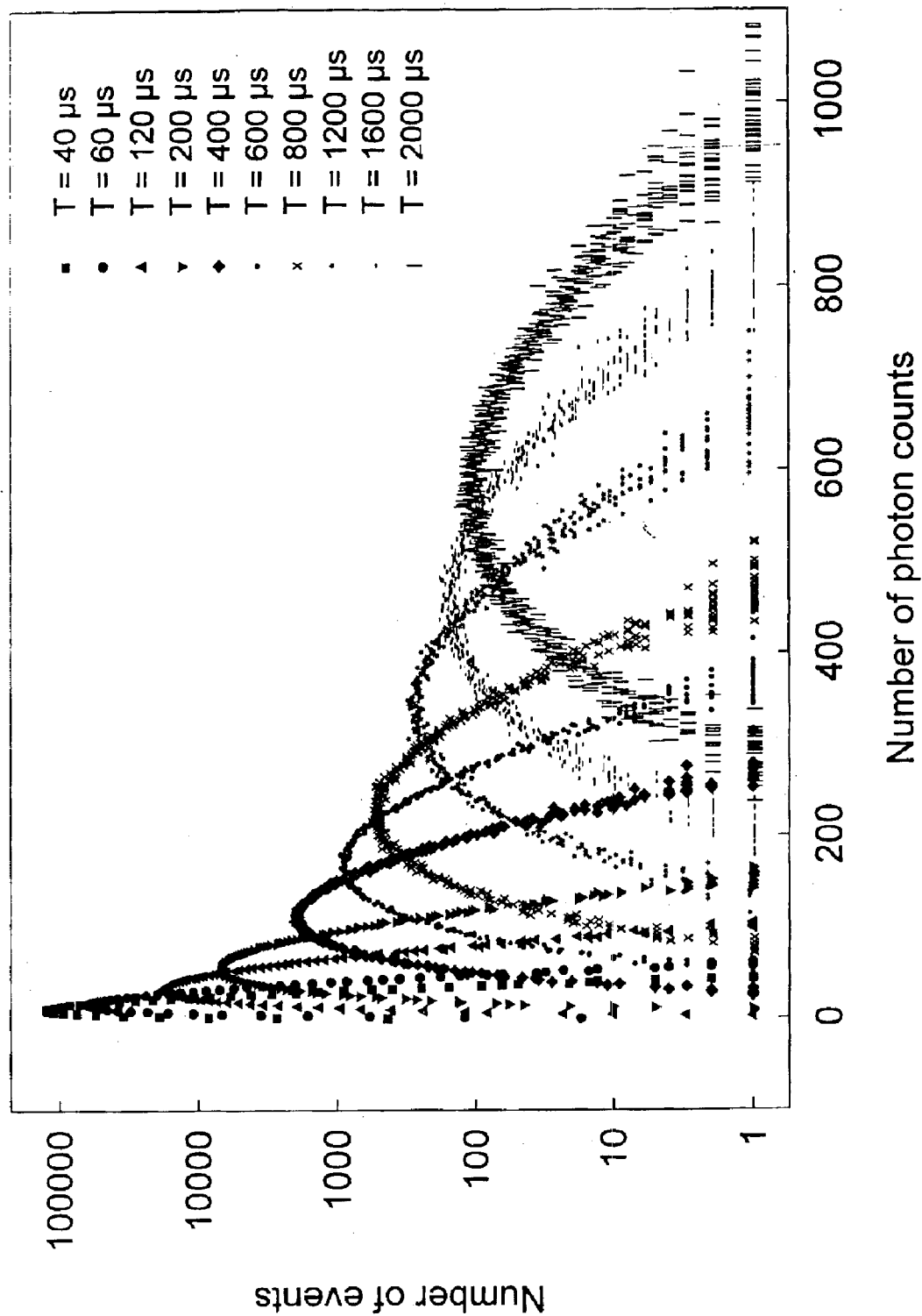

FIG. 28 illustrates the count number histograms of a 0.8 nM Cy5 solution recorded at different time windows T.

Figure 29:
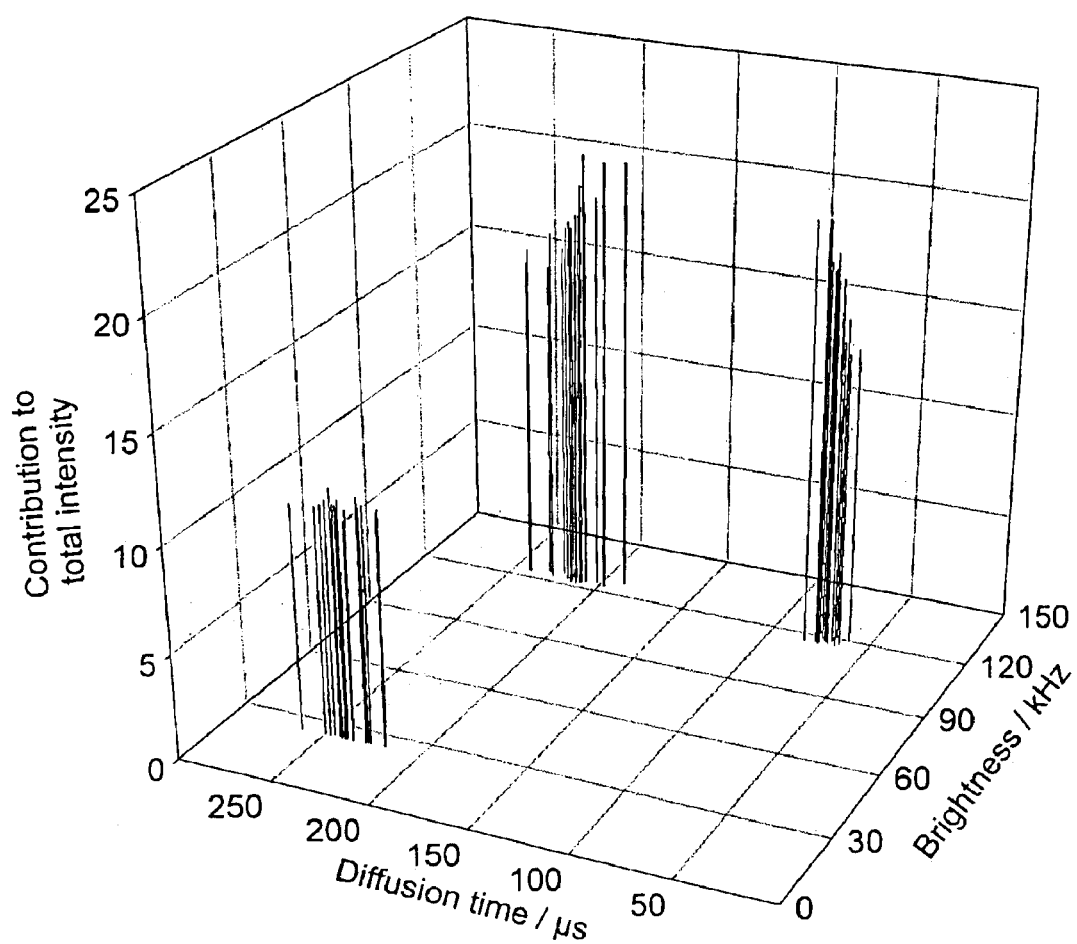

FIG. 29 shows the fitting results of simulated data for a mixture of 3 components. The simulated brightness (in kHz) and diffusion time (in $\mu$s) values for the components are: (30 kHz, 192 $\mu$s); (120 kHz, 192 $\mu$s); (120 kHz, 64 $\mu$s). The contributions to the total intensity are 10.8, 20.4, and 14.4, respectively. The graph presents the results of FIMDA from 20 independent realizations of simulations, each corresponding to an experiment of 60 s duration.

Figure 30:
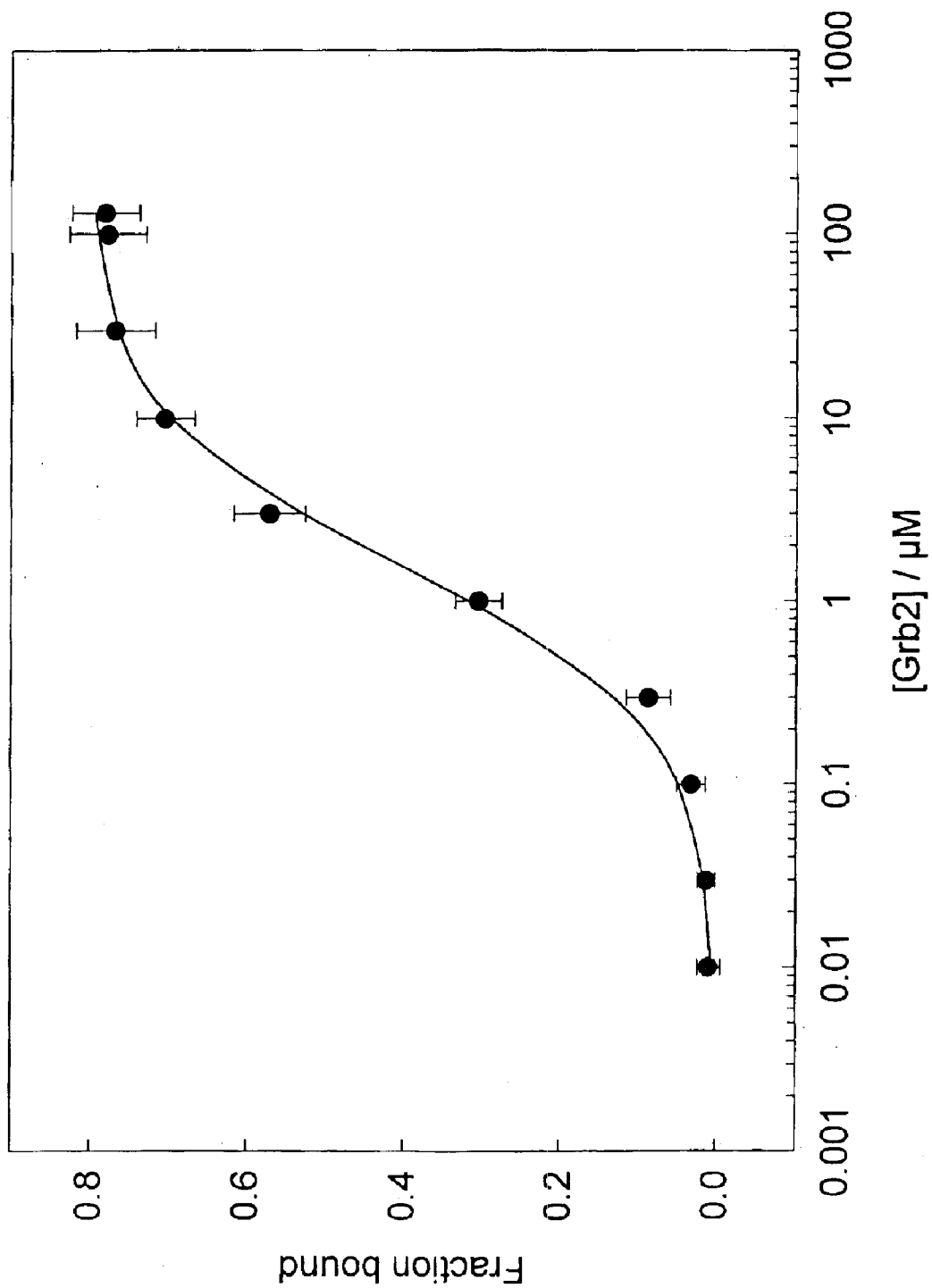

FIG. 30 illustrates the binding of pTyr-Val-Asn-Val-Lys (Cy5) to SH2. The solid curve results from a hyperbolic fit, yielding a binding constant of $K_D$=1.68±0.27 $\mu$M.

Figure 31:
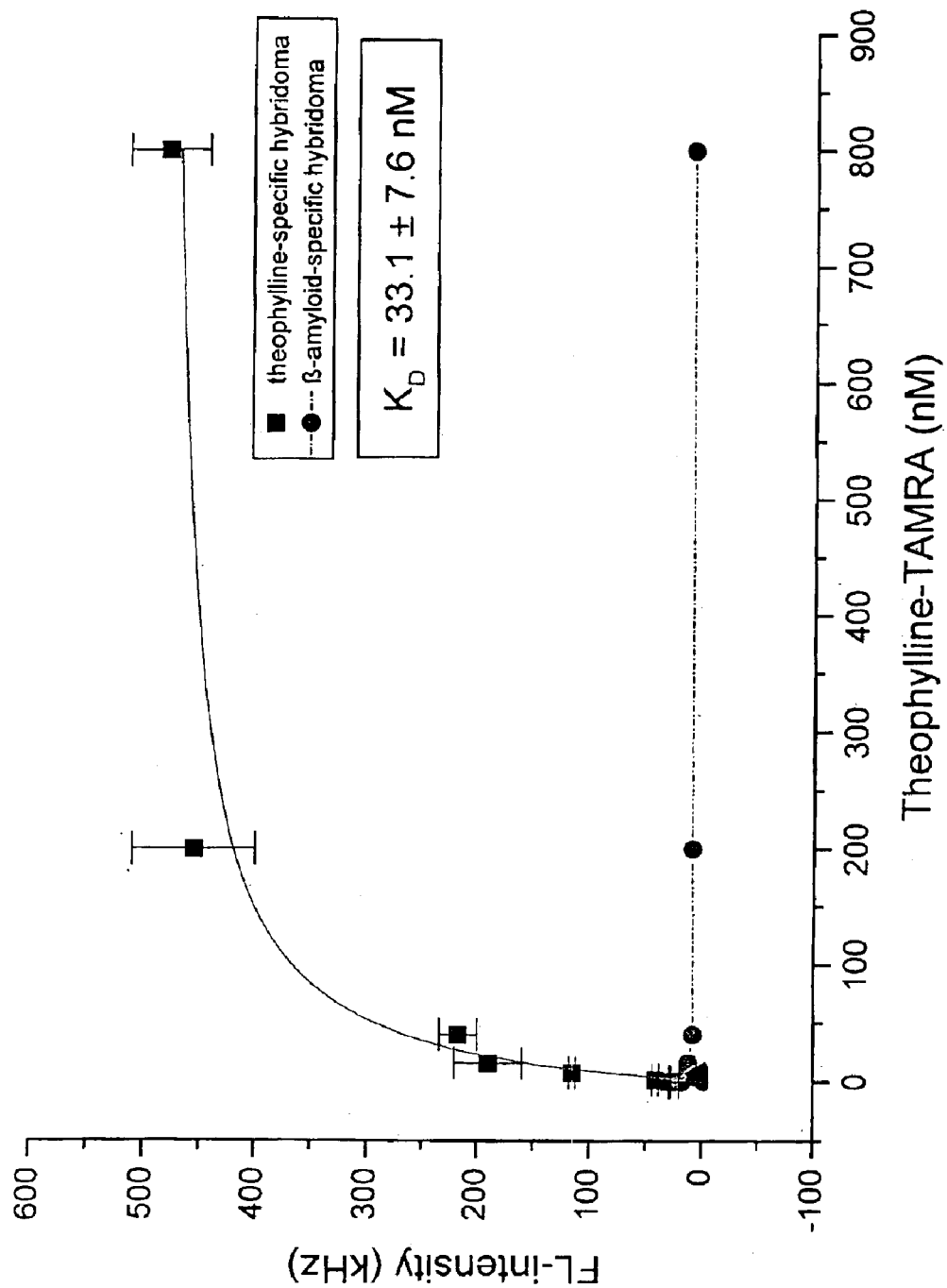

FIG. 31 illustrates the measurement of the binding constant ($K_D$) of monoclonal antibody exposed on the surface of the theophylline-specific hybridoma cell line HB-8152.

Figure 32:
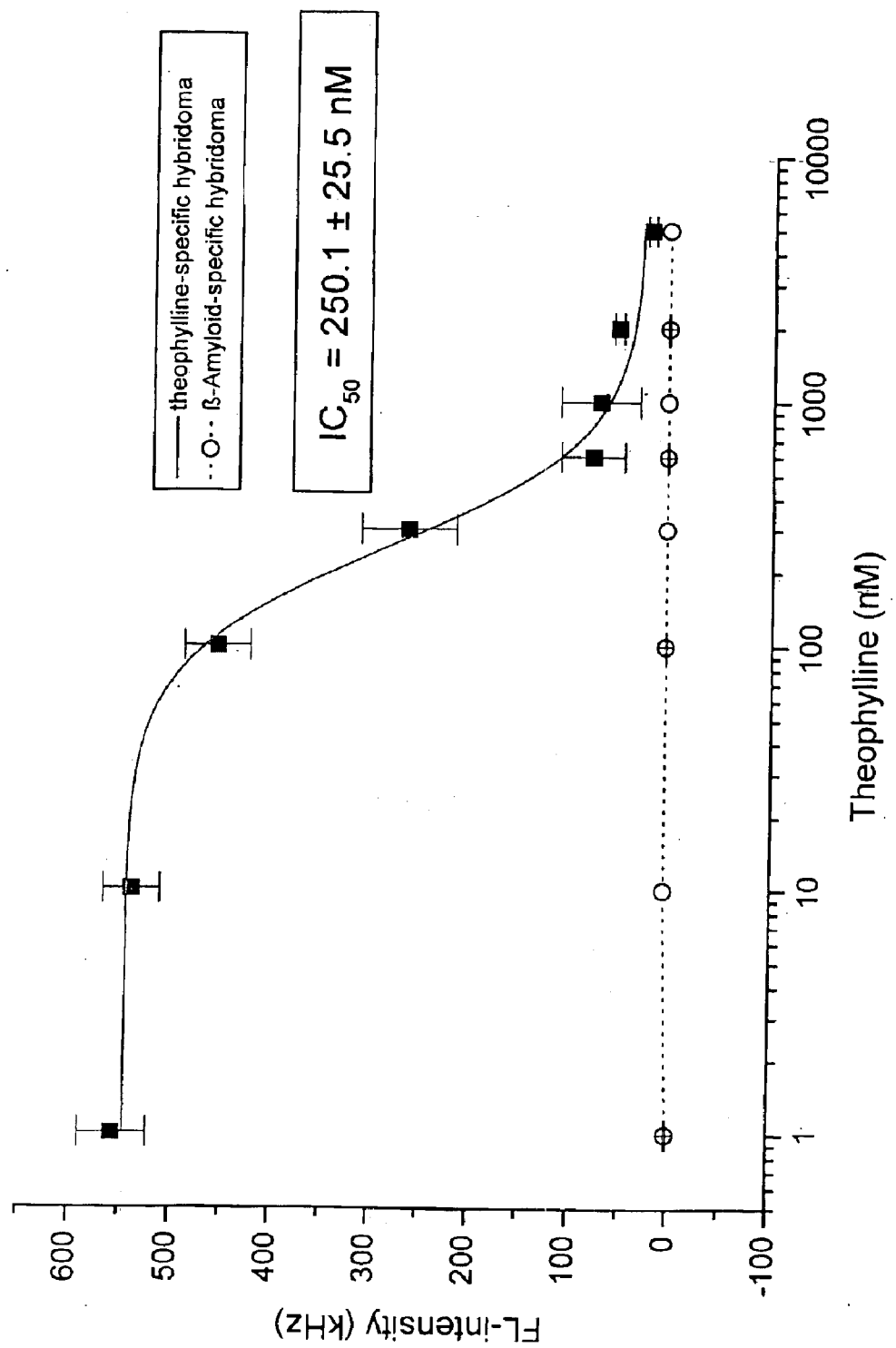

FIG. 32 illustrates the $IC_{50}$ measurement of the specific binding of theophylline-TAMRA to monoclonal antibody exposed on the surface of hybridoma cell line HB-8152.

Figure 33:
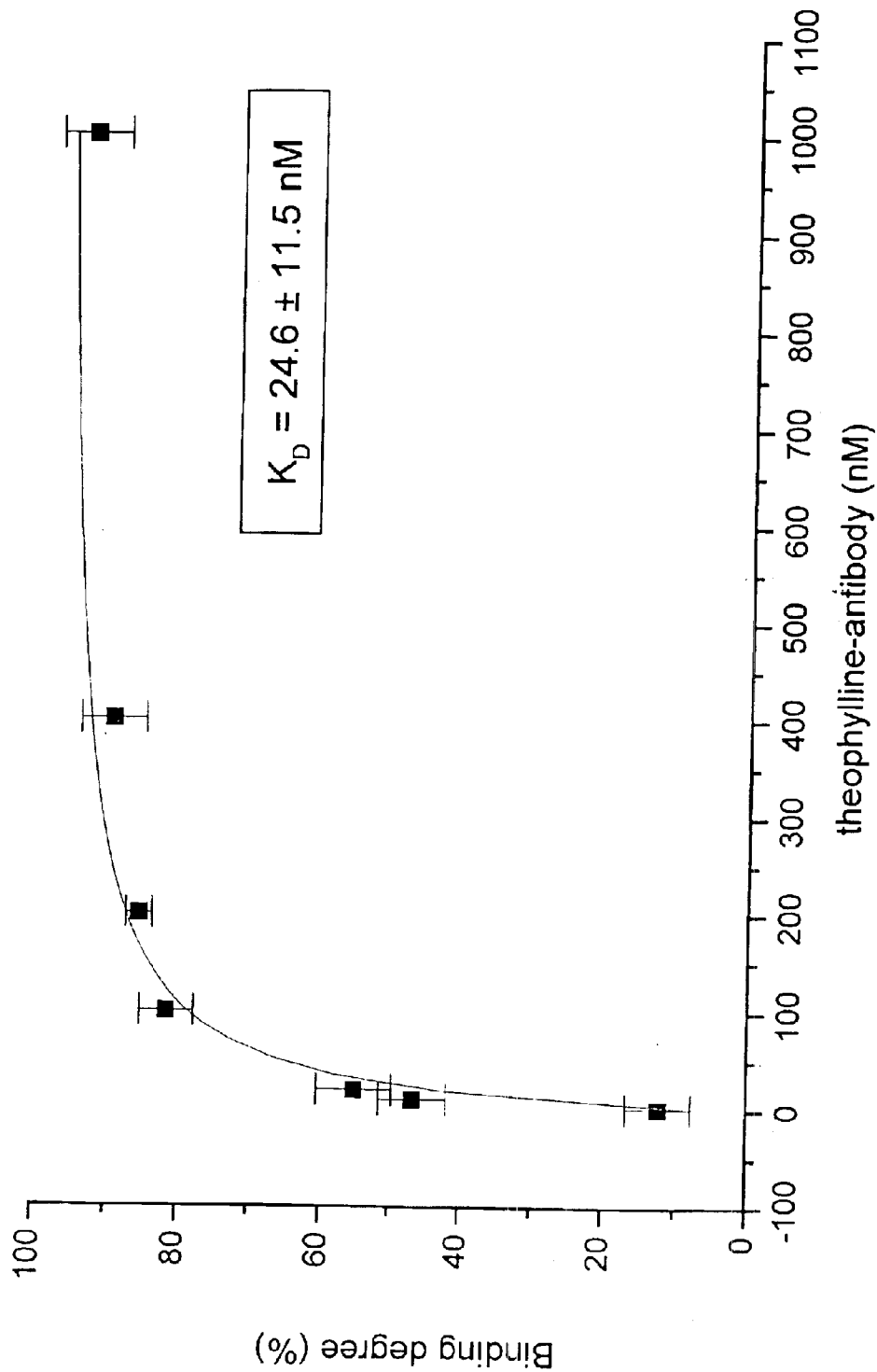

FIG. 33 illustrates the measurement of the affinity constant of soluble monoclonal antibody purified from the culture medium of theophylline-specific hybridoma cell line HB-8152.

DETAILED DESCRIPTION OF FIGURES

FIG. 1

Figure 1A:
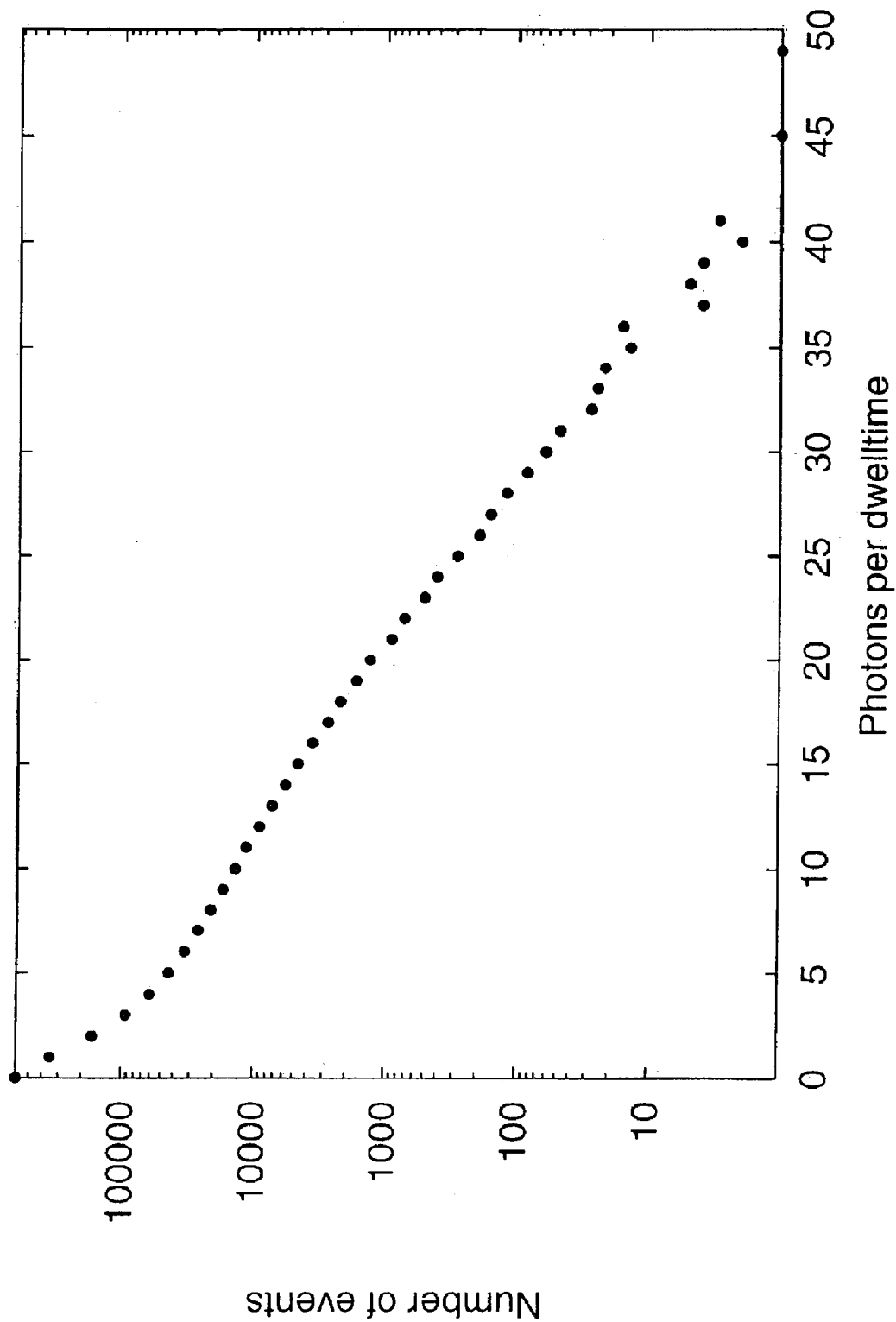
FIG. 1 shows a count number histogram obtained for a solution of the dye tetramethylrhodamine (a) and residual curves corresponding to different fitting procedures (b).
Figure 1B:
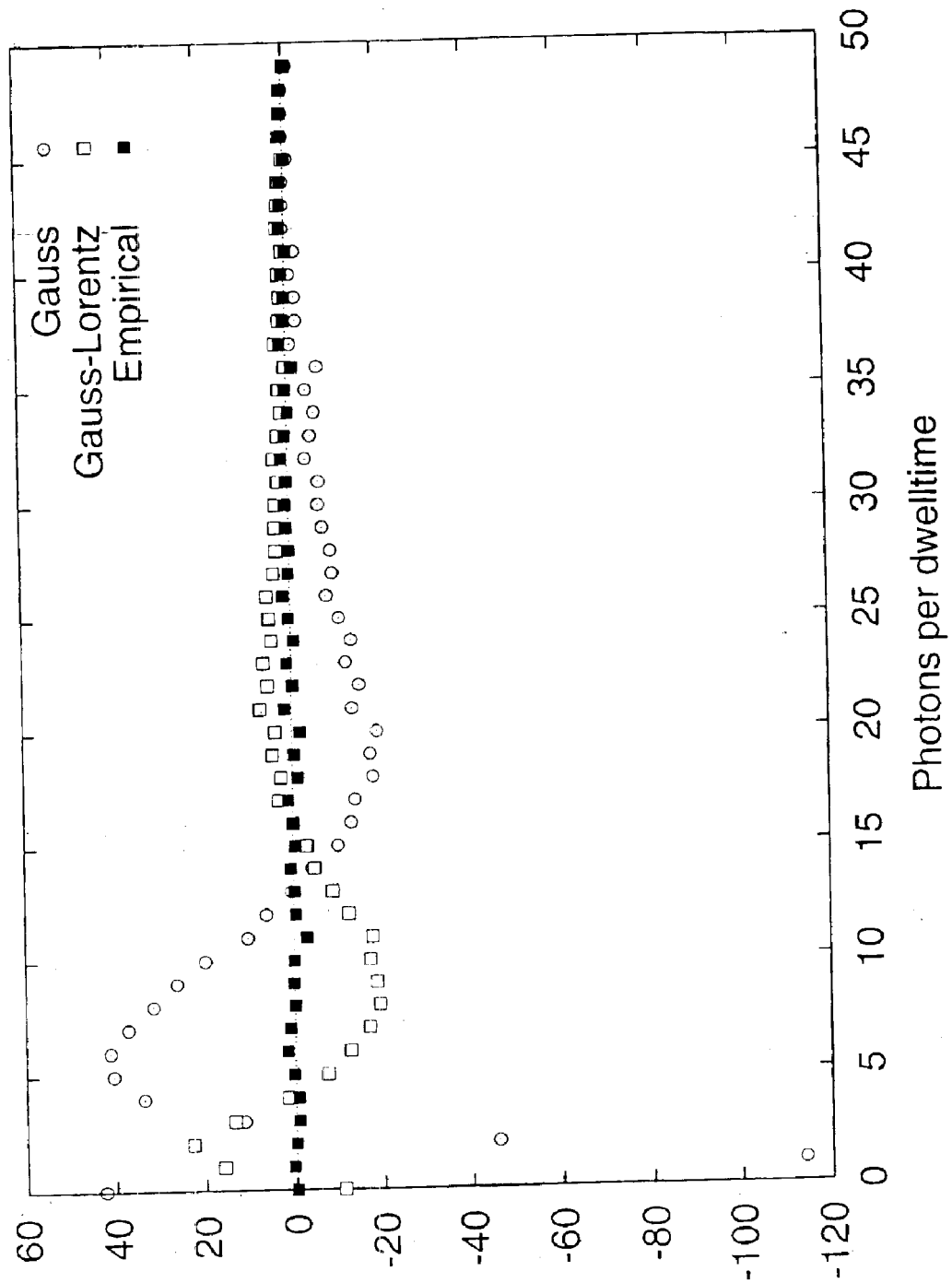

Reference is now made to FIG. 1 which shows a count number histogram obtained for a solution of the dye tetramethylrhodamine (a) and three residuals curves corresponding to the best fit obtained with Eqs (36), (37), and (38) below (b). The concentration of the aqueous tetramethylrhodamine solution was about $10^{-9}$ M. Primary time intervals were 40 $\mu$s. The data collection time was 60 s. This 1D-FIDA experiment illustrates the importance of using a sufficiently flexible model of the brightness profile. This is important in 2D-FIDA, FIMDA and FACID as well.

The most widely used spatial profile model in FCS is the three-dimensional Gaussian profile with a single parameter of shape, the axial dimension ratio in longitudinal and radial directions. Residuals curve with open circles illustrates the fit quality obtainable with the Gaussian profile. There are large systematic deviations in residuals. What is a sufficiently flexible model for fitting FCS data has turned out to be a rather inflexible and inadequate model for FIDA.

A model of the sample profile which has yielded a better fit of the histogram $\hat{P}(n)$ is Gaussian-Lorentzian (open squares), but this model still lacks flexibility. According to Eq. (8), a certain function of the spatial brightness B is integrated over the volume. In other words, it is a relationship between B and V, characterizing a given spatial brightness profile in FIDA. For example, the Gaussian profile yields the relationship $$\frac{dV}{dx} \propto \sqrt{x}, \quad (36)$$

where x=−ln B. The Gauss-Lorentzian profile yields the relationship $$\frac{dV}{dx} \propto e^{x/4}\sqrt{\sinh\frac{x}{2}}. \quad (37)$$

Both of the relationships are rather inflexible, i.e., they do not provide any spatial shape parameters to adjust the theoretically calculated distribution to fit the measured data.

When looking for sufficiently flexible models to fit experimental data, it might be useful to apply the following relationship:

$$\frac{dV}{dx} \propto x(1 + a_1 x + a_2 x^2). \quad (38)$$

There is a formal rather than a physical model behind Eq. (38). The fit quality obtainable with Eq. (38) is illustrated by the filled squares curve.

FIG. 2

Figure 2:
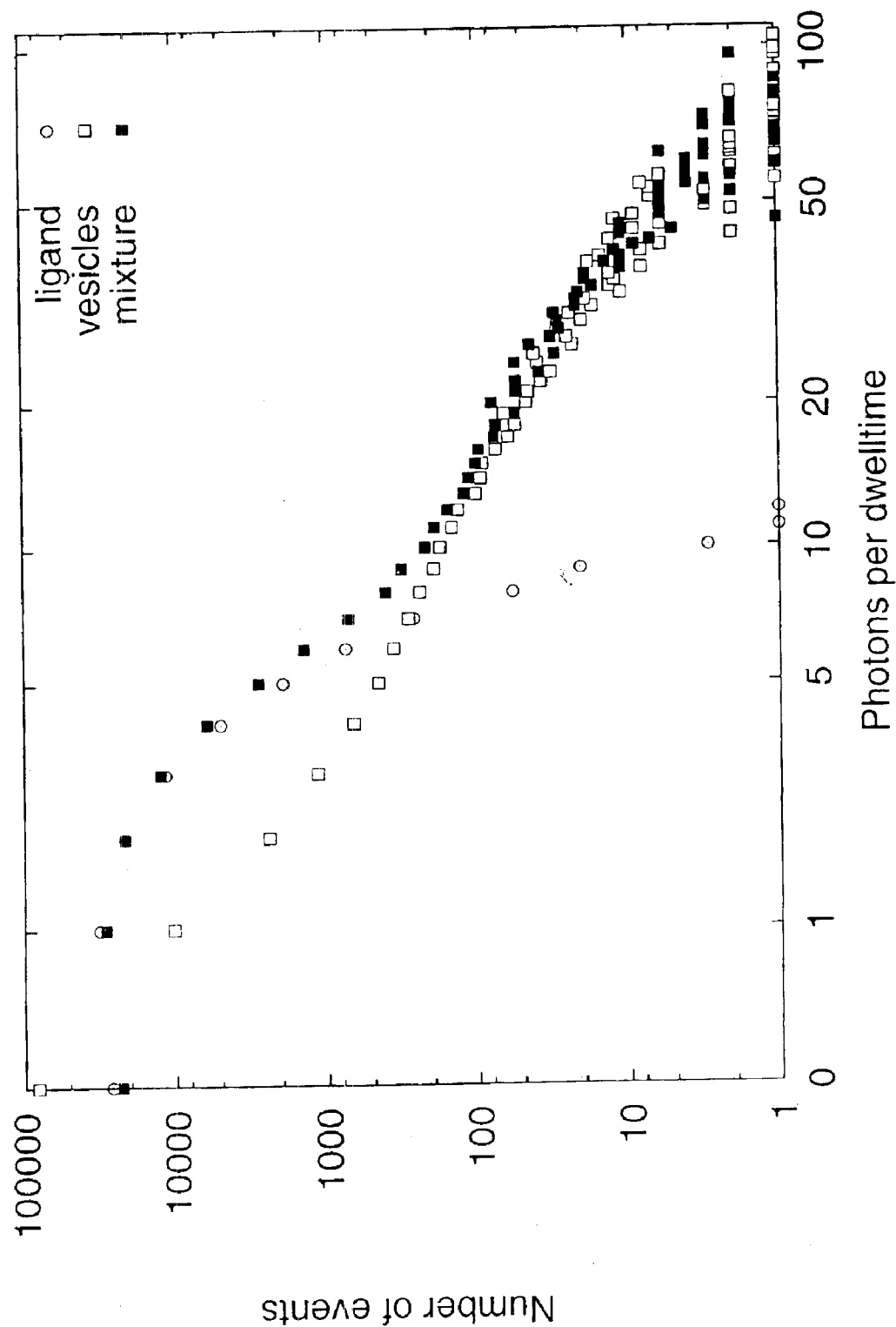
FIG. 2 shows simulated histograms of the number of counts for a case which models a binding reaction of a labeled ligand to vesicles.

Referring now to FIG. 2, simulated histograms of the number of counts are shown for a case which models a binding reaction of a labeled ligand to vesicles. Primary time intervals were 40 $\mu$s, values of the spatial parameters of Eq. (38) $a_1$=−0.4; $a_2$=0.08, background count rate b=1.0 kHz, data collection time 4 s. Curve "ligand" corresponds to a species of c=6.0; q=6.0 kHz/particle; $\sigma$q=0. Curve "vesicles" corresponds to a species of c=0.05; $\bar{q}$=300.0 kHz/particle; $\sigma$q=150.0. Curve "mixture" corresponds to their mixture. Concentrations and specific brightness values have been selected to model a characteristic situation in drug screening. Applying 1D-FIDA, fitting of curve (c) returns the values of the five parameters characterizing the given "sample" with statistical errors which are mostly between 3.5 and 6 percent, except the error of $\sigma$q of vesicles which is 13 percent. If, however, $\sigma$q of vesicles is fixed in fitting, all the statistical errors are below 4 percent.

For the fastest data simulation algorithm, one may calculate the expected distribution and generate a random Poisson number of events for each value of n independently. Generation of a random Poisson number is the following: For a given expected value of events E, a simulated number of events S is determined from a routinely generated number R between 0.0 and 1.0 through inequations $$\sum_{i=1}^{S-1} Poisson(i; E) < R \leq \sum_{i=1}^{S} Poisson(i; E).$$

As a cosmetic error, the total number of events $$\sum_n S(n)$$

may slightly deviate from the pre-given number M. A slower but a straightforward data simulation algorithm is the generation of a random configuration of particles in volume elements contributing to fluorescence, the calculation of the classical light intensity corresponding to the given configuration of particles, and the generation of a random Poisson number corresponding to this intensity, as a simulated number of photon counts. This procedure is repeated M times to obtain a simulated count number histogram.

FIGS. 3 to 8

FIGS. 3 to 8 illustrate theoretical errors of 1D-FIDA.

FIG. 3

Figure 3:
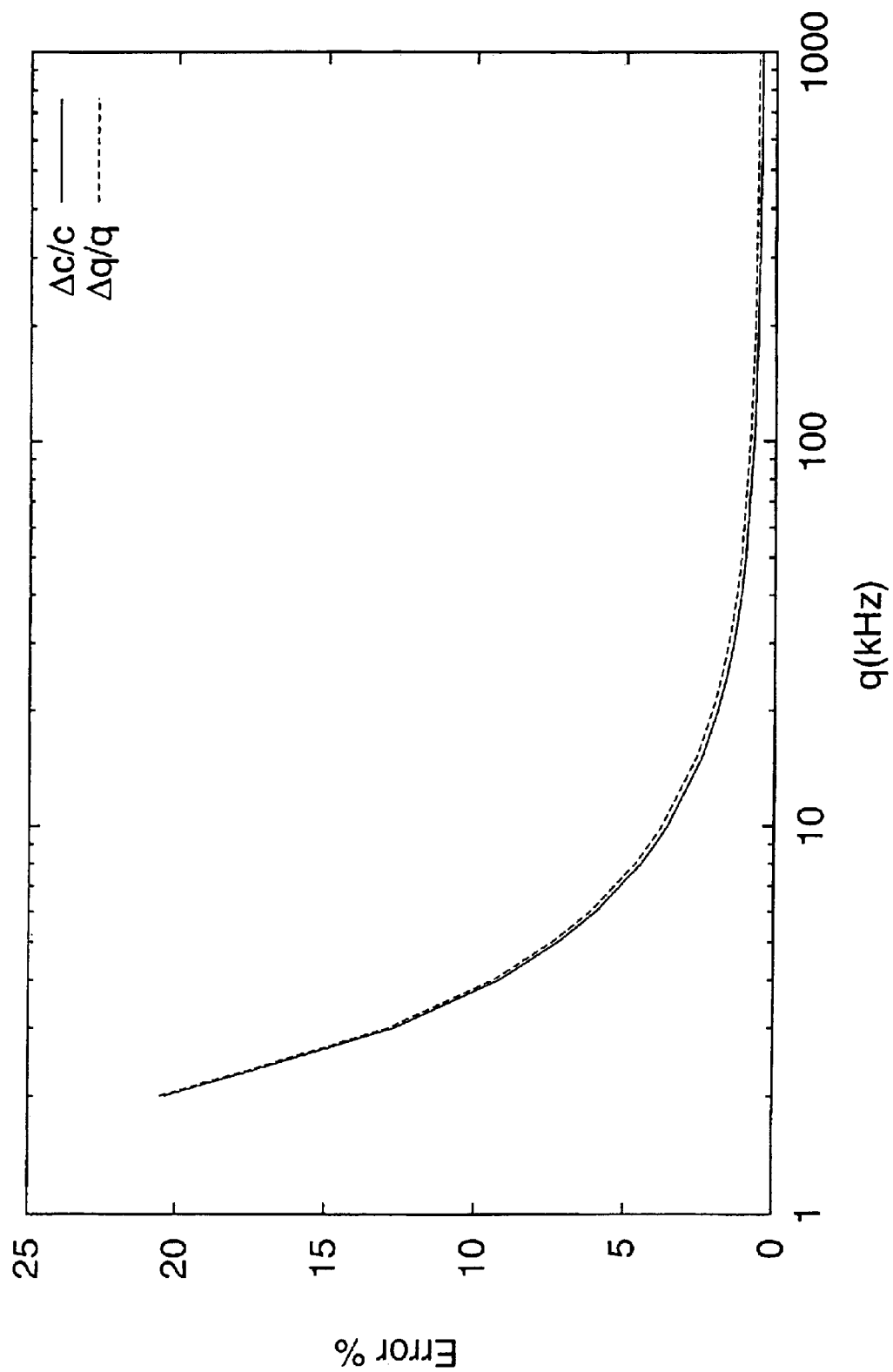
FIG. 3 illustrates theoretical errors of the estimated parameters c and q of a solution of single species, depending on the value of q.

Reference is now made to FIG. 3 which illustrates the theoretical errors of the estimated parameters c and q of a solution of single species, depending on the value of q. The following values of experimental parameters were selected: c=1.0; T=20 $\mu$s; $a_1$=−0.4; $a_2$=0.08; b=1.0 kHz; data collection time 2 s.

FIG. 4

Figure 4:
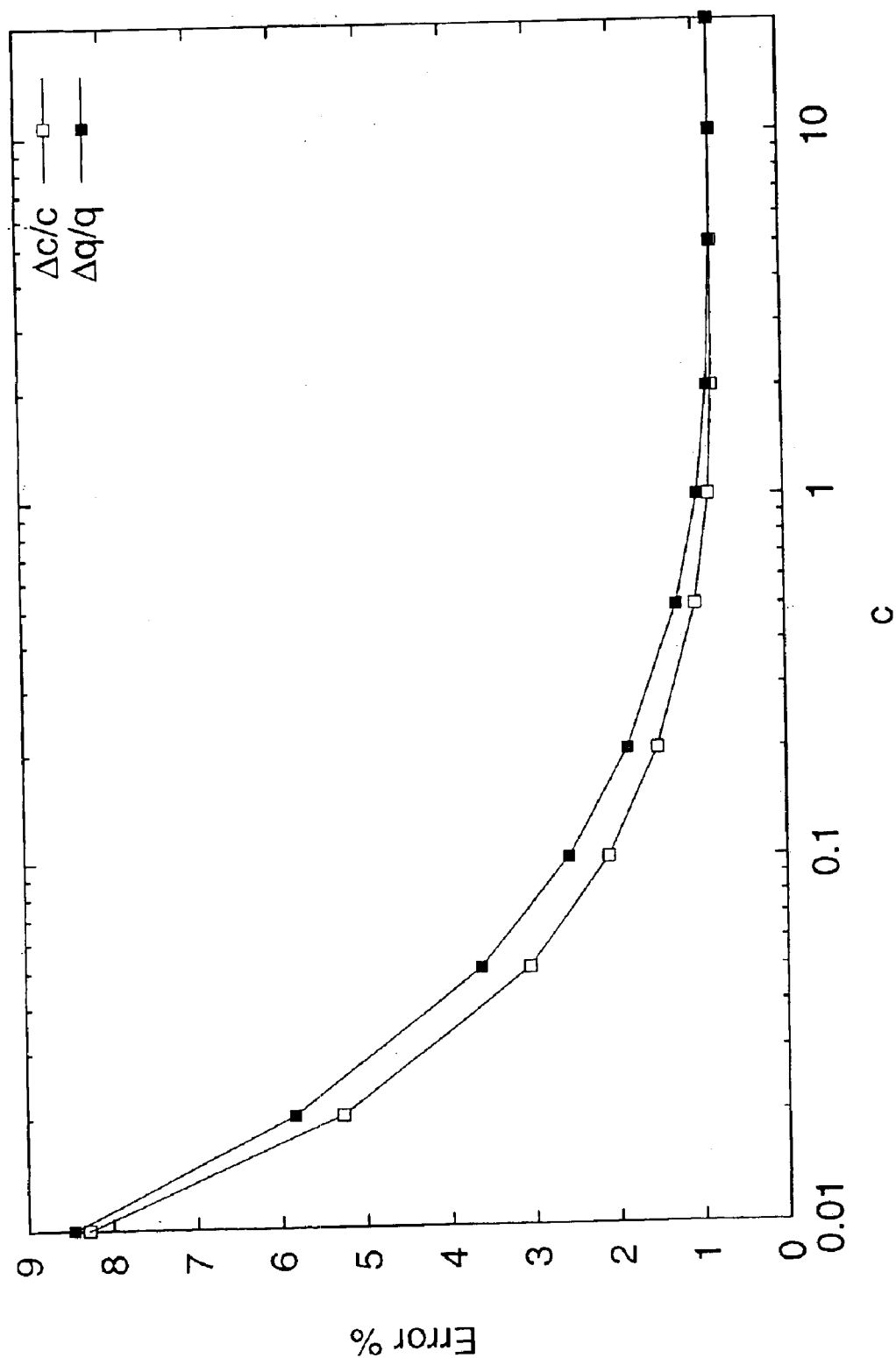
FIG. 4 illustrates theoretical errors of the estimated parameters c and q of a solution of single species, depending on the value of c.

FIG. 4 illustrates the theoretical errors of the estimated parameters c and q of a solution of single species, depending on the value of c. The following values of experimental parameters were selected: q=60 kHz/particle; T=20 $\mu$s; $a_1$=−0.4; $a_2$=0.08; b=1.0 kHz; data collection time 2 s.

FIG. 5

Figure 5:
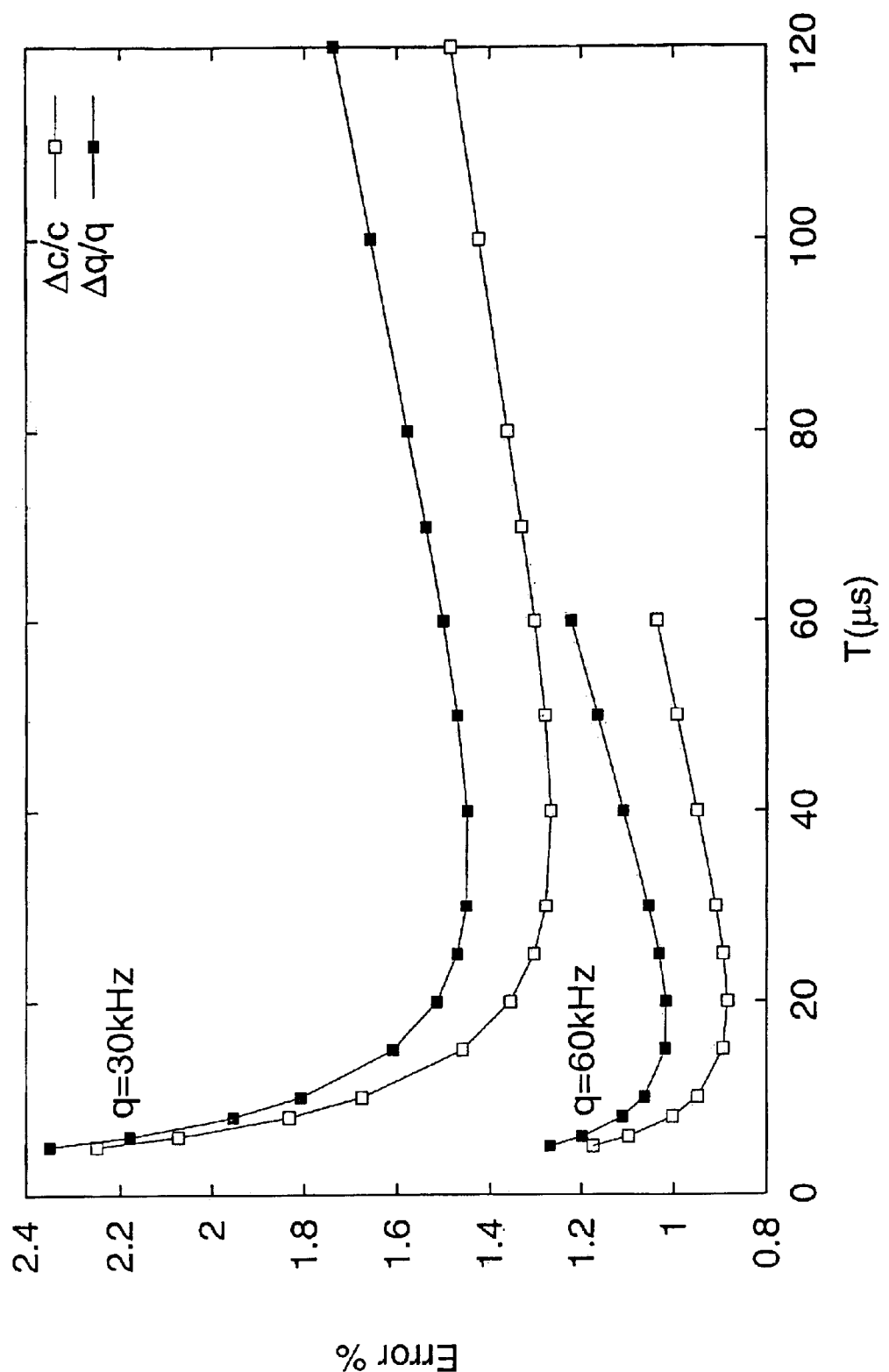
FIG. 5 illustrates theoretical errors of the estimated parameters of c and q of a solution of single species, depending on the value of T.

Referring now to FIG. 5, theoretical errors of the estimated parameters c and q of a solution of single species are shown, depending on the value of T. The following values of experimental parameters were selected: c=1.0; q=30.0 kHz/particle (upper graphs); q=60.0 kHz/particle (lower graphs); $a_1$=−0.4; $a_2$=0.08; b=1.0 kHz; data collection time 2 s.

FIG. 6

Figure 6:
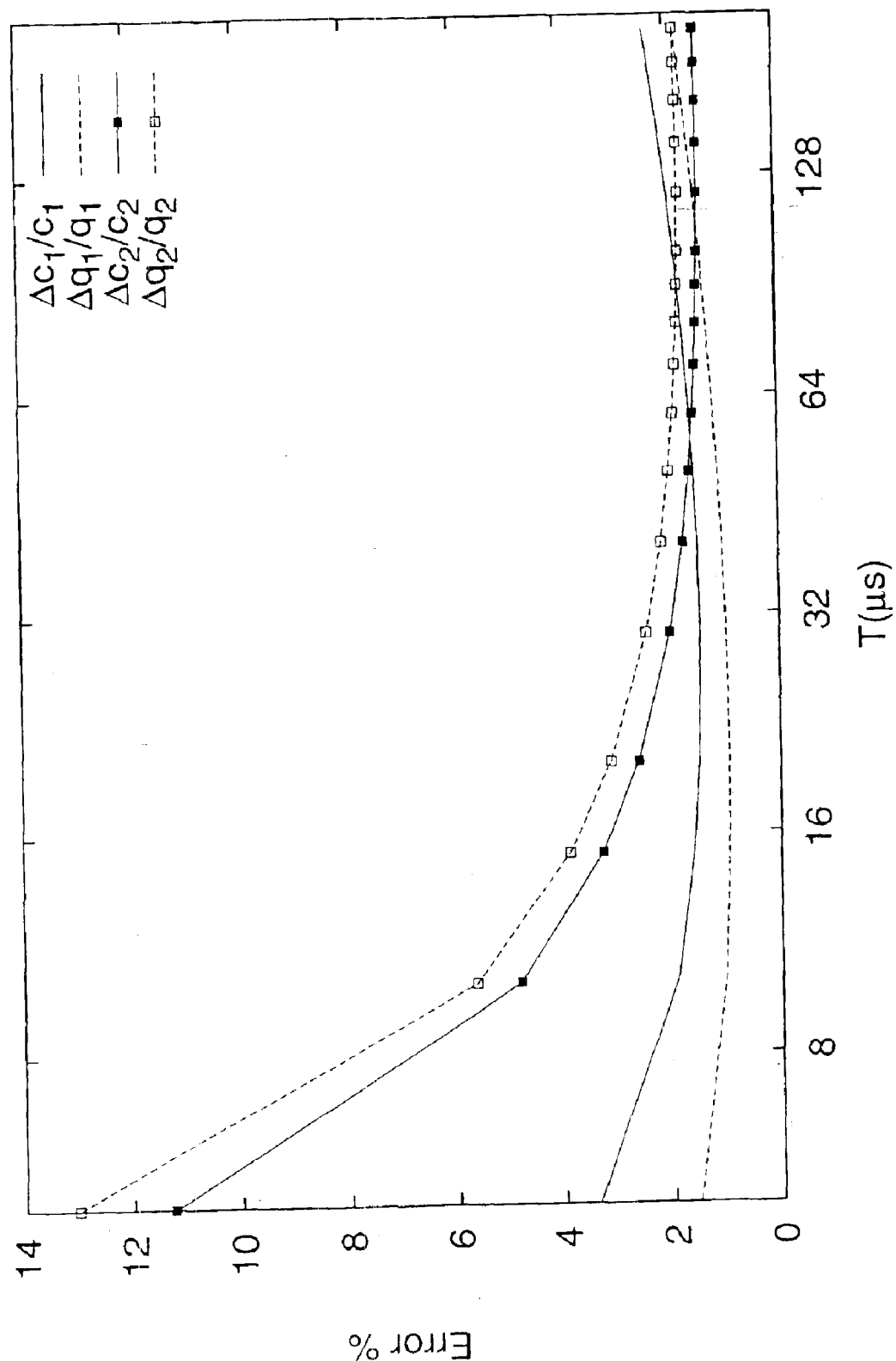
FIG. 6 illustrates theoretical errors of the estimated parameters c and q of a mixture of two species, depending on the value of T.

FIG. 6 illustrates the theoretical errors of the estimated parameters c and q of a mixture of two species, depending on the value of T. The following values of experimental parameters were selected: $c_1$=0.1; $c_2$=2.0; $q_1$=200.0 kHz/particle; $q_2$=10.0 kHz/particle; $a_1$=−0.4; $a_1$=0.08; b=1.0 kHz; data collection time 10 s. Note that the optimal value of T for the determination of the parameters of the brighter species is lower than that of the darker species.

FIG. 7

Figure 7:
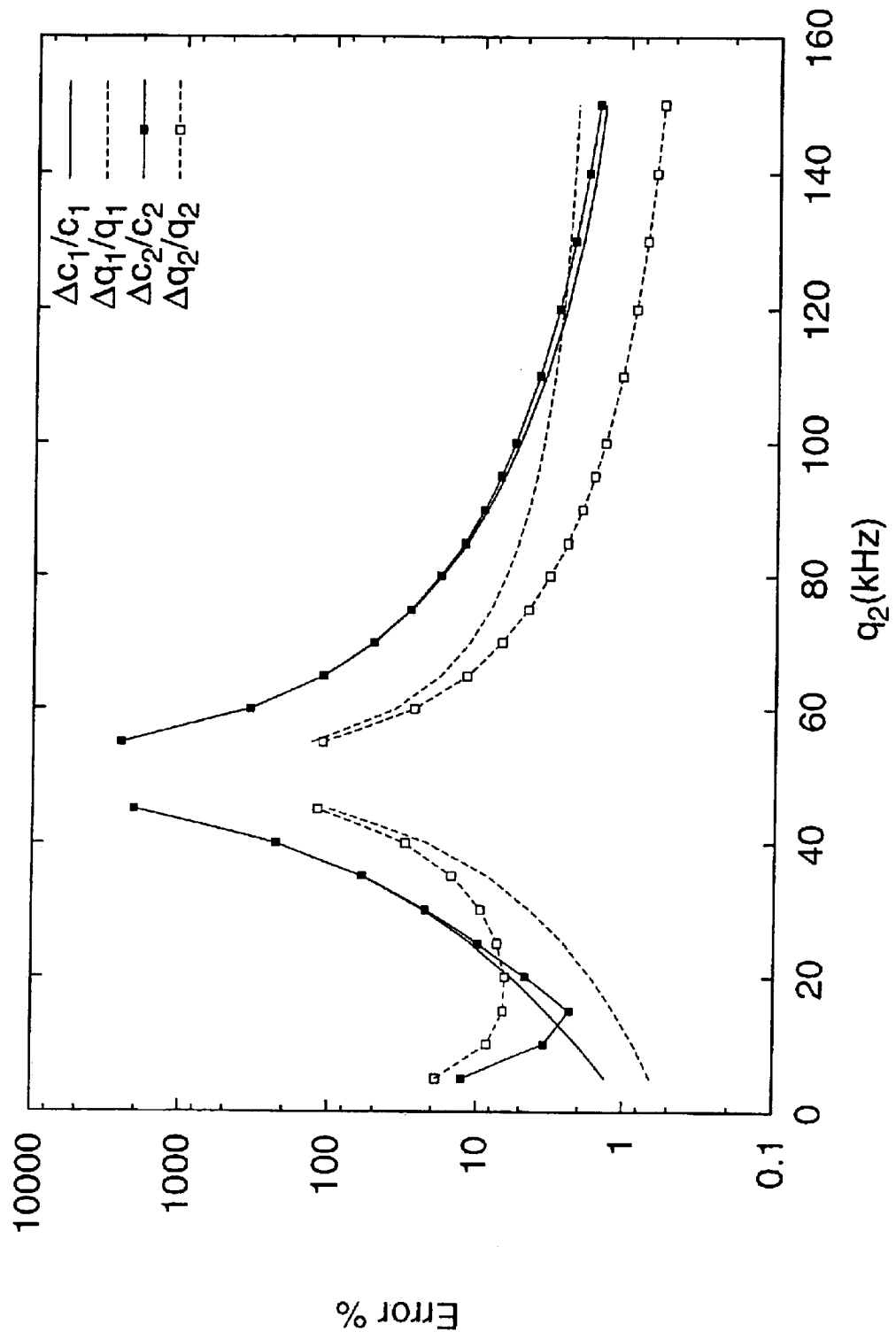
FIG. 7 illustrates theoretical errors of the estimated parameters c and q of a mixture of two species, depending on the ratio of $q_2$ to $q_1$.

Reference is now made to FIG. 7 which illustrates the theoretical errors of the estimated parameters c and q of a mixture of two species, depending on the ratio of $q_2$ to $q_1$. The following values of experimental parameters were selected: $q_1$=50.0 kHz/particle; $c_1$=$c_2$=0.5; $a_1$=−0.4; $a_2$=0.08; b=1.0 kHz; data collection time 40 s.

FIG. 8

Figure 8:
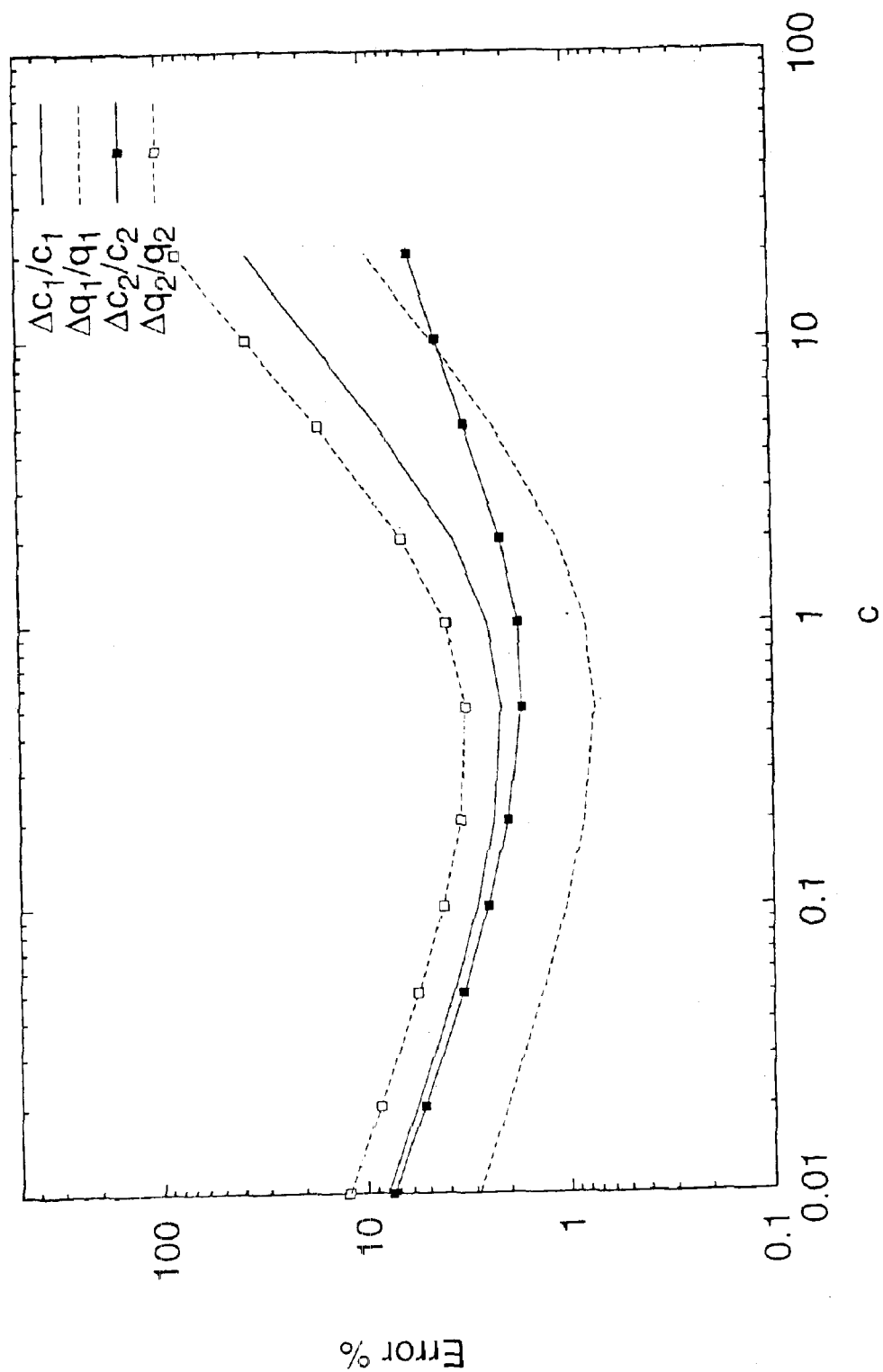
FIG. 8 illustrates theoretical errors of the estimated parameters c and q of a mixture of two species, depending on concentrations.

FIG. 8 illustrates the theoretical errors of the estimated parameters c and q of a mixture of two species, depending on concentrations. The concentrations were changed synchronously, $c_1$=$c_2$. The following values of experimental parameters were selected: $q_1$=75.0 kHz/particle; $q_2$=25.0 kHz/particle; $a_{1=-0.4}$; $a_2$=0.08; b=1.0 kHz; data collection time 60 s. Note that an optimal concentration exists at about one particle per sample volume. This is generally true, except if less than three parameters are to be determined.

FIG. 9

Figure 9:
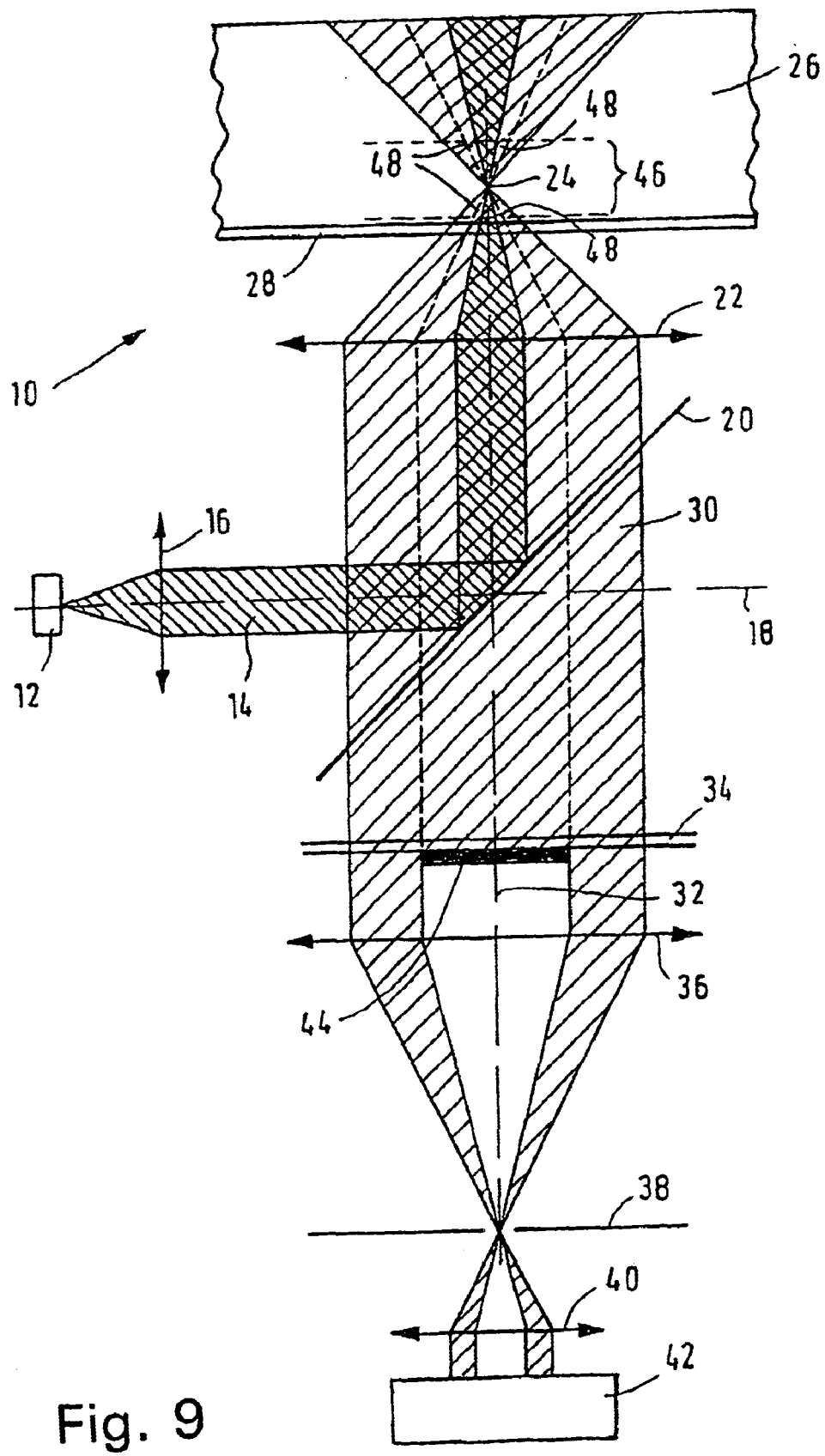
FIG. 9 illustrates an apparatus adapted for use in performing the method according to the present invention.

Reference is now made to FIG. 9 which shows one embodiment of an apparatus adapted for use in performing the method according to the present invention. Apparatus 10 comprises a laser 12 which serves as a light source for illuminating the sample by a bundle of coherent, monochromatic excitation radiation 14. Excitation radiation 14 is paralleled by a lens 16 and reaches a dichroic mirror 20. Preferably, the angle between the optical axes 18 and the dichroic mirror 20 is 45°. The dichroic mirror 20 reflects the excitation radiation 14 in direction of an objective lens 22 having its focus 24 within a sample volume 26. Sample volume 26 and objective lens 22 are preferably separated from each other by a transparent cover glass 28, e. g. by the bottom of a commercially available micro-titer plate which houses the sample. The sample preferably includes fluorescently labelled molecules or other particles. Due to excitation by an appropriate excitation radiation 14, the molecules or other particles present in the sample emit radiation 30. Emission radiation 30 passes the objective lens 22 and reaches the dichroic mirror 20 which is transparent for emission radiation 30. Thereafter, emission radiation passes a filter 34 and a collimator lens 36 on the optical axes 32. A pinhole 38 is situated in the focus of collimator lens 36. Emission radiation 30 passing the pinhole 38 reaches a further lens 40 and, thereafter, is detected by the photodetector 42. Within the pathway of emission radiation 30, in particular between dichroic mirror 20 and photo-detector 42, an opaque means 44 is provided through which a central part of the emission radiation 30 cannot pass. This central part of the emission radiation 30 stems from areas on the optical axes 32 in front of or behind the focus 24 of the excitation radiation 14. Only emission radiation 30 that stems from the focus 24 or its direct neighbourhood passes the pinhole 38 and reaches photo-detector 42. Instead of placing an opaque means 44 within the pathway of emission radiation 30, the pathway of excitation radiation 14 is also suitable for positioning an opaque means 44. In particular, an opaque means 44 can be positioned between laser 12 and dichroic mirror 20. Use of an opaque means 44 as described in detail herein improves the signal-to-noise ratio.

FIG. 10

In FIG. 10A, the calculated photon count number distributions, P(n), for five cases of equal mean count rate, $\bar{n}$=1.0 are shown. The open symbols correspond to solutions of single species, but with different values of the mean count number per particle qT. The solid line is calculated for a mixture of two species, one with qT=0.5 and the other with qT=8.0. Obviously, the curves differ from each other considerably. The important point is that 1D-FIDA according to the present invention can unambiguously separate the contributions of the individual species.

Reference is now made to FIG. 10B which illustrates the distributions of the number of photon counts of pure solutions of two different dyes, 0.5 nM rhodamine 6G (Rh6G) and 1.5 nM tetramethylrhodamine (TMR), as well as a mixture of the two (0.8 nM TMR, 0.1 nM Rh6G). The main equipment is a confocal microscope.(ConfoCor®; EVOTEC BioSystems and Carl Zeiss, Germany) routinely used for fluorescence correlation studies. An attenuated (to about 800 $\mu$W) beam from an argon ion laser, wavelength 514.5 Mn, is focussed to a spot of approximately 0.5 $\mu$m radius, which is twice the size of a spot in usual FCS experiments, and results in a diffusion time of approximately 200 $\mu$s for rhodamine 6G. The excitation intensity has generally been kept lower than or equal to a level characterized by about 15 percent amplitude of the triplet term of the auto-correlation function. Fluorescence emission is detected through a pinhole on the focal plane of the microscope using an avalanche photodiode detector SPCM-AQ 131 (EG&G). The histograms of the number of photon counts were measured at T=40 $\mu$s dwell time. Data collection time was 50 s. These histograms serve. as input data for 1D-FIDA. The results of a multi-component fit analysis are given in Table 5 below with $\chi^2$ values calculated according:

$$\chi^2 = \frac{\sum W_n [\hat{P}(n) - P(n)]^2}{n_P - n_{fit}}, \tag{39}$$

where $n_p$ is the length of the measured histogram $\hat{P}(n)$, and $n_{fit}$ is the number of fit parameters. In said multi-component analysis one fits the measured histogram of the number of photon counts, assuming a certain number of fluorescent species, and estimates unknown concentration and specific brightness values.

TABLE 5

| Sample  | $a_2$              | $a_3$             | c                                      | q (kHz)                          | $\chi^2$ |
|---------|--------------------|-------------------|----------------------------------------|----------------------------------|----------|
| Rh6G    | −0.380 ± 0.009     | 0.077 ± 0.003     | −0.461 ± 0.003                         | 107.2 ± 0.8                      | 0.97     |
| TMR     | −0.427 ± 0.032     | 0.084 ± 0.014     | 1.517 ± 0.012                          | 36.56 ± 0.29                     | 0.81     |
| Mixture | −0.380 (fixed)     | 0.077 (fixed)     | 0.103 ± 0.012<br>0.738 ± 0.011         | 109.1 ± 4.0<br>37.4 ± 1.0        | 0.77     |

In all cases, the background count rate was fixed to the value of 1.05 kHz, as measured with de-ionized water. $a_2$ and $a_3$ are pre-normalization values when $a_1$ is fixed to 1.0. The theoretical statistical errors in Table 5 correspond to theoretical weights:

$$W_n = \frac{N}{P(n) + \frac{1}{N}}. \tag{40}$$

This formula is derived under a simple assumption of N independent measurements of the number of photon counts. In reality, consecutive measurements are correlated, therefore the errors of estimated parameters returned by the fitting algorithm underestimate real statistical errors. We have empirically determined from a separate series of 30 to 200 measurements that these statistical errors are greater than theoretical ones by a factor of about three.

The exemplary residuals for Rh6G are shown in FIG. 10C.

Most often, 1D-FIDA is used assuming a given number of fluorescent species and finding the best fit between the measured and theoretical distributions under this assumption. However, 1D-FIDA can also be applied assuming a continuous distribution of specific brightness of the fluorescent particles. This method is known in general as inverse transform with regularizations (ITR). The results of ITR analysis in 1D-FIDA are shown in FIG. 10D expressing the distribution of the number of particles as a function of their specific brightness. Such ITR analysis realized with the help of linear regularization and constraining concentrations to non-negative values. ITR is a valuable tool especially for samples from which either no a priori information about the sample composition is given or where the sample composition is heterogeneous. The dashed lines correspond to the solutions of the single dyes (Rh6G and TMR) and the solid line to their mixture. The ordinates give the mean number of particles within the confocal volume element (left: single dyes; right: mixture). For equipment details see description of FIG. 10B. The ideal outcome would be single δ-peaks for the solutions of single species and two δ-peaks for the mixture. In reality, the width of the ITR output spectral peaks is determined not only by the true width of the distribution of specific brightness values but also by the accuracy of input data and the particular realization of the linear regularization: simply, if a broad spectrum fits experimental data as well as a narrow one then ITR prefers the broad one.

FIG. 11

As a further example, 1D-FIDA according to the present invention has been applied to study the hybridization of 5'-(6-carboxytetramethylrhodamine (TAMRA))-labeled 40 mers with either labeled or non-labeled complementary oligonucleotides and the subsequent symmetrical cleavage of the DNA hybrid by the restriction endonucleases Hind III and Kpn I. The specific oligonucleotides used in this study were TAMRA-AAGAAGGGGTACCTTTGGATAAAA-
    GAGAAGCTTTTCCCGT(5'-TAMRA-Oligo A)

and

TAMRA-ACGGGAAAAGCTTCTCTTTTATCCAAAG-
    GTACCCCTTCTT(5'-TAMRA-Oligo B).

They were purchased in HPLC pure quality from Applied Biosystems (Weiterstadt, Germany). All measurements were carried out on the above described FCS reader at excitation/emission wavelengths of 543/580 nm using a 4 mW helium/neon laser (Uniphase) attenuated to approximately 300 μW. The water background was found to be below 800 Hz. For the measurements, sample aliquots were diluted to 1 nM and 20 μl were assayed in a 8-well chambered coverglass (Nalge Nunc) at room temperature. The hybridization reaction was performed in 70% formamide containing 10mM Tris/HCl buffer (pH 8.0), 1 mM EDTA, 0.2 mM NaCl and an oligonucleotide concentration of 0.5 μM. Denaturation was at 95° C. for 2 min and subsequent hybridization was at 55–60° C. for 40 min in accordance with the optimized temperature Tx which is 10–15 degrees below the melting point Tm (Heating block, Techne). Tm was calculated as follows: Tm=81.5+16.6 (log10[Na+])+0.41 (%G+C)−600/N (N=40; %G+C=42.5). Restriction digest analyses of the hybrid DNA were performed by the restriction enzymes Hind II and Kpn I. The restriction site was chosen in order to obtain fragments of different size. The cleavage reactions were performed in 3.3 mM tris/acetate (pH 7.9), 1 mM magnesium acetate, 6.6. mM potassium acetate and 0.1 mg/ml bovine serum albumin at 37° C. for 1 h. The reaction course is characterized by significant shifts of the fluorescence intensity per molecule within a range of one order of magnitude (FIGS. 11A–E). It is important to note that the resulting double product peak corresponds to one single hybridization species in which no none-hybridized species are detectable. This could be easily demonstrated in hybridization/cleavage experiments using labeled/nonlabeled oligonucleotide combinations where signals with different brightness compared with the double labeled hybrid have been obtained (FIG. 12A,B). One explanation for such a double-peak structure could be conformational fluctuations resulting from transitions between two conformational states. This behavior is described using a three-state model of the conformational dynamics with a polar, a nonpolar, and a quenching environment of the label (Eggeling et al., Proc. Natl. Acad. Sci. USA 95: 1556–1561). From the present data it can be concluded that the conformational fluctuations are significantly dependent on the DNA length and the number of labels. The small digested DNA fragments exhibit a single brightness and the concentration ratio of the educt double peaks shifts toward one component when one-label hybrids are studied. As a further result, small fragments show low molecular brightness and large fragments correspond to high brightness values ($Q_2 \approx Q_3$, $Q_1 \approx Q_4$).

FIG. 12

Based on symmetrical cleavage sites for both enzymes DNA fragments of equal size and subsequently very similar molecular brightness are to be expected. FIGS. 12A and B clearly illustrate that such a result has been observed and the theoretical relationship $Q_1+Q_2=Q_3+Q_4$ is experimentally confirmed. Restriction digest analyses of the hybrid DNA were performed with the restriction enzymes Hind III and Kpn I either alone or in combination. The restriction sites lead to symmetrically cleaved fragments (2×12 mers, 1×16 mer for double digest). [•] corresponds to labeled DNA. $Q_{01-03}$: intensities of DNA hybrids, $Q_1$: intensities of cleavage products. The bulk of all the measurements of cleavage products using single and doubly labeled DNA structures makes it possible to classify all observed intensities with individual structures in a single measurement—a property of the method of the present invention which is not possible using any other known analytical method.

FIGS. 13 and 14

Reference is now made to FIGS. 13 and 14. As the central optical part of the equipment for 2D-FIDA, a confocal microscope is used, like in FCS spectrometers (Koppel et al., Biophys. J. 16: 1315–1329, 1976): For excitaton of fluorescence, a beam from an Ar or green He—Ne laser is attenuated by neutral filters, passes a beam expander and is directed to the microscope objective by a dichroic mirror. In a number of experiments with slowly diffusing particles, beam scanning in combination with sample scanning is used, as a tool known from laser scanning microscopy. Fluorescence is collected by the same objective through the dichroic mirror, and is focussed to a confocal pinhole which serves to reject the out-of-focus light. Resolution in the longitudinal direction is additionally improved by using a concentrical opaque spot closing about a quarter of the aperture in the fluorescence collection path of the microscope (see description of FIG. 9). The light which passes the pinhole is divided by a beamsplitter for detection by two detectors. Depending on the general type of a 2D-FIDA experiment, the beamsplitter is either a polarization cube, or a dichroic mirror. In the first case, a common spectral band-pass filter is used, while in the case of two-colour FIDA, each detector has a different band-pass filter in front of it. The photon counting detectors are silicon avalanche photodiode modules SPCM-AQ-131, EG&G Optoelectronics, Canada. The TTL pulses from the detectors are counted by a two-channel counter, constructed by EVO-TEC BioSystems AG (Hamburg, Germany) as a plug-in card of a computer. The count number distributions are calculated during reading data from the 32 MB onboard buffer, which itself is an online process. By feeding the detector outputs to a correlator, FCS measurements can be performed in parallel with FIDA experiments.

The levels of background count rate for both detectors are determined by a separate experiment on bi-distilled water. The main contributor to the non-fluctuating background light intensity is Raman scattering from water.

The radius of the monitored sample volume can be adjusted by selecting an appropriate expansion factor of the original laser beam. The focal beam radius of about 0.6 $\mu$m is used yielding diffusion times for simple organic dye molecules (e.g., TAMRA) of about 260 $\mu$s, which is considered long compared to the 40 $\mu$s dwell time of counters, so that the approximation of constant molecular brightness during the counting interval is valid. The excitation intensity is adjusted as a compromise between a high count rate per molecule and low population of the triplet state. The triplet state population was kept at about 15 percent level. Higher triplet population values might significantly distort the apparent spatial brightness profile. The population of the triplet state was measured with the correlator (ALV-5000, ALV, Langer, Germany) during the set-up of a series of experiments.

For methodological test experiments, two different dyes were selected, carboxytetramethylrhodamine (TAMRA) and rhodamine red X (RRX). These dyes have different emission spectra, as well as different extinction coefficients at the laser wavelength of 543.5 nm. In these experiments, a wideband 40/60 beamsplitter was used in front of the detectors. The spectral filter of the "red" channel has the center wavelength of 605 nm and FWHM of 50 nm while the corresponding figures for the "yellow-green" channel are 575 nm and 30 nm. The dyes were diluted in distilled water so that the average number of molecules in the observation volume was in the range of 0.5 to 2.0, corresponding to concentrations between 0.23 and 0.92 nM.

For each experiment, about 20 $\mu$l of the sample solution was placed on a coverslip separating the sample from the water immersion objective (Zeiss C-Apochromat 40×1.2 W Korr). Each histogram was collected for 60 seconds. Each of the dyes was measured separately, but also mixtures of the dyes with different concentration ratios were measured. The parameters describing the spatial brightness profile were determined from an experiment on TAMRA and were fixed in sequent analysis of other samples at values $a_1=-0.405$ and $a_2=0.0772$. Mixtures were measured and analyzed in order to see how well the method returns values of specific parameters of the two species.

As an example, FIG. 13 visualizes a count number histogram measured for a pure TAMRA solution. Values corresponding to the z-axis are the numbers of events for a given pair of count numbers $n_1$ and $n_2$. Fitting of the distribution returns mean number of particles, cV=1.139±0.005, specific brightness for the "red" channel $q_1$=79.4±0.5 kHz, and for the "yellow-green" channel $q_2$=50.9±0.3 kHz. In Table 6, results of analysis of test experiments are presented. Samples have not been specified by concentration values calculated from dilution factors of the preparation because adsorption of dye molecules to glass surfaces influences real concentrations significantly. Because of the same reason, concentration values are not well reproduced from sample to sample; a shift of concentration values from realization to realization is also sometimes observable. Specific brightness values are well reproduced, however. Values of statistical errors presented are theoretical values corresponding to the assumption of uncorrelated measurements, multiplied by three, which is an empirical factor. In addition to statistical errors, deviations from sample to sample of a modest size are also noticeable.

TABLE 6

| Sample | Realization number | Mean number of molecules per sample volume, cV | Specific brightness in "red", $q_1$, kHz | Specific brightness in "yellow-green", $q_2$, kHz |
|---|---|---|---|---|
| TAMRA | 1 | 1.128 ± 0.005 | 79.6 ± 0.4 | 51.3 ± 0.3 |
|  | 2 | 1.139 | 79.4 | 50.9 |
|  | 3 | 1.160 | 79.4 | 50.8 |
|  | 4 | 1.171 | 79.0 | 50.6 |
| RRX | 1 | 1.892 ± 0.009 | 48.0 ± 0.3 | 15.63 ± 0.09 |
|  | 2 | 1.859 | 48.0 | 15.63 |
|  | 3 | 1.850 | 47.3 | 15.44 |
|  | 4 | 1.811 | 47.9 | 15.58 |
| TAMRA and RRX | 1 | 0.99 ± 0.05 | 78.0 ± 1.0 | 51.8 ± 1.1 |
|  |  | 1.14 ± 0.05 | 49.1 ± 1.1 | 15.0 ± 0.9 |
|  | 2 | 1.01 | 76.8 | 51.1 |
|  |  | 1.08 | 49.5 | 15.1 |
|  | 3 | 0.99 | 77.9 | 51.8 |
|  |  | 1.03 | 49.3 | 15.1 |
|  | 4 | 0.97 | 76.9 | 51.7 |
|  |  | 1.03 | 50.0 | 15.5 |

TABLE 6-continued

| Sample | Realization number | Mean number of molecules per sample volume, cV | Specific brightness in red-red", $q_1$, kHz | Specific brightness in "yellow-green", $q_2$, kHz |
|---|---|---|---|---|
| TAMRA and RRX, new sample | 1 | 0.93 ± 0.07 | 74.6 ± 1.3 | 49.6 ± 1.5 |
| | | 2.51 ± 0.07 | 47.6 ± 0.8 | 14.7 ± 0.5 |
| | 2 | 0.98 | 75.2 | 49.2 |
| | | 2.38 | 46.8 | 14.2 |
| | 3 | 0.96 | 75.0 | 49.4 |
| | | 2.25 | 48.0 | 14.7 |
| | 4 | 0.94 | 76.1 | 49.9 |
| | | 2.16 | 47.6 | 14.8 |

It is worth noting that histograms measured with mixtures are qualitatively different from those measured for pure dyes. FIG. 14 visualizes weighted residuals of fitting a distribution measured with a mixture of TAMRA and RRX. The upper graph corresponds to the adequate analysis when two species were assumed to the present; residuals are scattered quite randomly and uniformly. The lower graph corresponds to the assumption that only a single species is present; there is a significant difference between the measured and the calculated distribution in this case. $n_1$ is the count number obtained by the "red" detector, and $n_2$ is the count number obtained by the "yellow-green" detector.

FIGS. 15 and 16

In traditional fluorescence polarization studies, average intensities of two polarization components of fluorescence are directly measured. Fluctuations of the intensities are not of direct interest there but are considered rather as a source of statistical errors. Changes in the fluorescence polarization values of a sample containing a fluorescently labeled binding partner reflect changes in molecular volume and, hence, provide direct information on equilibrium binding. Fluorescence polarization measurements can also be performed in real-time, allowing the kinetic analysis of association and dissociation reactions. One of the most widely-used fluorescence polarization applications is the competitive immunoassay used for the detection of therapeutic and illicit drugs. The method of fluorescence polarization has been used for clinical immunoassays for more than a decade. The homogeneous FPIA (fluorescence polarization in immunoassays) has well-accepted advantages over conventional heterogeneous immunoassays like RIA or ELISA. However, it fails if multi-binding step reactions are to be investigated because the separation of individually polarized species is impossible. Therefore, ligand binding curves only demonstrate the overall decrease of polarization, meaning the mechanistic binding constants cannot be determined. Further limitations are seen in sample volume as well as in mass restrictions.

With a two-dimensional fluorescence intensity distribution analysis according to the present invention, the full content of information usually buried in fluorescence anisotropy can be utilized, thereby overcoming the limitations mentioned above. 2D-FIDA directly determines two specific quantities per each fluorescence species in one measurement: the fluorescence intensity per molecule and the anisotropy of a given model. Based on this supplementary information, the delineation of all participating species and even the quantification of the binding behavior is possible. 2D-FIDA anisotropy is an ideal tool for the quantitative description of systems exhibiting multiple binding steps, aggregation and multimerization phenomena.

In the following, an application of 2D-FIDA in its polarization mode is described, where an interaction between theophylline antigen and anti-theophylline antibody was studied.

Theophylline therapy has been a cornerstone of asthma therapy for several years and, therefore, there is a strong demand for assaying and fine-tuning the theophylline level in serum. To demonstrate the capabilities of the present invention, the binding of theophylline antigens to anti-theophylline antibodies from a polyclonal anti-theophylline serum has been investigated. The antigens were labeled with 5'-carboxytetramethylrhodamine (TAMRA) with and without an incorporated spacer. In classical FP analysis these conjugates exhibited low anisotropy values (0.037 and 0.055 respectively) upon interacting with the antibody. Therefore they form a critical basis for illustrating the sensitivity of the present invention.

For the binding experiments the stock solutions of antibody and antigens were diluted in a PBS buffer with 0.05% Tween 20. After mixing the compounds, the mixture was incubated for 30 minutes at room temperature. Matching the spectral properties of the conjugates the system was excited at the; 543 nm line of a He/Ne laser (Uniphase). As two examples, measured joint histograms of photon count numbers and results of 2D-FIDA applied to samples at different antibody dilution values but a constant ligand concentration of [L]=2 nM are illustrated by FIGS. 15 and 16. Antibody concentrations are in arbitrary units referring to effective dilutions. Water background was below 1 kHz in each detection channel.

FIGS. 17–19

In the two-color fluorescence intensity distribution analysis according to the present invention, two detectors are spectrally tuned to monitor fluorescence from two labels of different color. In the assay type described below, ligand molecules are labeled in "green". Since each vesicle carries a high number of receptors, vesicles in samples with a low binding degree can be distinguished from vesicles in samples with high binding degree by a significantly higher specific brightness in "green". Vesicles are additionally stained in "red". Specific brightness of vesicles in "red" is not altered by binding of ligand molecules, but staining in "red" is a means to increase contrast between free ligand molecules (which are nearly invisible in "red") and vesicles (which in the case of extremely low binding may be of nearly the same brightness in "green" as free ligand molecules). Contributions from the two fluorescent species of a single sample to the measured 2-dimensional distribution of the numbers of photon counts are very different in this assay type indeed, and therefore the analysis is highly reliable.

To demonstrate the advantages of a two-dimensional fluorescence intensity distribution analysis according to the present invention, the binding of TAMRA-labeled somatostatin-14 (SMS14-5TAMRA) to the human type-2 high affinity somatostatin receptor SSTR-2 (P. Schoeffter et al., Eur. J. Pharm., 289, 163–173, 1995) has been chosen as biological system. The receptor was expressed by CCL39hsst2 cells. Vesicles were prepared from this cell line and stained by the lipophilic tracer $DiC_{18}(5)$. The binding reaction was carried out in 10 mM HEPES (pH 7.6), 5 mM $MgCl_2$, 0.01% (w/v) fluorosurfactant FC-135, 1.33% DMSO in the presence of protease inhibitors. A schematical drawing of the principle of the assay is shown in FIG. 17.

For excitation of fluorescence of the two spectrally distinct labels, the 532 nm line of a Neodym:Yag laser attenuated to 250 μW and the 632 nm line of a He—Ne laser attenuated to 25 μW were simultaneously used. In order to minimize misalignment of the two laser beams, they both passed through a single optical fiber before being focussed by the microscope. Also, the collected fluorescence beam passed a single pinhole before being splitted for the two detectors. An optical band-pass filter with the center wavelength 590 nm, FWHM 60 nm, and another one with the center wavelength 690 nm, FWHM 40 nm were used in front of the two detectors, monitoring fluorescence from the two labels separately. Because vesicles are slowly diffusing particles, in this experiment an area of 0.05 mm² of each sample was scanned, using sinusoidal beam scanning of 25 Hz frequency, 100 μm amplitude in one direction, and sample scanning of 500 μm per 8 s data collection time in the other direction.

Figure 18A:
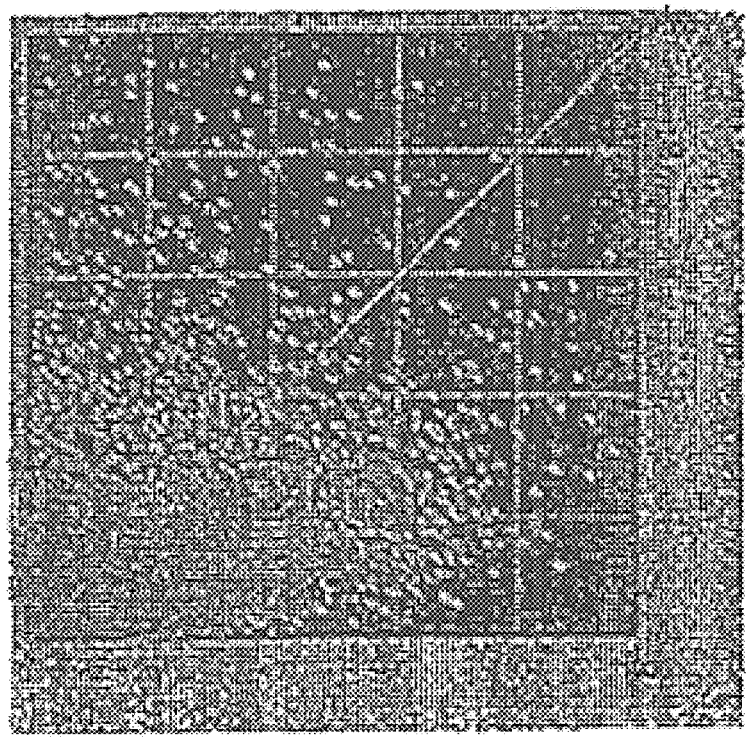
Figure 18B:
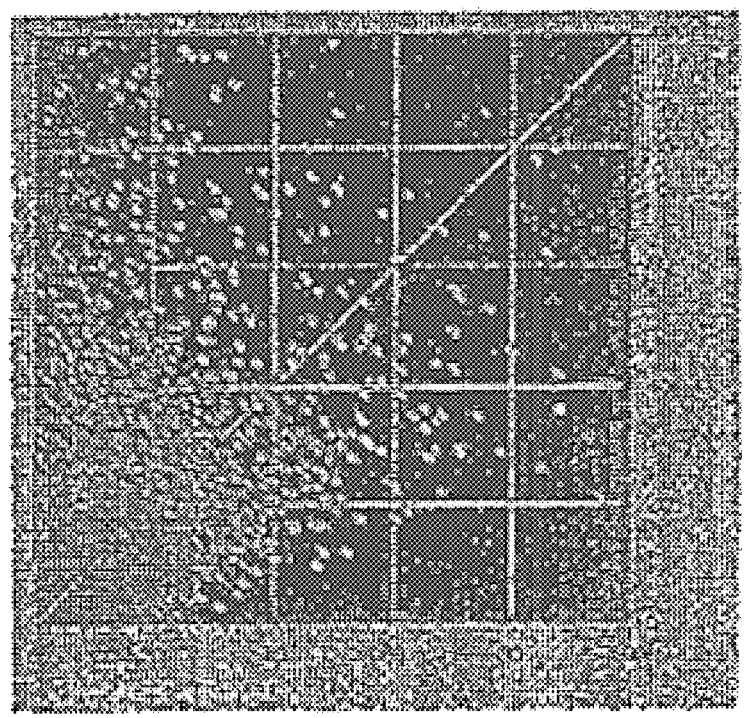

In FIG. 18 two typical examples of count number histograms corresponding to a high and a low degree of binding are compared. In FIG. 18A, the vesicle bound ligand (SMS14-5TAMRA) was competed off by the addition of a large excess of non fluorescent competitor (SRIF-14, SIGMA; 1 μm competitor, 3 nM total ligand). It is clearly visible that the histogram obtained in the absence of competitor (FIG. 18B) is more expanded in the $n_2$ direction than in the presence of competitor. The $n_2$ direction represents the green fluorescence of the labeled ligand and, hence, is a measure for the ligand binding.

2D-FIDA according to the present invention was applied to each of the measured histograms. Using a two-component fit algorithm, both the concentration (particle number in the confocal volume) and the fluorescence brightness values for the free ligand and the ligand bound to vesicles were obtained. The vesicles are well separated from the free ligand even in the presence of competitor (low binding). Addition of competitor leads to a decrease in the green fluorescence of the vesicles and an increase in the concentration of free ligand. The fact that the ligand does not completely dissociate from the vesicles is due to unspecific binding which is dependent on the amount of vesicles used in the assay.

Next, the competitor has been titrated from 1 μM down to 10 pM (10 measurements each) in order to record a dose-response curve and to determine the $EC_{50}$ value. As shown in FIG. 19, 2D-FIDA analysis leads to a typical sigmoidal competition curve with very low standard deviations. The calculated $EC_{50}$ value is 0.87 nM which is in good agreement with $EC_{50}$ values obtained using other evaluation methods (data not shown). Thus, it is not only possible to differentiate between high and low binding but also small changes in the binding degree can be resolved with 2D-FIDA analysis according to the present invention. This is in particular important if one aims at the identification of assay inhibitors ("hits") in high throughput screening. In summary, 2D-FIDA analysis is a well-suited and highly reliable method for vesicle-based binding assays and has already been successfully applied in high throughput screening.

FIG. 20

Reference is now made to FIG. 20. According to a preferred embodiment, numbers of photon counts $\{n_i\}$ subject to determination of a histogram $\hat{P}(n)$ in step b) are derived from numbers of photon counts in primary time intervals $\{N_j\}$ by addition of numbers of photon counts from primary time intervals according to a predetermined rule. One might e.g. be interested in choosing numbers of photon counts $\{n_i\}$ subject to determination of a distribution function $\hat{P}(n)$ which are calculated from the numbers of photon counts in primary time intervals $\{N_j\}$ according to the rule $$n_i = \sum_{k=1}^{M} N_{Mi+k},$$

where M is an integer number expressing how many times the counting time interval in which $\{n_i\}$ is determined is longer than the primary time interval. Line N shows the primary time interval windows. Line $n_i$ indicates the primary time windows chosen to calculate $n_i$ according to the rule. This rule is applied to create a series of histograms with different length of the counting time interval for FIMDA.

FIG. 21

FIG. 21 shows a further embodiment in which numbers of photon counts $\{n_i\}$ are derived from predetermined primary time intervals according to a rule in which primary time intervals are separated by a time delay. In particular, the following rule can be applied:

$$n_i = \sum_{k=1}^{M} (N_{Mi+k} + N_{M(i+L)+k}),$$

where M and L are positive integer numbers, $\{n_i\}$ are numbers of photon counts subject to determination of a histogram $\hat{P}(n)$, and $\{N_j\}$ are the numbers of photon counts in primary time intervals. This rule is applied to determine different histograms for FACID.

FIGS. 22–27

Reference is now made to FIGS. 22 to 27.

The study of function and activity of cell surface receptors is central to all disciplines of modem biology and pharmacology. Membrane receptors play a key role in communication within a multicellular organism since they transduce extracellular signals across the plasma membrane into the cell. Two important classes of membrane receptors are growth factor receptors and G protein-coupled receptors (GPCR). Growth factor receptors belong to the family of receptor tyrosine kinases which play an important role in cell differentiation and growth. Receptors belonging to this class include the epidermal growth factor receptor family, the neurotrophin receptor family and insulin receptors (Mc Innes C. & Sykes B. D. Biopolymers, 43, 339–366, 1997; Riese D. J. & Stern D. F., Bioessays 20, 41–48, 1998; Persson H. & Ibanez C. F., Curr. Opin. Neurol. Neurosurg. 6, 11–18, 1993). G protein-coupled receptors are a superfamily of integral membrane proteins containing seven α-helical transmembrane domains which mediate transmembrane signal transduction of a variety of processes by binding extracellular factors such as neurotransmitters and hormones (Ji et al., J. Biol.Chem., 273, 17299–17302, 1998; Gether et al., J. Biol. Chem. 273, 17979–17982, 1998; Wess J., FASEB J. 11, 346–354, 1997).

In most cases, receptors are studied biochemically and pharmacologically wing radioligand binding assays. In these experiments, binding of radioactively labeled ligands to membrane fractions or to whole cells is monitored, frequently involving separation of bound and free ligand. Using the method according to the present invention, the characterization of fluorescently-labeled molecules or particles with respect to their molecular brightness and concentration at the single molecule level is possible. In the following it is described how this method can be applied to study ligand-receptor interactions. Bound ligand can be distinguished from unbound ligand due to the accumulation of fluorescent ligand molecules on receptor-bearing vesicles, resulting in an increased particle brightness compared to single fluorescent ligand molecules. With fluorescence intensity distribution analysis (FIDA) according to the present invention, these differences in molecular brightness can be quantified and the absolute concentrations of free and bound ligand are determined in a single measurement without the need for separation. Since FIDA takes advantage of a highly focused laser beam the detection volume is roughly the size of 1 femtoliter. The sample volumes can be reduced to 1 µl which currently is the practical limit of liquid handling, thus offering significant savings of precious biological material and chemical compounds. The results demonstrate that FIDA is an ideal method for receptor-ligand studies offering substantial benefits for research and high-throughput pharmaceutical screening: it is widely applicable, circumvents the use of hazardous and expensive radioactive probes, overcomes the need for washing steps (i.e. the present invention provides a homogeneous assay method) and enables significant reduction in reagent consumption.

Both classes of receptors described above play an important role in a large number of diseases such as cancer, neurodegenerative diseases, cardiovascular disorders and AIDS and are thus important drug targets. The EGF receptor (EGFR/ErbB1), a 170 kD receptor tyrosine kinase and the β2- adrenergic receptor, a G protein-coupled receptor as our model systems.

The following experimental protocol has been used:

Materials

Tetramethylrhodamine labelled epidermal growth factor (TMR-EGF), unlabeled epidermal growth factor (EGF) and Bodipy FL-CGP 12177 (Bodipy FL: 4,4-difluoro-5,7-dimethyl-4-bora-3a,4a-diaza-s-indacene-3-propionic acid; CGP 12177: 4-[3-[(1,1-Dimethylethyl)amino-]-2-hydroxypropxy]-1,3-dihydro-2H-benzimidazol-2-one hydro-chloride) were purchased from Molecular Probes (Leiden, Netherlands). Human epidermoid carcinoma (A431) cells and human colon carcinoma tumor (HCT) cells were obtained from the American Type Tissue Culture Collection. Betacellulin and heparin-binding EGF (HB-EGF) were purchased from R & D Systems and CGP 12177A from RBI (Natick, USA).

Methods

Cell Lines and Membrane Preparations

Wild type human β2 adrenergic receptor cDNA was cloned into the plasmid pcDNA3. The plasmid was transfected into HEK293 cells and stable clones were selected as described (Gabilondo A. M., Hegler J., Krasel C., Boivin-Jahns V., Hein L., Lohse M. J., Proc. Natl. Acad. Sci. U.S.A., 94, 12285–12290, 1997). For membrane preparations, approximately $2 \times 10^8$ cells were resuspended in 2 ml of ice cold lysis buffer (10 mM Tris-HCl pH 7.4, 1 mM $MgSO_4$, 0.5.mM EDTA containing a protease inhibitor cocktail (Complete™ Mini EDTA-free, Roche Molecular Biochemicals). Cells were disrupted by Dounce homogenization on ice and unbroken cells and nuclei were removed by centrifugation at 900×g for 10 min. The supernatants were pooled and centrifuged at 100,000×g for 20 min (4° C.). Membrane pellets were resuspended in 0.5 ml binding assay buffer and the protein concentration was determined using a Bradford protein assay (Biorad). Membranes were frozen in aliquots in liquid nitrogen and stored at −80° C.

Binding Studies

Typical experiments contained 50 to 500 µg/ml of membrane protein, different concentrations of fluorescent ligand and competitor in a final volume of 40 µl (see Figure legends for details). EGF receptor (EGFR) binding studies were carried out in 20 mM Hepes pH 7.4, 140 mM NaCl, 5 mM KCl, 1.2 mM $MgCl_2$, 1.8 mM $CaCl_2$, 0.1% BSA and 0.1% CHAPS. The binding assay buffer for the β2 adrenergic receptor contained 75 mM Tris-HCl pH 7.4, 10 mM $MgCl_2$, 2 mM EDTA, 0.05% BSA and 0.1% CHAPS. Measurements were carried out in 8 well glass chambers (Nunc). For experiments with sample volumes of 1 µl, proprietary liquid dispensing units and high-density sample carriers (Nanocarrier) with a total capacity of 1.5 µl per well were used (EVOTEC BioSystems AG).

Data Analysis

A confocal microscope was used (Confocor, EVOTEC BioSystems AG and Carl Zeiss Jena, Germany) with an optical set-up described in Kask P., Palo K., Ullmann D. & Gall K. (Proc. Natl. Acad. Sci. U.S.A., 96, 13756–13761, 1999; the contents of which are herein incorporated by reference). The number of photon counts was measured at 40 µs dwell time with a data collection time of 4–8 s per well. Measurements with TMR-EGF were carried out at excitation/emission wavelengths of 543/580 nm using a helium/neon laser attenuated to approximately 300 µW. Measurements with Bodipy FL-CGP 12177 were carried out at excitation/emission wavelengths of 488/520 nm using an $Argon^+$ laser attenuated to approximately 2 mW. Like FCS, the method according to the present invention relies on the random diffusion of fluorescent particles in and out of the confocal volume (Kask P., Palo K., Ullmann D. & Gall K., Proc. Natl. Acad. Sci. U.S.A., 96, 13756–13761, 1999; Rigler R., J. Biotechnol. 41, 177–186, 1995). Since the diffusion time of membrane particles is very high compared to single molecules such as proteins (mean diffusion time $\sqrt[4]{}$=10–100 ms versus approximately 200 µs–1 ms for single molecules), advantage was taken of a two-dimensional scanning approach, in order to be able to detect sufficiently large numbers of fluorescent membraneous vesicles. This is achieved using a laser beam oscillator and a mobile sample stage.

Assuming the presence of two different fluorescent species within the sample, namely fluorescent ligand and vesicles with fluorescent ligand accumulated on their surface, the photon count number histogram was fit with the multicomponent fit according to Kask P., Palo K., Ullmann D. & Gall K.( Proc. Natl. Acad. Sci. U.S.A., 96, 13756–13761, 1999; the contents of which are herein incorporated by reference) in order to determine molecular brightnesses and absolute concentrations of these two components. Concentrations of bound and free ligand were deduced from that data. The amount of ligand bound to vesicles is given either in concentrations (nM ligand bound) or as fractional binding (ligand bound divided by ligand total). Apparent affinities ($K_I$) were calculated from the concentration giving half-maximal displacement ($IC_{50}$, obtained by non-linear least-squares curve-fitting to a one-site binding model), using the relationship $K_I=IC_{50}/(1+$ (ligand concentration/$K_D$)) according to Cheng Y. & Prusoff W. H. (Biochem. Pharmacol. 22, 3099–3108, 1973). Experimental data were analyzed using Prism 3.0 (Graph Pad Prism, San Diego, USA).

Fluorescence intensity distribution analysis (FIDA) allows the study of molecular interactions of fluorescent molecules if a change of particle brightness occurs upon binding. Quantitative data describing molecular interactions are obtained since the molecular brightness of each fluorescent species in the sample and their respective absolute concentrations are determined. FIG. 22 shows a schematic diagram of binding of a fluorescently-labeled molecule to receptor-bearing vesicles as observed by the method according to the present invention. The confocal volume is represented by the central black square. A: In the absence of membranes, the confocal volume contains exclusively free fluorescent ligand molecules. The molecular brightness of the fluorescent ligand is an intrinsic property of the fluorophore and the molecule it is attached to. B: A brightness distribution obtained for the sample shown in A with a typical molecular brightness for free ligand of 7 kHz. C: After the addition of vesicles, ligand binding occurs and the confocal volume is populated with both vesicle-bound and free ligand. D: Brightness distribution of sample shown in C. The molecular brightness of unbound ligand remains 7 kHz. The molecular brightness of vesicles was 98 kHz in this case (14 times the brightness of free ligand, corresponding to 14 ligand molecules bound per vesicle) and depends on the receptor expression level. Typically, 10–500 ligand molecules per vesicle can be found. Note: sizes are not to scale. Thus, although the total fluorescence does not change upon binding, both the molar concentration of bound as well as the molar concentrations of unbound ligand are quantitatively determined from a single measurement without any separation being necessary.

The method according to the present invention has been used to characterize the interaction of TMR-labeled EGF with its receptor, the EGF receptor (EGFR/ErbB1). As a source, A431 cells were used which are known to overexpress EGFR (Mc Culloch et al., Int. J. Biochem. Cell Biol. 30, 1265–1278, 1998). FIG. 23 shows the ligand binding characteristics of TMR-EGF to membranes prepared from A431 cells. Ligand concentrations from 0.25–18 nM were incubated with a crude membrane fraction at a final concentration of 50 µg/ml in a total volume of 40 µl. After an incubation period of 20 min at room temperature, measurements were carried out, and free and bound ligand concentrations determined. Binding of TMR-labeled EGF to the membranes is saturable and can be competed by an excess of unlabelled EGF. Non-specific binding was determined in the presence of 1 µM EGF. The results shown are from a typical experiments, the standard deviation (SD) is shown as error bars. The determined dissociation constant ($K_D$) of 3.1±0.2 nM is consistent with earlier reports where fluorescently-labelled EGF was used as a competitor in radio-ligand binding assays (Carraway et al. J. Biol. Chem. 266, 8899–8906, 1991). An expression level ($B_{max}$) of 60 pmol/mg was observed which corresponds to approximately $6 \times 10^6$ binding sites per cell, indicating that the level of expression of EGFR in A431 is upregulated significantly as confirmed by earlier reports (Mc Culloch et al., Int. J. Biochem. Cell Biol. 30, 1265–1278, 1998).

In order to demonstrate that the method according to the present invention is also applicable to biological systems with much lower, more physiological expression levels, human colon carcinoma tumor (HCT) cells were used. FIG. 24 shows the TMR-EGF binding to membranes prepared from HCT cells. Increasing amounts of crude membranes prepared from HCT cells were incubated with 2 nM TMR-EGF in the presence and absence of unlabeled EGF. Total and nonspecific binding was determined by the method according to the present invention. Ligand bound is expressed as fractional binding (ligand bound divided by ligand total). Membranes prepared from HCT cells bind TMR-EGF, where specific binding was 70–80% of total binding. The affinity and expression levels were determined in a saturation curve as shown for A431 cells in FIG. 23 (data not shown). The $K_D$ was found to be 3 nM which is very similar to the affinity of the EGF receptor in A431 cells (see FIG. 23). The $B_{max}$ was found to be 400 fmol/mg membrane protein which corresponds to approximately 10,000–20,000 binding sites/cell and is thus more than 100 times lower than in A431 cells. This experiment demonstrates that FIDA can not only be used with receptor-overexpressing cell lines but also with receptor densities equivalent to those in their natural environment.

Since the EGF receptor is part of a family of related receptor tyrosine kinases which bind different growth factors (EGFR/ErbB-1, ErbB-2, ErbB-3 and ErbB-4; Riese et al. Bioessays 20, 41–48, 1998) the interaction of TMR-EGF with HCT membranes has been further characterized. The number of mammalian polypeptide growth factors exhibiting significant sequence identity with EGF has increased dramatically in recent years and include betacellulin and heparin-binding EGF (HB-EGF). FIG. 25 illustrates the pharmacological profile of the EGF receptor. The affinity of unlabelled EGF, betacellulin and heparin-binding epidermal growth factor (HB-EGF) was determined by competition assays incubating HCT membranes with TMR-EGF and the indicated concentrations of competitor. Binding was determined by the method according to the present invention and was normalized to that in the absence of competitor. The affinities obtained were 0.35±0.12 nM for EGF, 0.23±0.02 nM for betacellulin and 1.4×0.3 nM for HB-EGF.

As a further system, the β2 adrenergic receptor was used since it is a well known model system for the large family of G protein-coupled receptors (Kobilka, Annu. Rev. Neurosci. 1587–114, 1992). Fluorescently-labeled CGP 12177, a β2 adrenergic receptor antagonist, was chosen as a ligand (Heithier et al., Biochemistry 33, 9126–9134, 1994). FIG. 26 illustrates the ligand binding characteristics of Bodipy FL-CGP 12177. Increasing concentrations of Bodipy FL-CGP 12177 were incubated with a crude membrane fraction derived from HEK 293 cells expressing the human β2 adrenergic receptor. The final membrane concentration was 130 µg/ml in a total volume of 40 µl. Non-specific binding was determined in the presence of 1 µM propranolol and was subtracted from total binding. The results shown are from a typical experiments, standard deviations (SD) are shown as error bars. Bodipy FL-CGP 12177 bound to an apparently homogenous population of binding sites. Binding of the ligand was statistically best fit using a single site model with a mean affinity of 0.7 nM, which is similar to the results obtained when using standard filter binding assays (Heithier et al., Biochemistry 33, 9126–9134, 1994), and a $B_{max}$ of 4 pmol/mg. Competition experiments with unlabelled CGP 12177 yielded a $K_I$ of 0.8 nM, indicating that the attachment of the fluorescent label does not affect the affinity for the receptor significantly.

FIG. 27 illustrates the inhibition of Bodipy FL-CGP 12177 binding in 40 µl and 1 µl assay volumes. Unlabelled ligand (CGP 12177A) was used as a competitor at the concentrations shown. Binding was normalized to 100% at maximal binding. The binding assay was carried out in sample volumes of 40 µl and 1 µl. For experiments involving sample volumes of 1 µl, proprietary liquid dispensing units and sample carriers were used (EVOTEC BioSystems AG). The affinities obtained for CGP12177 were 0.7±0.1 nM in 40 µl and 0.9±0.1 in 1 µl assay volumes. This experiment emphasizes the unique sensitivity of FIDA and poses a large opportunity for a significant reduction of sample volumes and thus of the required biological material for high-throughput drug screening.

Studying ligand-receptor interactions is an important tool for the biological and pharmacological characterization of membrane receptor function. Particularly, G protein-coupled receptors are of high interest for pharmaceutical drug discovery programs since approximately 30–50% of all drugs on the market today are estimated to act on GPCR (Gudermann et al. J. Mol. Med. 73, 51–63, 1995). Traditionally, the majority of ligand-receptor studies are carried out using radioactively-labeled ligands, where bound from unbound ligand is separated by either filtration or centrifugation. In recent years, scintillation proximity assays have found widespread use for receptor-ligand binding studies. Here, binding events are detected by the proximity of the radioligand to membranes immobilized on a scintillant-containing bead, thus eliminating the need for separation (Hart, Mol. Immunol. 16, 265–267, 1979). However, the disadvantages of these methods are potentially hazardous exposure to radioactive compounds, limited shelf half-life of labeled ligands and special requirements for handling and disposal of reagents. Therefore, a number of fluorescence-based detection methods have been applied to receptor-ligand studies in recent years which are based on the detection of total fluorescence (Heithier et al, Biochemistry 33, 9126–9134, 1994; Inglese et al. Biochemistry 37, 2372–2377, 1998), fluorescence quenching/spectral shift (Tairi et al., Biochemistry 37, 15850–15864, 1998), fluorescence polarization (Tairi et al., Biochemistry 37, 15850–15864, 1998) or on the use of laser-scanning imaging (Zuck et al. Proc. Natl. Acad. Sci. USA, 11122–1127, 1999).

Based on the method according to the present invention, fluorescence intensity distribution analysis can be used to characterize quantitatively the interaction of ligands with their cognate receptors. Since FIDA allows interactions to be studied with single molecule sensitivity, it offers significant advantages over the methods described above. Using EGF and β2 adrenergic receptors as model systems it has been shown in the examples above that affinities and receptor expression levels can be quantitated in a simple manner. The results demonstrate that the pharmacological profiles obtained using FIDA correspond to those obtained by classical radioligand binding assays. It has also been shown that FIDA can be used to study ligand-receptor interactions using cells expressing low levels of receptor. This is of particular importance for GPCRs since they are typically found in low density in primary tissues and overexpression of functional receptors is often difficult to achieve. Since FIDA allows to quantitate the increase in particle brightness upon binding of multiple fluorescent molecules to vesicles, no changes of fluorescence parameters such as fluorescence quenching or spectral shift are required to occur, making this approach widely applicable. With FIDA, molar concentrations of both free and bound ligand are determined in a single measurement thus providing an internal control as to how much total ligand is present in each sample. A significant advantage of FIDA using a confocal optical set-up is the small volume of detection, which is approximately the size of a bacterial cell. Miniaturization of assay volumes is a key strategy in modern pharmaceutical drug screening since increasing numbers of chemical compounds have to be screened against a growing number of biological targets, consumption of biological reagents and of chemical or natural compounds therefore becomes a major issue. FIDA and related preferably confocal methods based on the present invention are therefore ideally suited for these purposes since the sample volume can be reduced to 1 µl, which is the current limit of liquid handling, without compromising the signal-to-noise ratio, therefore offering unique sensitivity.

FIDA has been successfully applied to study a number of different types of G protein-coupled receptors in our laboratory. These include chemokine receptors, dopamine receptors and a number of peptide receptors. These assay systems include the usage of small labeled molecules (agonists or antagonists such as described in this study), peptides and proteins (data not shown). In addition, the technology can be successfully applied to measure binding of molecules to live cells in a 1 µl format. This opens the exciting opportunity of using primary tissues directly in high-throughput screening. In conclusion, FIDA is an ideal method for ligand-receptor studies: It offers significant advantages for research, high-throughput screening and for pharmacological profiling since it circumvents the use of radioactive isotopes and of separation steps, is widely applicable and it allows a significant reduction of reagent consumption.

FIGS. 28–30

A further example was based on the global analysis of a set of photon count number histograms, recorded with multiple widths of counting time intervals simultaneously. The counting time intervals can be determined according to the procedure described in FIG. 20. This Fluorescence Intensity Multiple Distribution Analysis (FIMDA) distinguishes between fluorescent species on the basis of both, the specific molecular brightness and the translational diffusion time. The combined information, extracted from a single measurement, increases the read-out effectively by one dimension and thus breaks the individual limits of FCS and FIDA. The method can be widely applied for monitoring molecular interactions including receptors and ligands or antibodies and antigens, which are both of great relevance in the life sciences.

In the following, a modification of the theory of FIDA, which is a suitable approximation for our experimental purposes, is presented. In FIDA, a convenient representation of a photon count number distribution P(n) is its generating function, defined as $$R_{P(n)}(\xi) = \sum_n \xi^n P(n). \tag{41}$$

The theory of FIDA assumes (i) that molecules are immobile during the counting time interval, and (ii) that the light flux from a molecule can be expressed as a product of a spatial brightness function B(r) (this is a function of spatial coordinates of the molecule characterizing the equipment) and a specific brightness q (characterizing a certain molecule species). Under these two assumptions, the distribution of the number of photon counts, emitted by molecules from a volume element dV, is double Poissonian and the corresponding generating function reads $$R_{P(n)}(\xi) = \exp[cdV(e^{(\xi-1)qB(r)T} - 1)], \tag{42}$$

where ξ is the complex argument of the generating function, c is the concentration of molecules, and T is the width of the counting time interval. This representation is convenient, because contributions from independent sources, like different volume elements or species, are combined by multiplication of the contributing generating functions. The generating function of P(n) for a single species is $$R_{P(n)}(\xi) = \exp[c \int (e^{(\xi-1)qB(r)T} - 1) dV], \tag{43}$$

while accounting for multiple species simply yields $$R_{P(n)}(\xi) = \exp\left[\sum_i c_i \int (e^{(\xi-1)q_i B(r)T} - 1) dV\right]. \tag{44}$$

The integral on the right hand side of Eq. 44 is calculated numerically, but instead of the three-dimensional integration over spatial coordinates, a one-dimensional integration coordinate $x=\ln[B_0/B(r)]$ is introduced. The relationship between the brightness B and the coordinate x is therefore $B(x)=B^0 e^{31\ x}$. In FIDA it has been found suitable to express the function dV/dx, which describes the brightness profile in one-dimensional representation, by the formula:

$$\frac{dV}{dx} = A_0(x + a_1 x^2 + a_2 x^3). \quad (45)$$

Here $a_1$ and $a_2$ are empirical adjustment parameters granting for a sufficient flexibility to fit the measured histograms with high precision. The selection of coefficients $A_0$ and $B_0$ is nothing but the selection of the units of V and B. Usually, they are determined from the conditions $$\int B dV = 1, \quad (46)$$

$$\int B^2 dV = 1. \quad (47)$$

So far, a simple version of the theory of FIDA has been described. For the purposes of FIMDA, the assumption that molecules are immobile during the counting interval has to be abandoned. Surprisingly, Eq. 42 will not be abandoned, as well as the following equations, but the meaning of some variables will be instead. x is still a variable related to the spatial brightness profile, but now it characterizes the path of the molecule rather than its position. B is the spatial brightness averaged over the path rather than determined at a fixed position of the molecule. V is not the volume in space but dV/dx still expresses the probability that a molecule has a given value of x. If the original meaning of c and q would be kept, a theory predicting how $A_0$, $a_1$ and $a_2$ depend on the counting time interval T would have to be developed. However, another approach has been chosen. The normalization conditions were kept (Eqs. 46 and 47). It is even possible to apply a single selection of the values $A_0$, $a_1$ and $a_2$ for a set of different time windows. The consequence of this selection is that in Eqs. 42–44 c is an apparent concentration ($c_{app}$) and q is an apparent brightness ($q_{app}$) which both depend on the width of the counting time interval T.

In the following, a theory is presented predicting how $c_{app}$ and $q_{app}$ depend on T. The case of single species is studied and the first and the second factorial cumulants of the distribution corresponding to Eq. 43 are calculated. The factorial cumulants are defined as $$K_n = \left(\frac{\partial}{\partial \xi}\right)^n \ln(R(\xi))|_{\xi=1} \quad (48)$$

yielding:

$$K_1 = \langle n \rangle = c_{app} q_{app} T, \quad (49)$$

$$K_2 = \langle n(n-1) \rangle - \langle n \rangle^2 = c_{app} q_{app}^2 T^2, \quad (50)$$

where normalization conditions given by Eqs. 46 and 47 have been used. (Note that Eqs. 49 and 50 are in total agreement with Qian and Elson's formulae (Biophys. J. 57: 375–380, 1990) derived under the assumptions i and ii.) From Eq. 49 one can conclude that $$c_{app}(T) q_{app}(T) = \langle I \rangle, \quad (51)$$

where $\langle I \rangle \equiv \langle n \rangle_T/T$ is the mean count rate, which does not depend on the choice of T. We shall proceed by employing the following relationship between the second cumulant of the count number distribution P(n;T) and the autocorrelation function of fluorescence intensity $G(t) = \langle I(0)I(t) \rangle - \langle I \rangle^2$, $$\langle n(n-1) \rangle_T - \langle n \rangle_T^2 = \int_0^T dt_1 \int_0^T dt_2 G(t_2 - t_1). \quad (52)$$

Introducing the notation $$\Gamma(T) = \frac{1}{cq^2 T^2} \int_0^T dt_1 \int_0^T dt_2 G(t_2 - t_1), \quad (53)$$

from Eqs. 52 and 50 is derived $$c_{app}(T) q_{app}^2(T) = c q^2 \Gamma(T). \quad (54)$$

From Eqs. 51 and 54 one gets $$q_{app}(T) = q \Gamma(T), \quad (55)$$

$$c_{app}(T) = \frac{c}{\Gamma(T)}. \quad (56)$$

As the concluding step, expressions of G(t) from FCS were substituted into Eq. 43. If a Gaussian brightness function is applied and triplet trapping is ignored (Aragón and Pecora, J. Chem. Phys. 64: 1791–1803, 1976) then $$G_{diff}(t) = cq^2 \left(1 + \frac{D|t|}{\sigma_r^2}\right)^{-1} \left(1 + \frac{D|t|}{\sigma_z^2}\right)^{-1/2}, \quad (57)$$

denoting $\sigma_r$ as the radial and $\sigma_z$ as the longitudinal distance, where the Gaussian profile has dropped $e^{1/2}$ times. The integrals in Eq. 53 yield $$\Gamma_{diff}(t) = \frac{4}{t^2 \beta \sqrt{1-\beta}} \left[\beta(1+t)\mathrm{artanh}\left(\frac{\sqrt{1-\beta}(\sqrt{1+\beta t}-1)}{\beta + \sqrt{1+\beta t}-1}\right) - \sqrt{1-\beta}(\sqrt{1+\beta t}-1)\right], \quad (58)$$

where $t=DT/\sigma_r^2$ and $\beta=\sigma_r^2/\sigma_z^2$. For reasons explained below it is useful to calculate the first order terms in Eq. 58:

$$\Gamma_{diff}(T) = \left[1 + \frac{DT}{6}\left(\frac{2}{\sigma_r^2} + \frac{1}{\sigma_z^2}\right)\right]^{-1} + O(D^2). \quad (59)$$

However, from theoretical considerations as well as from measurements it is known that simple physical models like Gaussian or else Gaussian-Lorentzian do not exactly represent the actual brightness profile (Kask et al., Proc. Natl. Acad. Sci. USA, 96, 13746–13761, 1999). Therefore, Eq. 59 has been modified and a fitting parameter a has been introduced, that preserves the first order terms in Eq. 59:

$$\Gamma_{diff}(T) \approx \left[1 + \frac{DT}{6a}\left(\frac{2}{\sigma_r^2} + \frac{1}{\sigma_z^2}\right)\right]^{-a}. \quad (60)$$

By matching the second order terms the Gaussian brightness profile would correspond to a=2/3, but rather a was chosen to be an empirical parameter, which is determined by the fining procedure.

Another phenomenon involved is that of intensity fluctuations due to trapping of molecules into a triplet excited state (Widengren et al., J. Phys. Chem. 99:13368–13379; 1995). To obtain a good fit, particularly at values of T comparable to the triplet lifetime (which is typically 2 μs), an additional factor is introduced into G(t):

$$G_{trip}(t) = \frac{1 + \kappa\tau \exp\left(-\frac{(1+\kappa\tau)t}{\tau}\right)}{(1+\kappa\tau)^2}, \quad (51)$$

where κ is the singlet to triplet transition rate and τ is the triplet lifetime. Eq. 51 yields $$\Gamma_{trip}(T) = \frac{\left\{2\frac{\tau}{T}\kappa\tau\left[1+\kappa\tau - \frac{\tau}{T}\left(1 - e^{\frac{T}{\tau}(1+\kappa\tau)}\right)\right] + (1+\kappa\tau)^2\right\}}{(1+\kappa\tau)^4}. \quad (52)$$

Unlike diffusion, that influences only higher cumulants of photon count numbers, triplet corrections also shift the first cumulant by the factor $1/(1+\kappa\tau)$.

$$q_{app}^{(trip)}(T) = q\Gamma_{trip}(T)(1+\kappa\tau), \quad (53)$$

$$c_{app}^{(trip)}(T) = \frac{c}{\Gamma_{trip}(T)(1+\kappa\tau)^2}. \quad (54)$$

After having derived these expressions for $c_{app}$ and $q_{app}$ (including the triplet factor), the data simulations and the experiments should verify their validity.

The following experimental protocol has been used.

Experimental set-up

The central optical part of a FIMDA experiment is a confocal microscope as it is used in fluorescence correlation spectroscopy (Koppel et al., Biophys. J. 16:1315–1329, 1976; Rigler et al., Eur. Biophys. J. 22:169–175, 1993a). For the excitation of fluorescence, a beam from a continuous wave laser is attenuated to ~800 μW by neutral density filters, passes a beam expander, and is directed to the microscope objective by a dichroic mirror. Fluorescence is collected by the same objective through the dichroic mirror, a spectral band-pass filter, and is focused to a confocal pinhole, which serves to reject the out-of-focus light. The light, which passes the pinhole, is detected by a silicon photon counting module (SPCM-AQ-131, EG&G Optoelectronics, Vaudreuil, Canada). An electronic counter, constructed at EVOTEC as a computer plug-in card, collects the TTL pulses from the detector continuously and calculates the count number histograms for all preselected widths of time windows (40, 60, 120, 200, 400, 600, 800, 1200, 1600, 2000 μs) in real-time from the 32 MB onboard buffer. By feeding the detector outputs to a correlator, FCS measurements can be performed in parallel with FIMDA experiments.

In order to satisfy the spectral needs of the various fluorophores used in this study, different lasers and spectral band-pass filters were employed. For Cy5 (Amersham Pharmacia Biotech, Bucks, UK) conjugated bio-molecules an arrangement of a red laser diode (Crystal GmbH, Berlin, Germany; 635 nm) and a band-pass filter with a central wavelength of 670 nm (670DF40, Omega Optical, Brattleboro, VI) was used. In case of TAMRA (5-carboxytetramethylrhodamine) labeled molecules this was an arrangement of a frequency doubled Nd-YAG laser (μgreen 4601; Uniphase, San Jose, Calif.; 532 nm) and a 590DF60 filter.

The focal beam radius was adjusted to ~0.75 μm by selecting an appropriate expansion factor of the original laser beam, resulting in a mean translational diffusion time of 360 μs for the free dye Cy5. This diffusion can be clearly observed when rising the time windows from 40 μs to 2 ms. As can be seen in FIG. 28, the selected count number histograms of a 0.8 nM Cy5 solution differ considerably. However, the major differences between the shape of distributions are due to the varying mean count number with the length of the counting time interval. Diffusion of fluorescent molecules causes only small but yet significant modifications to the shape of each distribution.

The levels of background count rate are generally determined in a separate experiment on bidistilled water and amount usually to 0.5 kHz. The main contributor to this non-fluctuating background light intensity is Raman scattering from water.

Data Simulations

Instead of preparing real samples, comprising a mixture of molecules, which express deliberately chosen parameters (brightness values and diffusion coefficients), some evaluations of the new method were performed using simulated data. A number of sets of histograms for FIMDA, FIDA and correlation functions for FCS have been simulated according to the following algorithm. In a closed rectangular reservoir, a given number of molecules is initially randomly distributed over a high number (typically 360×360×720) of discrete spatial grid points. Each molecule is subject to consequent diffusion simulation and jumps randomly by one grid unit either in x-, y- or z-direction with a frequency corresponding to a given diffusion coefficient. The "focus" is located in the center of the reservoir, and the brightness distribution is assumed to be Gaussian in all three dimensions. When calculating the brightness integral from a molecule over a given set of time intervals, the molecule can be randomly trapped, as well as released from the triplet excited state (where it is dark). Now one can calculate an array of brightness integrals over basic time intervals of a given width (e.g. 5 μs) describing the evolution of the mixture. The brightness integrals are then converted into photon count numbers, which subsequently were used to calculate histograms for FIMDA, FIDA, as well as the correlation function for FCS.

Due to the finite site of the simulation reservoir, some distortions of the correlation function (i.e., deviations from Eq. 57) can be expected. The distortions are in fact below the statistical noise level. Therefore the simulations were considered to be an adequate tool for estimating statistical errors of the extracted parameters. For this purpose, typically 30 realizations of experiments with a given set of molecular parameters were simulated, from which the standard deviations and the coefficients of variation (CV) as the ratio of standard deviation to mean value were calculated.

Biochemical System

The Grb2 (SH2)-phosphopeptide Interaction

Recent antitumor research has been focused on tyrosine kinase growth factor receptors (Levitzki, Eur. J. Biochem. 226:1–13, 1994; Alessandro et al., Curr. Top. Microbiol. Immunol. 213:167–188, 1996; Furet et al., J. Med. Chem. 41:3442–3449, 1998). A critical link in the signal transduction pathway of this receptor is the interaction of its phosphotyrosine residue (pTyr) with the Src-homology 2 (SH2) domain of the adapter protein Grb2 (growth factor receptor-binding protein 2). For the recognition a minimal peptide sequence of the receptor (pTyr-Val-Asn) is sufficient (Müller et al., J. Biol. Chem. 271:16500–16505, 1996; Gram et al., Eur. J. Biochem. 246:633–637, 1997; Furet et al., J. Med. Chem. 41:3442–3449, 1998). The binding partner of this peptide motive, the SH2 domain of Grb2, can fold into a functional protein module independent of neighboring sequences (Booker et al., Nature 358:684–687, 1992; Overduin et al., Cell 70:697–704, 1992). Therefore, as a model system, we have chosen the bare SH2 domain (14.3 kDa) to interact with a fluorescently labeled phosphopeptide (pTyr-Val-Asn-Val-Lys(Cy5)) (1387 Da).

The SH2 domain of Grb2 was prepared as described elsewhere (Lowenstein et al., Cell 70:431–442, 1992; Baumann et al., Eur. J. Immunol. 24:1799–1807, 1994; Müller et al., J. Biol. Chem. 271:16500–16505, 1996). The phosphopeptide was synthesized using manual Fmoc solid phase chemistry and labeled with Cy5-NHS via a Lysine residue. An additional Valine was introduced to minimize possible interactions of the dye with the main recognition motive pTyr. The final compound, pTyr-Val-Asn-Val-Lys(Cy5) was characterized by mass spectrometry (LC/MS, and MALDI/TOF), UV/VIS, and fluorescence spectroscopy.

The following results were obtained.

Data Simulations and Test Experiments

At first, a series of measurements on a 1 nM TAMRA solution was performed collecting data in parallel for FIMDA as well as for FCS. This series of experiments, with duration of 2 s each, was repeated in simulations using similar molecular parameters. The purpose of these experiments was to verify whether simulations are a reasonable model of real experiments, in particular whether data simulations are a reasonable means of predicting statistical errors of estimated parameters. The coefficients of variation of the parameters extracted from simulated data indeed coincide with the results of the real experiment, as can be seen in Tab. 7.

TABLE 7

Comparison of coefficients of variation of estimated parameters from series of experimental and simulated histograms by FIMDA, and correlation functions by FCS.

| | | CV (%) | | | |
|---|---|---|---|---|---|
| | | FIMDA | | FCS | |
| Parameter | Mean value | Experimental data | Simulated data | Experimental data | Simulated data |
| Brightness q (kHz) | 52 | 1.8 | 1.6 | 1.7 | 2.0 |
| Concentration c (molecules per confocal volume) | 0.7 | 1.6 | 1.8 | 1.7 | 2.4 |
| Diffusion time $\tau$ ($\mu$s) | 64 | 3.5 | 3.4 | 4.1 | 3.9 |

Another series of test experiments was repeated in a significantly shorter time domain with the goal to compare FIMDA and FCS in their ability to estimate parameters of the triplet component. A set of counting time intervals of 2, 4, 8, 16, 32, 64, 128, 256, 512, and 1024 $\mu$s was selected for this purpose. The duration of these experiments was 16 s. The results, presented in Tab. 8, indicate that the values for the triplet parameters estimated by FIMDA have similar dependence on the excitation intensity to the FCS results.

TABLE 8

Triplet parameters, estimated from a series of experiments on 1 nM TAMRA solution by FCS and FIMDA at two different excitation intensities. Excitation wavelength 532 nm, duration 16 s, time windows 2, 4, 8, 16, 32, 64, 128, 256, 512, and 1024 $\mu$s.

| Peak excitation intensity, (kW/cm$^2$) | FCS | | | | FIMDA | | | |
|---|---|---|---|---|---|---|---|---|
| | Triplet lifetime ($\mu$s) | CV (%) | Triplet population | CV (%) | Triplet lifetime ($\mu$s) | CV (%) | Triplet population | CV (%) |
| 118 | 1.98 | 3.9 | 0.182 | 2.7 | 3.12 | 7.6 | 0.137 | 3.1 |
| 187 | 1.75 | 3.7 | 0.235 | 1.6 | 2.59 | 3.8 | 0.183 | 2.0 |

The FIMDA results are slightly biased and have higher CV values compared to FCS, since the estimation of triplet parameters in FIMDA is indirect, because the shortest time window (2 $\mu$s) is equal to the triplet lifetime. However, the main purpose of the triplet correction in the model is not to determine the triplet parameters, but to improve the quality of the fit and to remove a source of bias in the brightness and diffusion parameters.

Histograms for FIMDA for three-component analysis have also been simulated. Two of the components had equal brightness values (120 kHz), and another pair had equal diffusion times (192 $\mu$s). Due to the larger number of free parameters, the simulated duration of experiments was increased to 60 s, so that the variations of fitted parameters stayed in reasonable limits. In this test all parameters were subject to fitting. The results are presented in FIG. 29 as vertical bars in a plane with brightness and diffusion time as x-y coordinates, and the ordinate displaying the contribution to the intensity, i.e., the product of concentration and brightness. The three components are clearly resolved, since the scatter in the location of individual bars is much smaller than the distance between the groups, which correspond to different components. Note that with FIDA alone, the components with equal brightness cannot be resolved, while with FCS alone, the components with equal diffusion time remain unresolved.

Biochemical System

The experimental utilization of the new method shall now be demonstrated by the determination of the binding constant of the above introduced Grb2 (SH2)-phosphopeptide interaction. For this purpose a titration experiment was carried out keeping the pTyr-Val-Asn-Val-Lys(Cy5) concentration constant at 0.4 nM, while SH2 was subject to titration (0.01, 0.03, 0.1, 0.3, 1, 3, 10, 30, 100, and 130 $\mu$M). All experiments were performed under identical conditions, i.e., the same buffer (sterile filtered water, 50 mM Na-phosphate buffer pH 7.8, 50 mM NaCl and 0.05% Pluronic; T=20° C.), and a data acquisition time of 30 s per measurement, repeated 30 times per sample. In each single measurement the same set of 10 different time windows was used (40, 60, 120, 200, 400, 600, 800, 1200, 1600, 2000 $\mu$s) resulting in 10 different photon count number histograms, which were globally fitted.

As the first step, the diffusion time $\tau_1$=407±6 $\mu$s and the molecular brightness $q_1$=31.7±0.3 kHz were determined from a single component analysis applied to the pure conjugate solution. Addition of excess SH2 (130 $\mu$m) to 0.4 nM conjugate resulted in a sample with the majority of the conjugate bound to SH2. The complex was characterized both by a longer diffusion time and a higher molecular brightness compared to the free conjugate. This mixture was then analyzed by all three methods (FIMDA, FIDA and FCS) using a two-component fit with $\tau_1$ and/or $q_1$ fixed, depending on the method. The results of this step of analysis are presented in Tab. 9. It can be seen that all methods yield similar values of parameters. The corresponding CV values were again determined by two independent methods, i.e. from the statistical analysis of the results of a series of 30 measurements and from simulations. The two estimates of the statistical errors agree reasonably well and the CV values corresponding to different methods are similar, with the exception of FIDA, which has difficulties due to the small (30%) difference in brightness values of the components. The relative error of the estimated concentration of the conjugate is high because the other component dominates in this sample.

TABLE 9

Comparison of estimated parameters and their coefficients of variation at a high receptor concentration (130 µM). A series of 30 experiments of 30 s duration each was evaluated by FIMDA, PIDA and FCS. Brightness (in FIMDA and FIDA) and diffusion time (in FIMDA and FCS) of the free conjugate were independently determined and fixed to 31.7 kHz and 407 µs, respectively, in this analysis.

| Parameter | Method | Mean value from experiment | CV (%) | CV (%) from simulations |
|---|---|---|---|---|
| $c_{conjugate}$ (molecules per confocal volume) | FIMDA | 0.132 | >20 | >20 |
| | FIDA | 0.196 | >20 | >20 |
| | FCS | 0.052 | >20 | >20 |
| $c_{complex}$ (molecules per confocal volume) | FIMDA | 0.618 | 9.6 | 8.0 |
| | FIDA | 0.555 | 26.7 | 14.9 |
| | FCS | 0.710 | 7.9 | 12.6 |
| $q_{complex}$ (kHz) | FIMDA | 39.5 | 2.2 | 2.3 |
| | FIDA | 38.4 | 5.5 | 3.9 |
| | FCS | 36.4 | 3.7 | 3.4 |
| $\tau_{complex}$ (ms) | FIMDA | 0.913 | 6.9 | 4.6 |
| | FCS | 0.898 | 5.4 | 7.2 |

As the next step of the studies, a sample with 3 µM SH2 was analyzed. This particular concentration was chosen to achieve a mixture of approximately equal proportions of complex and free conjugate. Since it is rather difficult to resolve components with only a twofold difference in diffusion coefficient and even smaller difference in specific brightness, here also the diffusion time and brightness of the complex were fixed to the values of Tab. 9. With the molecular parameters fixed, the concentrations were reliably resolved by all methods. The results of this step of analysis are summarized in Tab. 10.

TABLE 10

Comparison of the estimated concentrations at an intermediate receptor concentration (3 µM). In addition to the brightness and the diffusion time of the free conjugate, also the brightness and/or the diffusion time of the complex were fixed here to values shown in Tab. 9.

| Parameter | Method | Mean value from experiment | CV (%) | CV (%) from simulations |
|---|---|---|---|---|
| $c_{conjugate}$ (molecules per confocal volume) | FIMDA | 0.328 | 11.7 | 4.9 |
| | FIDA | 0.311 | 16.1 | 4.9 |
| | FCS | 0.303 | 8.4 | 8.0 |
| $c_{complex}$ (molecules per confocal volume) | FIMDA | 0.437 | 8.2 | 3.4 |
| | FIDA | 0.455 | 10.0 | 3.7 |
| | FCS | 0.467 | 7.8 | 8.8 |

In the same manner, the whole series of SH2 concentrations was fitted. FIG. 30 shows the calculated fraction bound ($c_{complex}/(c_{complex}+c_{conjugate})$) for FIMDA with the solid curve resulting from a hyperbolic fit, that yielded a binding constant for the SH2-phosphopeptide interaction of $K_D$=1.68±0.27 µM. Comparable binding curves were also obtained by FCS and FIDA (data not shown), with $K_D$ values of 2.26±0.28 µM and 1.70±0.29 µM, respectively.

The data of FIG. 30 demonstrate that FIMDA is a suitable method for monitoring the formation of a molecular complex. FCS and FIDA experiments yielded similar $K_D$ values for this particular SH2-phosphopeptide interaction. In the literature the affinity is reported to vary by several orders of magnitude, depending on the peptide sequence (Müller et al., J. Biol. Chem. 271:16500–16505, 1996; Gram et al., Eur. J. Biochem. 246:633–637, 1997; Furet et al., J. Med. Chem. 41:3442–3449, 1998). High affinities are in the range of $K_D$=10–100 nM. However, with a lysine (and Cy5 attached to it) at the +4 position of the phosphopeptide (defining p-Thr as the 0 position with "+" continuing on the C and "−" on the N terminus) the affinity decreases to the micromolar range. This result agrees well with the importance of lipophilic groups attached to 'appropriate' positions on the C-terminus, increasing the binding constant to the SH2-domain (Furet et al., J. Med. Chem. 41:3442–3449, 1998). For example Val (at position pTyr+3) is making van der Waals contact with a large hydrophobic area on the SH2-domain.

One of the surprising results of this study is that in each of the experiments, the statistical accuracy of the diffusion time estimated by FIMDA is as good as or even better than that estimated by FCS. This is a counter-intuitive result because FCS is directly focused on fitting a diffusion-dependent correlation function G(t), while in FIMDA the diffusion time is estimated only indirectly, namely through the dependence of the apparent brightness on the width of the time window.

A further observation in this respect is that the CV values for the diffusion times are in general higher than those for the brightness values. This also holds true for the theoretical simulations and therefore reflects an effect rooting in the measuring principle. The phenomenon can be explained qualitatively by the different ways how these quantities are determined. For simplicity, one may imagine an observation volume with a constant brightness profile B(r) inside. In this case, one only needs to measure the average count rate of a molecule that enters the volume to determine its specific brightness. This requires the detection of many photons per given time interval but can in principle be achieved from a single passage. On the other hand, for estimating the diffusion time, one has to determine the mean duration of the diffusion driven passage, which inevitably requires averaging over many events, even though many photons may be detected each time. Therefore, in an experiment of fixed duration, the specific brightness of a molecule can in principle be determined with a higher accuracy than its diffusion time.

The advantage of FIMDA and FIDA over the prior art FCS is that both methods yield genuine concentrations of components in the sample, instead of the products of concentration and brightness squared in FCS. Only the independent determination of at least one of the two molecular brightness values enables FCS to resolve two concentrations unambiguously, as it was done in the examples above. However, inexperienced users of FCS often silently assume equal molecular brightness when resolving two components. This assumption can cause significantly biased results. According to the present invention, FIDA and FIMDA bring this issue to the focus of analysis.

Another advantage of the presented embodiment is its versatility. If FCS or FIDA fail to detect a particular readout upon a biochemical reaction, FIMDA might be able to succeed. The biochemical reaction is not necessarily limited to the binding of two components, but can be any chemical reaction of interest. Using only one detector for recording two physical characteristics in a single measurement makes FIMDA a very efficient method of analysis which saves precious assay development time.

FIGS. 31–33

In a further experiment the method according to the present invention has been applied for rapid and quantitative screening of monoclonal antibodies directly on hybridoma cell-surfaces. An expanding market for monoclonal antibodies in clinical diagnostics and as therapeutic drugs is continuously driving the need for a faster and more quantitative method to detect and isolate antigen-specific hybridoma. Currently, efficient screening of hybridoma cell fusions is limited by the fact that the specificity and affinity of the secreted monoclonal antibody are determined in time- and labor-intensive procedures.

A confocal fluorescence-based approach is described in following where these parameters are determined in a homogeneous binding assay for antibody molecules which have not yet been released into the culture medium, but are still physically linked to the surface of the producing hybridoma cell. Combining this direct cellular binding assay with fluorescence-intensity distribution analysis (FIDA), the dissociation constant ($K_D$) of theophylline- and a β-amyloid-specific monoclonal antibodies could be determined directly on the surfaces of the corresponding hybridoma cells. This highly sensitive confocal screening approach offers a powerful technology to accelerate the isolation of antigen-specific clones amongst heterogeneous hybridoma cell populations.

Although the general technique of producing hybridoma cell lines is well established, there is still considerable time and effort involved in screening and selecting monospecific clones having a reasonable affinity for a given antigen. Following the immunization of mice and the fusion of splenocytes and a murine myeloma cell line, a major limiting step is the detection and isolation of individual hybridoma clones amongst the heterogenous population of mostly non-functional hybrid cells. In general, the cells producing the antibody of interest are cloned in soft agar or by limited dilution in multi-well plates to ensure monoclonality. The culture supernatants of the hybridoma clones are then characterized for the presence of the desired antibody by enzyme-linked immunosorbent assays (ELISAs). Using these established antibody production methods, an effective screening of large cell populations is limited in two major ways. First, the applied heterogeneous detection assays are lengthy multi-step procedures providing no exact data on the affinity ($K_D$) of the produced antibody. Second, these assays are rather insensitive and require a relative high concentration of antibody molecules in the culture supernatant which cannot be produced by a single hybridoma cell. Thus, to detect and isolate antigen-specific hybrid clones, a time-consuming cultivation of the fused cell lines is required, limiting the screening to a few hundred clones.

Alternative strategies have been described, where conventional fluorescence-activated cell sorter (FACS) technology has been applied as a means for selective cloning of hybridoma cells based on surface Ig expression. The amount of immunoglobulins has been determined using fluorescence tagged antigen either directly on the hybridoma surface (Marder P. et al., Cytometry 11:498–505, 1990; Meilhoc E. et al., J. of Immunol. Methods 121:167–174, 1989) or the secreted antibodies were artificially arrested to the cell (Manz R. et al., Proc. Natl. Acad. Sci. 92:1921–1925, 1994; Weaver J. C. et al, Nature. Medicine 3:583–585, 1997). In several investigations, the cell-bound Ig could be correlated with the hybridomas capacity to secrete monoclonal antibody into cell culture medium (Sen S. et al., Enzyme Microb. Technol. 12:571–576, 1990). As a major draw-back, these approaches employed heterogeneous assays providing no information on the binding affinity of the produced monoclonal antibody.

According to the present invention, a straightforward strategy based on a homogeneous immunoassay is presented where confocal fluorescence microscopy was applied to monitor the interaction of fluorescently labeled antigens with their complementary monoclonal antibody directly on the hybridoma cell surface. When compared to soluble antibody molecules which are secreted into the large volume of the culture medium, the surface-arrested antibody fraction generates a much higher local concentration on the hybridoma cell within a shorter time period. It is possible to determine simultaneously the concentration and brightness values of different fluorescent species like single molecules and particles (cells or beads). Upon binding of fluorescently labeled antigens to antibodies displayed on the hybridoma cell surface, the brightness of the complex increases with the number of bound antigens. The complexes can then be distinguished accurately from free antigen and concentrations of free and bound molecules can be determined quantitatively. For a model hybridoma cell line, producing monoclonal antibodies directed against the small hapten theophylline, the $K_D$-values of the surface-bound antibody were determined. With fluorescence correlation spectroscopy (FCS) measurements performed in parallel, comparable $K_D$-values were determined for the corresponding antibody which were purified via Protein G affinity-chromatography.

Material and Methods

A confocal fluorescence microscope (e.g. the commercial fluorescence correlation spectrometer Confocor, Zeiss and EVOTEC, Germany) and Fluorescence Correlation Spectroscopy (FCS) and Fluorescence Intensity Distribution Analysis (FIDA) detection technology were used to measure the binding reaction of a theophylline-specific monoclonal antibody for its cognate antigen theophylline(1,3-dimethylxanthine).

Hybridoma Cell Lines

The hybridoma cell line used for the described experiments has been shown to stably produce monoclonal antibodies which specifically bind theophylline (ATCC accession number: HB-8152).

Synthesis of the Theophylline-TAMRA Conjugate

The covalent coupling of theophylline to a tetramethyl-rhodamine derivative (TAMRA) was carried out on the solid phase by using the following protocoll: 11.0 mg of N-α-(9-fluorenylmethyloxycarbonyl)-γ-(tert-butoxycarbonyl)-L-diaminobutanoic acid (Fmoc-Dab(Boc)-OH) was coupled to 10 mg 4-methylbenzhydrylamine resin (loading: 0.5 mmol/g) by using standard PyBOP activation (26mg benzotriazole-1-yl-tris-pyrrolidino-phosphorium hexafluorophosphate, 5.5 µl N-methylmorpholine in 250 µl dimethylformamide). After cleavage of the Fmoc-group (250 µl 20% piperidine in dimethylformamide for 20 min), 6.7 mg of 8-(3-carboxypropyl)-theophylline was coupled to the resin bound diaminobutanoic acid by using PyBOP activation (26 mg benzotriazole-1-yl-tris-pyrrolidino-phosphonium hexafluorophosphate, 5.5 µl N-methylmorpholine in 125 µl dimethylformamide/125 µl N-methylpyrrolidone). Treatment with 300 µl 50% trifluoroacetic acid in dichloromethane twice for 15 min resulted in Boc cleavage. After washing and neutralisation with 0.5 ml 10% N-ethyldiisopropylamine in dimethylformamide for 10 min a solution of 13.2 mg 5-carboxytetramethyl-rhodamine succinimidyl ester (5-TAMRA, SE) in 500 µl dimethylformamide was added and the reaction was allowed to proceed over night. The reaction mixture was filtered out and the resin was washed five times with 100 ml dichloromethane. The resulting theophylline conjugate was cleaved from the resin by treatment with 250 µl of 10% trifluoromethanesulfonic acid in trifluoroacetic acid for 2.5 hours. The resin was removed by filtration under reduced pressure.

To precipitate the crude product an 8–10 fold volume of cold tert-butyl methyl ether was added to the filtrate. Finally, the fluorescent theophylline-TAMRA conjugate was purified by reversed phase-HPLC.

Fluorescence Correlation Spectroscopy (FCS)—Prior Art

FCS takes advantage of differences in the translational diffusion of large versus small molecules detecting significant changes in molecular weight upon molecular interaction, thus discriminating between the bound and the non-bound fraction of the ligand. Each molecule which diffuses through the illuminated confocal focus gives rise to bursts of fluorescent light quanta during the entire course of its journey, giving rise to characteristic fluctuations of the overall fluorescence signal. The length of each photon burst corresponds to the time the molecule spends in the confocal focus. The photons emitted are recorded in a time-resolved manner by a highly sensitive single-photon detection device. This detection method achieves single molecule sensitivity, but the fact that diffusion is a random process requires that the diffusion events for a minimum ensemble of molecules be averaged to achieve statistically reliable information. The detection of diffusion events enables a diffusion coefficient to be determined which serves as a parameter to distinguish between different fluorescent species in solution, for example between free or bound ligand.

Fluorescence Intensity Distribution Analysis (FIDA)—One Embodiment of the Present Invention FIDA, a method for the analysis of the fluorescence brightness of a mixture of particles in solution is based on a similar optical and electronic configuration employed for FCS analysis, but utilizes a different algorithm for analysis. This method (which represents one embodiment of the present invention) measures the histogram of photon count numbers and determines the concentration of fluorescent particles as a function of specific brightness which is expressed as mean count-rate per given particle. It can be applied to determine concentrations of various fluorescent species in heterogeneous samples and is a valuable tool in various fields from fundamental research to very specific applications, e.g. drug discovery and diagnostics. As an example, it allows to differentiate between a fluorescently labeled antigen which is free or bound to a polyvalent receptor e.g. an divalent antibody molecule. This binding reaction can be measured for single antibody molecules in solution as well as for antibody molecules which are immobilized on the surface of hybridoma cells.

The binding reaction of theophylline-TAMRA to antibodies arrested on the cell surface of the specific hybridoma cell line HB-8152 was determined by FIDA. As a control, no cell-associated fluorescence signals were detected when an unrelated, $\beta_{1-40}$ amyloid-specific hybridoma cell line PS1-8A1-C6-D6 was incubated with the theophylline-TAMRA conjugate (FIG. 31). The cell number of a confluent hybridoma culture was determined to be $1.6 \times 10^6$ per ml and aliquotes with approx. $0.5 \times 10^6$ hybridoma cells in 100 µl were used for each single experiment. The cells were washed in 100 µl phosphate buffered saline (PBS) buffer for 5 minutes to remove soluble antibody from the assay. Subsequently, the cells were incubated for 30 minutes in 100 µl PBS containing the theophylline-TAMRA conjugate at different concentrations: 0, 0.4, 2, 8, 16, 40, 200, 800 nM. For each measurement 50 µl of each of the cell suspensions were pipetted in a chamber slide (Nunc) and analysed in a ConfoCor employing FIDA (wavelenghts: excitation: 543 nm and emission: 572 nm). The degree of fluorescence labelling of the hybridoma cells was determined for each single experiment in four independent measurements. The dissociation constant ($K_D$) of HB-8152 antibody was calculated to be 33.1 nM+/−7.6 nM. As a control, no specific fluorescence signals were measured for hybridoma clone PS1-8A1-C6-D6.

In a competition experiment, the specificity of theophylline-TAMRA binding to the hybridoma HB-8152 cells was competitively inhibited by increasing concentrations of non-modified theophylline. The inhibition of theophylline-TAMRA binding to hybridoma cell line HB-8152 was measured by using the same assay protocol and FIDA analysis as described in FIG. 31. The only exception was that the hybridoma cells were labeled using a constant concentration of theophylline-TAMRA (80 nM) in combination with different concentrations of non-labelled theophylline competitor: 1, 10, 100, 300, 600, 1000, 2000, 5000 nM. The IC50 value was calculated to be 250.1 nM+/−25.5 nM. As a control, no binding of the theophylline-TAMRA conjugate to the amyloid-specific hybridoma clone PS1-8A1-C6-D6 was determined (FIG. 32).

As a reference, the determined dissociation constant ($K_D$) of the theophylline-specific antibody was confirmed in an independent FCS measurement using secreted antibody molecules which were purified from the hybridoma HB-8152 culture medium (FIG. 33). Therefore, the secreted monoclonal IgG antibody molecules were purified from the hybridoma HB-8152 culture medium using ProteinG affinity chromatography, and the concentration of the purified antibody solution was determined spectroscopically. The purified antibody was diluted at the following concentrations: 0, 1, 5, 10, 50, 100, 200, 500 nM in 100 µl PBS buffer containing a fluorescent theophylline-TAMRA conjugate (1 nM). The mixtures were incubated for 30 min to allow the formation of the antibody::theophylline-TAMRA complex. Aliquots of 30 µl were transferred in a chamber slide (Nunc) and analyzed in a Confocor using FCS. The dissociation constant ($K_D$) for the soluble antibody molecule was calculated to be 24.6 nM+/−11.5 µM which is comparable to the results obtained in the cellular FIDA measurements.

The quantitative determination of secreted biomolecules like e.g. Immunoglobulins, cytokines, growth factors, or hormones is a valuable tool in fields such as diagnostics or pharmacology. In general, the concentration and pharmacological activity of these molecules are determined for molecules which have been actually released from the cell into the extracellular medium. Here, an alternative approach is presented where the fraction of cell-bound antibody is measured by confocal microscopy and FIDA. When compared to conventional FACS, this technology according to the present invention holds substantial advantages:

First, confocal microscopy confers a much higher sensitivity by allowing the detection down to single molecules. In contrast, FACS is rather insensitive due to the non-confocal optics and limited in its applications to detect brightly stained cells.

Second, homogeneous binding assays can be employed, thus precluding an avidity-driven selection of unwanted hybridoma clones which produce low affinity IgG or IgM antibody. In addition, solution based assays reduce non-specific interactions observed in heterogeneous solid-phase assays leading to the selection of false positive clones.

Third, when hybridoma cells are labeled with the fluorescent antigen under saturating concentrations, the absolute brightness value of the cells gives an indication of the amount of produced antibody molecule. Hence, as hybridoma are not always homogeneous cultures, maintenance of efficient antibody production will indicate sequential selection of "good" producers.

Fourth, and probably most important, the monovalent fluorescent antigen binds to the hybridoma according to the binding affinity of the produced antibody. From the different brightness of fluorescently labeled hybridoma cells at increasing antigen concentrations, the $K_D$-value of the antibody can be calculated. In contrast to the Ig production capacity described above, this parameter is not influenced by the often observed statistical variations within a clonal population of hybrid cells. Therefore, the signals detected from single cells already provide sufficient information to discriminate between hybrid clones producing antibody with different affinities.

With the presented technology, rare cells producing high-affinity antibody should now be detected at much earlier time point, thus preventing overgrowth by non-producing clones. As a consequence, this technology should increase the overall accessible antibody repertoire obtained from hybridomas and accelerate the selective isolation of monospecific hybrid clones from freshly fused cells. Additional important therapeutic or diagnostic applications are the isolation of rare events like stem cells or cancer cells.

What is claimed is:

1. A method for characterizing fluorescent molecules or other particles in samples comprising the steps of a) monitoring fluctuating intensity of fluorescence emitted by the molecules or other particles in at least one measurement volume of a non-uniform spatial brightness profile by measuring numbers of photon counts in primary time intervals by a single or more photon detectors, b) determining at least one distribution function of numbers of photon counts, P(n), from the measured numbers of photon counts, c) determining physical quantities characteristic to said particles by fitting the experimentally determined distribution function of numbers of photon counts, wherein the fitting involves calculation of a theoretical distribution function of the number of photon counts P(n) through its generating function, defined as $$G(\vec{\xi}) = \sum_n \vec{\xi}^n P(n)$$

wherein step c) when calculating the theoretical distribution P(n), the spatial brightness profile is modeled by the expression:

$$\frac{dV}{dx} = A_0 x (1 + a_1 x + a_2 x^2)$$

where dV denotes a volume element, x denotes logarithm of the relative spatial brightness, $A_0$ is a constant selecting the unit of volume, and $a_1$ and $a_2$ are empirically estimated parameters.

2. A method for characterizing fluorescent molecules or other particles in samples comprising steps of a) monitoring fluctuating intensity of fluorescence emitted by the molecules or other particles in at least one measurement volume of a non-uniform spatial brightness profile by measuring numbers of photon counts in primary time intervals by a single or more photon detectors, b) determining at least one distribution function of numbers of photon counts, P(n), from the measured numbers of photon counts, c) determining physical quantities characteristic to said particles by fitting the experimentally determined distribution function of numbers of photon counts, wherein the fitting procedure involves calculation of a theoretical distribution function of the number of photon counts P(n) through its generating function, defined as $$G(\vec{\xi}) = \sum_n \vec{\xi}^n P(n)$$

wherein in step c) when calculating the theoretical distribution P(n), the spatial brightness profile is modeled by the expression $$\frac{dV}{dx} = A_0 x^{a_3} (1 + a_1 x + a_2 x^2)$$

wherein dV denotes a volume element, x denotes logarithm of the relative spatial brightness, $A_0$ is a constant selecting the unit of volume, and $a_1$, $a_2$ and $a_3$ are empirically estimated parameters.

* * * * *